US012077882B2

(12) United States Patent
Barelle et al.

(10) Patent No.: US 12,077,882 B2
(45) Date of Patent: Sep. 3, 2024

(54) FAST-TRACK HUMANISATION OF SPECIFIC BINDING MOLECULES

(71) Applicant: ELASMOGEN LTD, Aberdeenshire (GB)

(72) Inventors: Caroline Jane Barelle, Aberdeenshire (GB); Marina Kovaleva, Aberdeenshire (GB); Laura Ann Ferguson, Aberdeenshire (GB); Obinna Chukwuemeka Ubah, Aberdeenshire (GB); Andrew Justin Radcliffe Porter, Aberdeenshire (GB)

(73) Assignee: ELASMOGEN LTD, Aberdeen (GB)

(*) Notice: Subject to any disclaimer, the term of this patent is extended or adjusted under 35 U.S.C. 154(b) by 0 days.

(21) Appl. No.: 17/932,449

(22) Filed: Sep. 15, 2022

(65) Prior Publication Data

US 2024/0035020 A1    Feb. 1, 2024

Related U.S. Application Data

(63) Continuation of application No. PCT/EP2021/086492, filed on Dec. 17, 2021.

(30) Foreign Application Priority Data

Dec. 18, 2020 (GB) .................................. 2020152

(51) Int. Cl.
C40B 50/06     (2006.01)
C07K 14/195    (2006.01)
C12N 15/10     (2006.01)

(52) U.S. Cl.
CPC ............ *C40B 50/06* (2013.01); *C07K 14/195* (2013.01); *C12N 15/1082* (2013.01); *C07K 2317/24* (2013.01); *C07K 2317/31* (2013.01)

(58) Field of Classification Search
None
See application file for complete search history.

(56) References Cited

FOREIGN PATENT DOCUMENTS

| WO | 2013/167883 A9  | 11/2013 |
| WO | 2014/173959 A2  | 10/2014 |
| WO | 2015/100246 A1  | 7/2015  |
| WO | 2015/200883 A2  | 12/2015 |
| WO | 2019/063726 A1  | 4/2019  |
| WO | 2019/106694 A1  | 6/2019  |

(Continued)

OTHER PUBLICATIONS

Kovalenko et al. Atypical antigen recognition mode of a shark immunoglobulin new antigen receptor (IgNAR) variable domain characterized by humanization and structural analysis. The Journal of Biological Chemistry, 2013, 288(24), 17408-17419.

(Continued)

*Primary Examiner* — Christian C Boesen
(74) *Attorney, Agent, or Firm* — Arrigo, Lee, Guttman & Mouta-Bellum LLP

(57) ABSTRACT

The present invention relates to a synthetic library of humanised antigen specific binding molecules derived from a member of a species in the Elasmobranchii subclass, processes for the production thereof and specific antigen specific binding molecules isolated from said library. The present invention also relates to the multi-domain specific binding molecules comprising humanised Ig-like Novel Antigen Receptor variable domains (VNARs). Specific binding domains that bind to Tumour Necrosis Factor alpha (TNFα) are also provided.

7 Claims, 17 Drawing Sheets

Figure 3:
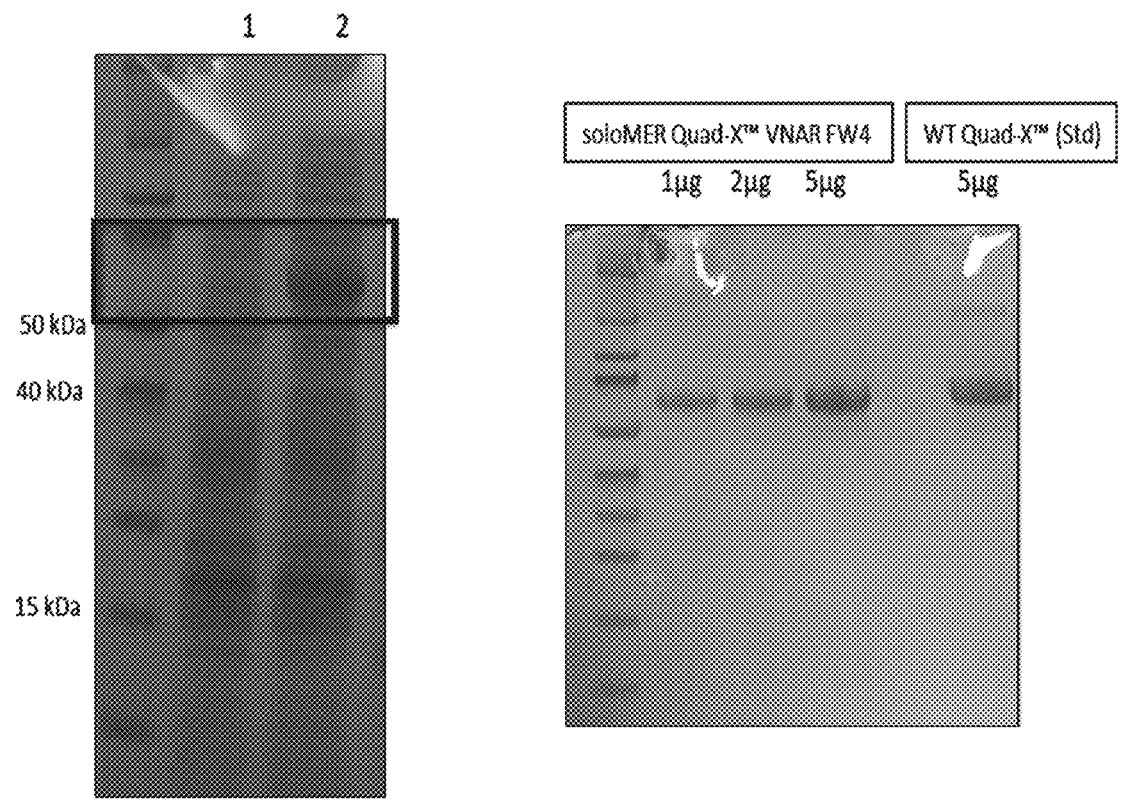

Specification includes a Sequence Listing.

(56) References Cited

FOREIGN PATENT DOCUMENTS

WO 2019/122447 A1 6/2019
WO 2019/1224445 A1 6/2019

OTHER PUBLICATIONS

Moutel et al. NaLi-H1: A universal synthetic library of humanized nanobodies providing highly functional antibodies and intrabodies. eLife, 2016, 5:e16228, 1-31. https://doi.org/10.7554/eLife.16228.
Steven et al. In Vitro maturation of a humanized shark VNAR domain to improve its biophysical properties to facilitate clinical development. Frontiers in Immunology. 2017, 13, 1-15.
Ubah et al. Novel, anti hTNF-α variable new antigen receptor formats with enhanced neutralizing potency and multifunctionality, generated for therapeutic development. Frontier in Immunology, vol. 8, 1780, 2017, 1-13.
Ubah et al. In Vitro Elisa and Cell-Based assays confirm the low immunogenicity of VNAR therapeutics constructs in a mouse model of human RA: An encouraging mileston to further clinical drug development. Journal of Immunology Research. vol. 2020, 7283239, 1-14. https://doi.org/10.1155/2020/7283239.

Fig. 1

Fig. 2

Key:

Lane 1 = soloMER D1-Fc-C4 Quad-X (VNAR FW1)

Lane 2 = soloMER D1-Fc-C4 Quad-X (VNAR FW4)

Fig. 7 soloMER: FW1 | CDR1 | FW2 | HV | FW3 | HV4 | FW3b | CDR3 | FW4

| CDR1 Diversity | | | | | | | |
|---|---|---|---|---|---|---|---|
| Position | 26 | 27 | 28 | 29 | 30 | 31 | 32 | 33 |
| Residues | D | T | K | Y | G | W | F | S |
| | G | A | R | | A | L | Y | A |
| | | | E | | | | | |
| | | | D | | | | | |
| | | | N | | | | | |
| | | | S | | | | | |
| | | | G | | | | | |
| Diversity | 448 | | | | | | | |

| HV2 Diversity | | | | | | | | | |
|---|---|---|---|---|---|---|---|---|---|
| Position | 44 | 45 | 46 | 47 | 48 | 49 | 50 | 51 | 52 |
| Residues | S | N | K | D | R | M | S | I | G |
| | T | D | E | E | S | I | | K | K |
| | p | | E | | | | | | S |
| | | | | | | | | | N |
| Diversity | 768 | | | | | | | | |

| HV4 Diversity | | | | | |
|---|---|---|---|---|---|
| Position | 61 | 62 | 63 | 64 | 65 |
| Residues | K | G | T | K | S |
| | N | R | p | M | |
| | | | S | | |
| Diversity | 24 | | | | |

| Total |
|---|
| 8.2x10⁶ |

Fig. 11

Fig. 14

>D3WT
ASVNQTPRTATKETGESLIINCVLTDTSYGLYSTSWFRKNPGTTDWERMSIGGRYVESVNKRAKSFSLRIKDLTVADSATYYCKAQSGMAIST SEQ ID NO: 84
GSGHGYNWYDGAGTVLIVN
>V1
ASVNQSPSSLSASVGDRVTITCVLTDTSYGLYSTSWFRKNPGTTDWERMSIGGRYVESVNKRAKSFSLRIKDLTVADSATYYCKAQSGMAIST SEQ ID NO: 85
GSGHGYNWYDGAGTKVEIK
>V2
ASVNQSPSSLSASVGDRVTITCVLTDTSYGLYSTSWFRKNPGTTDWERMSIGGRYVESVNKRAKSFTLTISSLQPEDFATYYCKAQSGMAIST SEQ ID NO: 86
GSGHGYNWYDGAGTKVEIK
>V4
ASVNQSPSSLSASVGDRVTITCVLTDTSYGLYSTSWYQQKPGTTDWERMSIGGRYVESVNKRAKSFTLTISSLQPEDFATYYCKAQSGMAIST SEQ ID NO: 87
GSGHGYNWYDGAGTKVEIK
>V5
ASVNQSPSSLSASVGDRVTITCVLTDTSYGLYSTSWYQQKPGTTDWERMSIGGRFSGSGSKRAKSFTLTISSLQPEDFATYYCKAQSGMAIST SEQ ID NO: 88
GSGHGYNWYDGAGTKVEIK

Fig. 15

| FW1 | CDR1 | FW2 | HV2 | FW3a | HV4 | FW3b | CDR3 | FW4 |
|---|---|---|---|---|---|---|---|---|
| ASVNQSPSSLSASVGDRVTITCVLT | DTSYGLYS | TSWFRKNPGT | TDWERMSIG | GRYVESVN | KRAKS | FTLTISSLQPEDFATYYCKA | QSGMAISTGSGHGYNWV | DGAGTKVEIK |
| SEQ ID NO: 89 | SEQ ID NO: 90 | SEQ ID NO: 91 | SEQ ID NO: 92 | SEQ ID NO: 93 | SEQ ID NO: 94 | SEQ ID NO: 95 | SEQ ID NO: 96 | SEQ ID NO: 97 |

CDR1 Diversity

| Residue | 2 | 2 | 2 | 2 | 3 | 3 | 3 | 3 |
|---|---|---|---|---|---|---|---|---|
|  | 6 | 7 | 8 | 9 | 0 | 1 | 2 | 3 |
|  | D | T | K | Y | G | L | Y | S |
|  | G | A | R | Y | A | W | F | A |
|  |   |   | E | Y |   | Y | L |   |
|  |   |   | D | Y |   |   | Y |   |
|  |   |   | N | Y |   |   | S |   |
|  |   |   | G | Y |   |   |   |   |
| Possible combinations | 2 | 2 | 7 | 1 | 2 | 2 | 2 | 2 |
| Total diversity | 448 combinations |

HV2 diversity

| Residue | 4 | 4 | 4 | 4 | 4 | 4 | 5 | 5 |
|---|---|---|---|---|---|---|---|---|
|  | 4 | 5 | 6 | 7 | 8 | 9 | 0 | 1 |
|  | S | N | K | D | R | I | S | G |
|  | T | D | E | E | S | M | I | N |
|  | P |   |   |   |   |   |   | S |
| Possible combinations | 3 | 2 | 2 | 2 | 2 | 2 | 2 | 2 |
| Total diversity | 768 combinations |

HV4 diversity

| Residue | 6 | 6 | 6 | 6 | 6 | 6 |
|---|---|---|---|---|---|---|
|  | 1 | 2 | 3 | 4 | 5 |
|  | K | G | T | K | S |
|  | N | R | P | M |   |
|  |   |   |   | S |   |
| Possible combinations | 2 | 2 | 2 | 3 | 2 | 1 |
| Total diversity | 24 combinations |

Total library diversity: $8.2 \times 10^6$

Fig. 16

F11_ASVNQSPSSLSASVGDRVTITCVLTDTNYGLYATSWFRKNPGTSNEDRIISGRYVESVNKRTKSFTLTISSLQPEDFATYYCKAQSG
MAISTGSGHGYNWYDGAGTKVEIKQASGAAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGESHHHHHH                                    SEQ ID NO: 98

E08_ASVNQSPSSLSASVGDRVTITCVLTDTRYGLYSTSWFRKNPGTTDKERISIGGRYVESVNKRTKSFTLTISSLQPEDFATYYCKAQSG
MAISTGSGHGYNWYDGAGTKVEIKQASGAAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGESHHHHHH                                    SEQ ID NO: 99

F01_ASVNQSPSSLSASVGDRVTITCVLTDTKYGLYSTSWFRKNPGTTDKERISIGGRYVESVNKRTKSFTLTISSLQPEDFATYYCKAQSG
MAISTGSGHGYNWYDGAGTKVEIKQASGAAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGESHHHHHH                                    SEQ ID NO: 100

G02_ASVNQSPSSLSASVGDRVTITCVLTDTNYGLYATSWFRKNPGTTDEERMSIGGRYVESVNKRSKSFTLTISSLQPEDFATYYCKAQS
GMAISTGSGHGYNWYDGAGTKVEIKQASGAAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGESHHHHHH                                   SEQ ID NO: 101

Fig. 18

SEQUENCE LISTING

```
Sequence total quantity: 101
SEQ ID NO: 1            moltype = AA  length = 28
FEATURE                 Location/Qualifiers
REGION                  1..28
                        note = Consensus sequence - humanised FW1
```

```
VARIANT          1
                 note = Where X is - or D
VARIANT          2
                 note = Where X is A or I or T
VARIANT          3
                 note = Where X is S or Q or R
VARIANT          4
                 note = Where X is V or M
VARIANT          5
                 note = Where X is N or T or D
VARIANT          25
                 note = Where X is L or V
VARIANT          26
                 note = Where X is T or R
VARIANT          27
                 note = Where X is D or G
VARIANT          28
                 note = Where X is T or A or S
source           1..28
                 mol_type = protein
                 organism = synthetic construct
SEQUENCE: 1
XXXXXQSPSS LSASVGDRVT ITCVXXXX                                                  28

SEQ ID NO: 2           moltype =    length =
SEQUENCE: 2
000

SEQ ID NO: 3           moltype =    length =
SEQUENCE: 3
000

SEQ ID NO: 4           moltype = AA  length = 20
FEATURE                Location/Qualifiers
REGION                 1..20
                       note = Consensus sequence - FW3b
VARIANT          2
                 note = Where X is S or T
VARIANT          4
                 note = Where X is R or T
VARIANT          6
                 note = Where X is K or S or N
VARIANT          7
                 note = Where X is D or S
VARIANT          9
                 note = Where X is T or Q
VARIANT          10
                 note = Where X is V or P
VARIANT          11
                 note = Where X is A or E
VARIANT          13
                 note = Where X is S or F
VARIANT          14
                 note = Where X is A or G
VARIANT          17
                 note = Where X is Y or R or I
VARIANT          19
                 note = Where X is K or R or A
VARIANT          20
                 note = Where X is A or S or L
source           1..20
                 mol_type = protein
                 organism = synthetic construct
SEQUENCE: 4
FXLXIXXLXX XDXXTYXCXX                                                           20

SEQ ID NO: 5           moltype =    length =
SEQUENCE: 5
000

SEQ ID NO: 6           moltype = AA  length = 27
FEATURE                Location/Qualifiers
REGION                 1..27
                       note = Consensus sequence - V1 to V5 FW1
VARIANT          1
                 note = Where X is A or T
VARIANT          2
                 note = Where X is S or R
VARIANT          4
```

```
                        note = Where X is N or D
VARIANT                 24
                        note = Where X is L or V
VARIANT                 26
                        note = Where X is D or G
VARIANT                 27
                        note = Where X is T or A
source                  1..27
                        mol_type = protein
                        organism = synthetic construct
SEQUENCE: 6
XXVXQSPSSL SASVGDRVTI TCVXTXX                                              27

SEQ ID NO: 7            moltype = AA   length = 28
FEATURE                 Location/Qualifiers
REGION                  1..28
                        note = Consensus sequence - V6 FW1
VARIANT                 25
                        note = Where X is L or V
VARIANT                 27
                        note = Where X is D or G
VARIANT                 28
                        note = Where X is T or A
source                  1..28
                        mol_type = protein
                        organism = synthetic construct
SEQUENCE: 7
DIQMTQSPSS LSASVGDRVT ITCVXTXX                                             28

SEQ ID NO: 8            moltype = AA   length = 27
FEATURE                 Location/Qualifiers
REGION                  1..27
                        note = soloMER D1v2 / C4v1 QuadX - FW1
source                  1..27
                        mol_type = protein
                        organism = synthetic construct
SEQUENCE: 8
ARVDQSPSSL SASVGDRVTI TCVLRDS                                              27

SEQ ID NO: 9            moltype = AA   length = 10
FEATURE                 Location/Qualifiers
REGION                  1..10
                        note = Consensus sequence - V1 to V3 FW2
VARIANT                 2
                        note = Where X is S or Y
VARIANT                 4
                        note = Where X is F or Y
VARIANT                 10
                        note = Where X is T or S
source                  1..10
                        mol_type = protein
                        organism = synthetic construct
SEQUENCE: 9
TXWXRKNPGX                                                                 10

SEQ ID NO: 10           moltype = AA   length = 10
FEATURE                 Location/Qualifiers
REGION                  1..10
                        note = Consensus sequence - V4 to V6 FW2
VARIANT                 2
                        note = Where X is S or Y
VARIANT                 4
                        note = Where X is Y or F
VARIANT                 10
                        note = Where X is T or S
source                  1..10
                        mol_type = protein
                        organism = synthetic construct
SEQUENCE: 10
TXWXQQKPGX                                                                 10

SEQ ID NO: 11           moltype = AA   length = 10
FEATURE                 Location/Qualifiers
REGION                  1..10
                        note = soloMER D1v2 / C4v1 QuadX - FW2
source                  1..10
                        mol_type = protein
                        organism = synthetic construct
SEQUENCE: 11
```

```
TYWYRKKSGS                                                                  10

SEQ ID NO: 12           moltype = AA  length = 8
FEATURE                 Location/Qualifiers
REGION                  1..8
                        note = FW3a V1, V2, V3
source                  1..8
                        mol_type = protein
                        organism = synthetic construct
SEQUENCE: 12
GRYVESVN                                                                    8

SEQ ID NO: 13           moltype = AA  length = 8
FEATURE                 Location/Qualifiers
REGION                  1..8
                        note = FW3a V4, V5, V6
source                  1..8
                        mol_type = protein
                        organism = synthetic construct
SEQUENCE: 13
GRFSGSGS                                                                    8

SEQ ID NO: 14           moltype = AA  length = 8
FEATURE                 Location/Qualifiers
REGION                  1..8
                        note = soloMER D1v2 FW3a
source                  1..8
                        mol_type = protein
                        organism = synthetic construct
SEQUENCE: 14
GRYVETVN                                                                    8

SEQ ID NO: 15           moltype = AA  length = 8
FEATURE                 Location/Qualifiers
REGION                  1..8
                        note = soloMER C4v1 FW3a
source                  1..8
                        mol_type = protein
                        organism = synthetic construct
SEQUENCE: 15
GRYVETIN                                                                    8

SEQ ID NO: 16           moltype = AA  length = 20
FEATURE                 Location/Qualifiers
REGION                  1..20
                        note = Consensus sequence - FW3b
VARIANT                 17
                        note = Where X is Y or I
VARIANT                 19
                        note = Where X is K or R
source                  1..20
                        mol_type = protein
                        organism = synthetic construct
SEQUENCE: 16
FSLRIKDLTV ADSATYXCXA                                                       20

SEQ ID NO: 17           moltype = AA  length = 20
FEATURE                 Location/Qualifiers
REGION                  1..20
                        note = Consensus sequence - FW3b
VARIANT                 17
                        note = Where X is Y or I
VARIANT                 19
                        note = Where X is K or R
source                  1..20
                        mol_type = protein
                        organism = synthetic construct
SEQUENCE: 17
FTLTISSLQP EDFATYXCXA                                                       20

SEQ ID NO: 18           moltype = AA  length = 20
FEATURE                 Location/Qualifiers
REGION                  1..20
                        note = soloMER D1v2 FW3b
source                  1..20
                        mol_type = protein
                        organism = synthetic construct
SEQUENCE: 18
FTLTISSLQP EDFATYYCAS                                                       20
```

```
SEQ ID NO: 19           moltype = AA  length = 20
FEATURE                 Location/Qualifiers
REGION                  1..20
                        note = soloMER C4v1 Fw3b
source                  1..20
                        mol_type = protein
                        organism = synthetic construct
SEQUENCE: 19
FSLRINDLTV EDSGTYRCKL                                                   20

SEQ ID NO: 20           moltype = AA  length = 10
FEATURE                 Location/Qualifiers
REGION                  1..10
                        note = Consensus sequence - FW4
VARIANT                 1
                        note = Where X is D or Y or F
VARIANT                 3
                        note = Where X is A or G or Q
VARIANT                 7
                        note = Where X is V or L
source                  1..10
                        mol_type = protein
                        organism = synthetic construct
SEQUENCE: 20
XGXGTKXEIK                                                              10

SEQ ID NO: 21           moltype = AA  length = 10
FEATURE                 Location/Qualifiers
REGION                  1..10
                        note = soloMER D1v2 / C4v1 QuadX - FW4
source                  1..10
                        mol_type = protein
                        organism = synthetic construct
SEQUENCE: 21
YGGGTVVTVN                                                              10

SEQ ID NO: 22           moltype =   length =
SEQUENCE: 22
000

SEQ ID NO: 23           moltype =   length =
SEQUENCE: 23
000

SEQ ID NO: 24           moltype = AA  length = 20
FEATURE                 Location/Qualifiers
REGION                  1..20
                        note = Consensus sequence - FW3b
VARIANT                 2
                        note = Where X is S or T
VARIANT                 4
                        note = Where X is R or T
VARIANT                 6
                        note = Where X is K or S or N
VARIANT                 7
                        note = Where X is D or S
VARIANT                 9
                        note = Where X is T or Q
VARIANT                 10
                        note = Where X is V or P
VARIANT                 11
                        note = Where X is A or E
VARIANT                 13
                        note = Where X is S or F
VARIANT                 14
                        note = Where X is A or G
VARIANT                 17
                        note = Where X is Y or R or I
VARIANT                 19
                        note = Where X is K or R or A
VARIANT                 20
                        note = Where X is A or S or L
source                  1..20
                        mol_type = protein
                        organism = synthetic construct
SEQUENCE: 24
FXLXIXXLXX XDXXTYXCXX                                                   20
```

```
SEQ ID NO: 25          moltype = AA   length = 10
FEATURE                Location/Qualifiers
REGION                 1..10
                       note = Consensus sequence - FW4
VARIANT                1
                       note = Where X is D or Y
source                 1..10
                       mol_type = protein
                       organism = synthetic construct
SEQUENCE: 25
XGAGTKVEIK                                                                        10

SEQ ID NO: 26          moltype =     length =
SEQUENCE: 26
000

SEQ ID NO: 27          moltype = AA   length = 9
FEATURE                Location/Qualifiers
REGION                 1..9
                       note = Consensus sequence - HV2
VARIANT                1
                       note = Where X is S or T or P
VARIANT                2
                       note = Where X is N or D
VARIANT                3
                       note = Where X is Q or W
VARIANT                6
                       note = Where X is I or M
VARIANT                9
                       note = Where X is G or S
source                 1..9
                       mol_type = protein
                       organism = synthetic construct
SEQUENCE: 27
XXXERXSIX                                                                          9

SEQ ID NO: 28          moltype =     length =
SEQUENCE: 28
000

SEQ ID NO: 29          moltype = AA   length = 6
FEATURE                Location/Qualifiers
REGION                 1..6
                       note = CDR1 of the first VNAR domain
source                 1..6
                       mol_type = protein
                       organism = synthetic construct
SEQUENCE: 29
HCATSS                                                                             6

SEQ ID NO: 30          moltype = AA   length = 6
FEATURE                Location/Qualifiers
REGION                 1..6
                       note = CDR1 of the second VNAR domain
source                 1..6
                       mol_type = protein
                       organism = synthetic construct
SEQUENCE: 30
NCGLSS                                                                             6

SEQ ID NO: 31          moltype = AA   length = 6
FEATURE                Location/Qualifiers
REGION                 1..6
                       note = CDR1 of the VNAR domain
source                 1..6
                       mol_type = protein
                       organism = synthetic construct
SEQUENCE: 31
NCALSS                                                                             6

SEQ ID NO: 32          moltype = AA   length = 9
FEATURE                Location/Qualifiers
REGION                 1..9
                       note = HV2 of the first and second VNAR domain
source                 1..9
                       mol_type = protein
                       organism = synthetic construct
SEQUENCE: 32
TNEESISKG                                                                          9
```

```
SEQ ID NO: 33              moltype = AA   length = 5
FEATURE                    Location/Qualifiers
REGION                     1..5
                           note = HV4 of the first VNAR domain
source                     1..5
                           mol_type = protein
                           organism = synthetic construct
SEQUENCE: 33
SGSKS                                                                  5

SEQ ID NO: 34              moltype = AA   length = 5
FEATURE                    Location/Qualifiers
REGION                     1..5
                           note = HV4 of the second VNAR domain
source                     1..5
                           mol_type = protein
                           organism = synthetic construct
SEQUENCE: 34
EGSKS                                                                  5

SEQ ID NO: 35              moltype = AA   length = 11
FEATURE                    Location/Qualifiers
REGION                     1..11
                           note = CDR3 of the first VNAR domain
source                     1..11
                           mol_type = protein
                           organism = synthetic construct
SEQUENCE: 35
ECQYGLAEYD V                                                          11

SEQ ID NO: 36              moltype = AA   length = 14
FEATURE                    Location/Qualifiers
REGION                     1..14
                           note = CDR3 of the second VNAR domain
source                     1..14
                           mol_type = protein
                           organism = synthetic construct
SEQUENCE: 36
SWWTQNWRCS NSDV                                                       14

SEQ ID NO: 37              moltype = AA   length = 23
FEATURE                    Location/Qualifiers
REGION                     1..23
                           note = CDR3 of a further VNAR domain
source                     1..23
                           mol_type = protein
                           organism = synthetic construct
SEQUENCE: 37
YIPCIDELVY MISGGTSGPI HDV                                             23

SEQ ID NO: 38              moltype = AA   length = 106
FEATURE                    Location/Qualifiers
REGION                     1..106
                           note = soloMER D1 QuadX v2
source                     1..106
                           mol_type = protein
                           organism = synthetic construct
SEQUENCE: 38
ARVDQSPSSL SASVGDRVTI TCVLRDSHCA TSSTYWYRKK SGSTNEESIS KGGRYVETVN      60
SGSKSFTLTI SSLQPEDFAT YYCASECQYG LAEYDVYGGG TVVTVN                    106

SEQ ID NO: 39              moltype = AA   length = 109
FEATURE                    Location/Qualifiers
REGION                     1..109
                           note = soloMER DC4 QuadX v2
source                     1..109
                           mol_type = protein
                           organism = synthetic construct
SEQUENCE: 39
ARVDQSPSSL SASVGDRVTI TCVLRDSNCG LSSTYWYRKK SGSTNEESIS KGGRYVETIN      60
EGSKSFSLRI NDLTVEDSGT YRCKLSWWTQ NWRCSNSDVY GGGTVVTVN                 109

SEQ ID NO: 40              moltype = AA   length = 107
FEATURE                    Location/Qualifiers
REGION                     1..107
                           note = DPK-9
source                     1..107
                           mol_type = protein
```

```
                        organism = synthetic construct
SEQUENCE: 40
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPNTFGQ GTKVEIK                 107

SEQ ID NO: 41           moltype = DNA   length = 19
FEATURE                 Location/Qualifiers
misc_feature            1..19
                        note = Primer D3_FOR_NCoI
source                  1..19
                        mol_type = other DNA
                        organism = synthetic construct
SEQUENCE: 41
agccggccat ggccgcttc                                                 19

SEQ ID NO: 42           moltype = DNA   length = 24
FEATURE                 Location/Qualifiers
misc_feature            1..24
                        note = Primer D3_REV_NotI
source                  1..24
                        mol_type = other DNA
                        organism = synthetic construct
SEQUENCE: 42
atgtgcggcc gccctgagg cctg                                            24

SEQ ID NO: 43           moltype = AA    length = 106
FEATURE                 Location/Qualifiers
REGION                  1..106
                        note = D1
source                  1..106
                        mol_type = protein
                        organism = synthetic construct
SEQUENCE: 43
ARVDQTPQTI TKETGESLTI NCVLRDSHCA TSSTYWYRKK SGSTNEESIS KGGRYVETVN    60
SGSKSFSLRI NDLTVEDSGT YRCASECQYG LAEYDVYGGG TVVTVN                  106

SEQ ID NO: 44           moltype = AA    length = 106
FEATURE                 Location/Qualifiers
REGION                  1..106
                        note = D1-V1
source                  1..106
                        mol_type = protein
                        organism = synthetic construct
SEQUENCE: 44
ARVDQSPSSL SASVGDRVTI TCVLRDSHCA TSSTYWYRKK SGSTNEESIS KGGRYVETVN    60
SGSKSFSLRI NDLTVEDSGT YRCASECQYG LAEYDVYGGG TKVEIK                  106

SEQ ID NO: 45           moltype = AA    length = 106
FEATURE                 Location/Qualifiers
REGION                  1..106
                        note = D1-V2
source                  1..106
                        mol_type = protein
                        organism = synthetic construct
SEQUENCE: 45
ARVDQSPSSL SASVGDRVTI TCVLRDSHCA TSSTYWYRKK SGSTNEESIS KGGRYVETVN    60
SGSKSFTLTI SSLQPEDFAT YYCASECQYG LAEYDVYGGG TKVEIK                  106

SEQ ID NO: 46           moltype = AA    length = 106
FEATURE                 Location/Qualifiers
REGION                  1..106
                        note = D1-V3
source                  1..106
                        mol_type = protein
                        organism = synthetic construct
SEQUENCE: 46
ARVDQSPSSL SASVGDRVTI TCVLRDSHCA TSSTYWYRKK PGSTNEESIS KGGRFSGSGS    60
SGSKSFTLTI SSLQPEDFAT YYCASECQYG LAEYDVFGQG TKVEIK                  106

SEQ ID NO: 47           moltype = AA    length = 106
FEATURE                 Location/Qualifiers
REGION                  1..106
                        note = D1-V4
source                  1..106
                        mol_type = protein
                        organism = synthetic construct
SEQUENCE: 47
ARVDQSPSSL SASVGDRVTI TCVLRDSHCA TSSTYWYRKK PGSTNEESIS KGGRFSGSGS    60
SGSKSFTLTI SSLQPEDFAT YYCASECQYG LAEYDVFGQG TKVEIK                  106
```

```
SEQ ID NO: 48          moltype = AA  length = 106
FEATURE                Location/Qualifiers
REGION                 1..106
                       note = D1-V5
source                 1..106
                       mol_type = protein
                       organism = synthetic construct
SEQUENCE: 48
ARVDQSPSSL SASVGDRVTI TCVLRDSHCA TSSTYWYQQK PGSTNEESIS KGGRFSGSGS    60
SGSKSFTLTI SSLQPEDFAT YYCASECQYG LAEYDVFGQG TKVEIK                  106

SEQ ID NO: 49          moltype = AA  length = 107
FEATURE                Location/Qualifiers
REGION                 1..107
                       note = D1-V6
source                 1..107
                       mol_type = protein
                       organism = synthetic construct
SEQUENCE: 49
DIQMTQSPSS LSASVGDRVT ITCVLRDSHC ATSSTYWYQQ KPGSTNEESI SKGGRFSGSG    60
SSGSKSFTLT ISSLQPEDFA TYYCASECQY GLAEYDVFGQ GTKVEIK                 107

SEQ ID NO: 50          moltype = AA  length = 109
FEATURE                Location/Qualifiers
REGION                 1..109
                       note = C4
source                 1..109
                       mol_type = protein
                       organism = synthetic construct
SEQUENCE: 50
ARVDQTPQTI TKETGESLTI NCVLRDSNCG LSSTYWYRKK SGSTNEESIS KGGRYVETIN    60
EGSKSFSLRI NDLTVEDSGT YRCKLSWWTQ NWRCSNSDVY GGGTVVTVN               109

SEQ ID NO: 51          moltype = AA  length = 109
FEATURE                Location/Qualifiers
REGION                 1..109
                       note = C4-V1
source                 1..109
                       mol_type = protein
                       organism = synthetic construct
SEQUENCE: 51
ARVDQSPSSL SASVGDRVTI TCVLRDSNCG LSSTYWYRKK SGSTNEESIS KGGRYVETIN    60
EGSKSFSLRI NDLTVEDSGT YRCKLSWWTQ NWRCSNSDVY GGGTKVEIK               109

SEQ ID NO: 52          moltype = AA  length = 109
FEATURE                Location/Qualifiers
REGION                 1..109
                       note = C4-V2
source                 1..109
                       mol_type = protein
                       organism = synthetic construct
SEQUENCE: 52
ARVDQSPSSL SASVGDRVTI TCVLRDSNCG LSSTYWYRKK SGSTNEESIS KGGRYVETIN    60
EGSKSFTLTI SSLQPEDFAT YYCKLSWWTQ NWRCSNSDVF GQGTKVEIK               109

SEQ ID NO: 53          moltype = AA  length = 109
FEATURE                Location/Qualifiers
REGION                 1..109
                       note = C4-V3
source                 1..109
                       mol_type = protein
                       organism = synthetic construct
SEQUENCE: 53
ARVDQSPSSL SASVGDRVTI TCVLRDSNCG LSSTYWYQQK PGKTNEESIS KGGRYVETIN    60
EGSKSFTLTI SSLQPEDFAT YYCKLSWWTQ NWRCSNSDVF GQGTKVEIK               109

SEQ ID NO: 54          moltype = AA  length = 109
FEATURE                Location/Qualifiers
REGION                 1..109
                       note = C4-V4
source                 1..109
                       mol_type = protein
                       organism = synthetic construct
SEQUENCE: 54
ARVDQSPSSL SASVGDRVTI TCVLRDSNCG LSSTYWYRKK SGSTNEESIS KGGRFSGSGS    60
EGSKSFTLTI SSLQPEDFAT YYCKLSWWTQ NWRCSNSDVF GQGTKVEIK               109

SEQ ID NO: 55          moltype = AA  length = 109
```

```
FEATURE                 Location/Qualifiers
REGION                  1..109
                        note = C4-V5
source                  1..109
                        mol_type = protein
                        organism = synthetic construct
SEQUENCE: 55
ARVDQSPSSL SASVGDRVTI TCVLRDSNCG LSSTYWYQQK PGSTNEESIS KGGRFSGSGS    60
EGSKSFTLTI SSLQPEDFAT YYCKLSWWTQ NWRCSNSDVF GQGTKVEIK              109

SEQ ID NO: 56           moltype = AA   length = 110
FEATURE                 Location/Qualifiers
REGION                  1..110
                        note = C4-V6
source                  1..110
                        mol_type = protein
                        organism = synthetic construct
SEQUENCE: 56
DIQMTQSPSS LSASVGDRVT ITCVLRDSNC GLSSTYWYQQ KPGSTNEESI SKGGRFSGSG    60
SEGSKSFTLT ISSLQPEDFA TYYCKLSWWT QNWRCSNSDV FGQGTKVEIK              110

SEQ ID NO: 57           moltype = AA   length = 140
FEATURE                 Location/Qualifiers
REGION                  1..140
                        note = Consensus
source                  1..140
                        mol_type = protein
                        organism = synthetic construct
SEQUENCE: 57
ARVDQTPQTI TKETGESLTI NCVLRDSHCA TSSTYWYRKK SGSTNEESIS KGGRYVETVN    60
SGSKSFTLTI SSLQPEDFAT YYCASECQYG LAEYDVYGGG TVVTVNGSGG GSGGGGSGEP   120
KSSDKTHTCP PCPAPELLGG                                               140

SEQ ID NO: 58           moltype = AA   length = 484
FEATURE                 Location/Qualifiers
REGION                  1..484
                        note = soloMER D1-Fc-C4 Quad-X (NAR FW1)
source                  1..484
                        mol_type = protein
                        organism = synthetic construct
SEQUENCE: 58
ARVDQTPQTI TKETGESLTI NCVLRDSHCA TSSTYWYRKK SGSTNEESIS KGGRYVETVN    60
SGSKSFTLTI SSLQPEDFAT YYCASECQYG LAEYDVYGGG TKVEIKGSGG GSGGGGSGEP   120
KSSDKTHTCP PCPAPELLGG PSVFLFPPKP KDTLMISRTP EVTCVVVDVS HEDPEVKFNW   180
YVDGVEVHNA KTKPREEQYN STYRVVSVLT VLHQDWLNGK EYKCKVSNKA LPAPIEKTIS   240
KAKGQPREPQ VYTLPPSRDE LTKNQVSLTC LVKGFYPSDI AVEWESNGQP ENNYKTTPPV   300
LDSDGSFFLY SKLTVDKSRW QQGNVFSCSV MHEALHNHYT QKSLSLSPGK GGGGSGGGGS   360
GGGGSGGGGS GGGGSARVDQ TPQTITKETG ESLTINCVLR DSNCGLSSTY WYRKKSGSTN   420
EESISKGGRY VETINEGSKS FSLRINDLTV EDSGTYRCKL SWWTQNWRCS NSDVYGGGTK   480
VEIK                                                                484

SEQ ID NO: 59           moltype = AA   length = 484
FEATURE                 Location/Qualifiers
REGION                  1..484
                        note = soloMER D1-Fc-C4 Quad-X (NAR FW4)-Lead
source                  1..484
                        mol_type = protein
                        organism = synthetic construct
SEQUENCE: 59
ARVDQSPSSL SASVGDRVTI TCVLRDSHCA TSSTYWYRKK SGSTNEESIS KGGRYVETVN    60
SGSKSFTLTI SSLQPEDFAT YYCASECQYG LAEYDVYGGG TVVTVNGSGG GSGGGGSGEP   120
KSSDKTHTCP PCPAPELLGG PSVFLFPPKP KDTLMISRTP EVTCVVVDVS HEDPEVKFNW   180
YVDGVEVHNA KTKPREEQYN STYRVVSVLT VLHQDWLNGK EYKCKVSNKA LPAPIEKTIS   240
KAKGQPREPQ VYTLPPSRDE LTKNQVSLTC LVKGFYPSDI AVEWESNGQP ENNYKTTPPV   300
LDSDGSFFLY SKLTVDKSRW QQGNVFSCSV MHEALHNHYT QKSLSLSPGK GGGGSGGGGS   360
GGGGSGGGGS GGGGSARVDQ SPSSLSASVG DRVTITCVLR DSNCGLSSTY WYRKKSGSTN   420
EESISKGGRY VETINEGSKS FSLRINDLTV EDSGTYRCKL SWWTQNWRCS NSDVYGGGTV   480
VTVN                                                                484

SEQ ID NO: 60           moltype = AA   length = 483
FEATURE                 Location/Qualifiers
REGION                  1..483
                        note = WT D1-Fc-C4 Quad-X
source                  1..483
                        mol_type = protein
                        organism = synthetic construct
SEQUENCE: 60
ARVDQTPQTI TKETGESLTI NCVLRDSHCA TSSTYWYRKK SGSTNEESIS KGGRYVETVN    60
SGSKSFSLRI NDLTVEDSGT YRCASECQYG LAEYDVYGGG TVVTVNGSGG GSGGGGSGEP   120
```

```
KSSDKTHTCP PCPAPELLGG PSVFLFPPKP KDTLMISRTP EVTCVVVDVS HEDPEVKFNW    180
YVDGVEVHNA KTKPREEQYN STYRVVSVLT VLHQDWLNGK EYKCKVSNKA LPAPIEKTIS    240
KAKGQPREPQ VYTLPPSRDE LTKNQVSLTC LVKGFYPSDI AVEWESNGQP ENNYKTTPPV    300
LDSDGSFFLY SKLTVDKSRW QQGNVFSCSV MHEALHNHYT QKSLSLSPGK GGGGSGGGGS    360
GGGGSGGGGS GAHSARVDQT PQTITKETGE SLTINCVLRD SNCGLSSTYW YRKKSGSTNE    420
ESISKGGRYV ETINEGSKSF SLRINDLTVE DSGTYRCKLS WWTQNWRCSN SDVYGGGTVV    480
TVN                                                                 483

SEQ ID NO: 61          moltype = AA   length = 107
FEATURE                Location/Qualifiers
REGION                 1..107
                       note = P3A1
source                 1..107
                       mol_type = protein
                       organism = synthetic construct
SEQUENCE: 61
TRVDQTPRTA TKETGESLTI NCVLTDTSYG LYSTSWFRKN PGTTDWERMS IGGRYVESVN    60
KGAKSFSLRI KDLTVADSAT YYCKAREARH PWLRQWYDGA GTVLTVN                  107

SEQ ID NO: 62          moltype = AA   length = 107
FEATURE                Location/Qualifiers
REGION                 1..107
                       note = P3A1 V1
source                 1..107
                       mol_type = protein
                       organism = synthetic construct
SEQUENCE: 62
TRVDQSPSSL SASVGDRVTI TCVLTDTSYG LYSTSWFRKN PGTTDWERMS IGGRYVESVN    60
KGAKSFTLTI SSLQPEDFAT YYCKAREARH PWLRQWYDGA GTKVEIK                  107

SEQ ID NO: 63          moltype = AA   length = 107
FEATURE                Location/Qualifiers
REGION                 1..107
                       note = P3A1 V4
source                 1..107
                       mol_type = protein
                       organism = synthetic construct
SEQUENCE: 63
TRVDQSPSSL SASVGDRVTI TCVLTDTSYG LYSTSWFQQK PGTTDWERMS IGGRYSGSGS    60
KGAKSFTLTI SSLQPEDFAT YYCKAREARH PWLRQWYDGA GTKVEIK                  107

SEQ ID NO: 64          moltype = AA   length = 105
FEATURE                Location/Qualifiers
REGION                 1..105
                       note = E4WT
source                 1..105
                       mol_type = protein
                       organism = synthetic construct
SEQUENCE: 64
ASVNQTPRTA TKETGESLTI NCVLTDTKYL YSTSWFRKNP GTTDWERMSI GGRYVESVNK    60
GAKSFSLRIK DLTVADSATY ICRAWTSFEE QVKDVYGAGT VLTVN                    105

SEQ ID NO: 65          moltype = AA   length = 105
FEATURE                Location/Qualifiers
REGION                 1..105
                       note = E4V1
source                 1..105
                       mol_type = protein
                       organism = synthetic construct
SEQUENCE: 65
ASVNQSPSSL SASVGDRVTI TCVLTDTKYL YSTSWFRKNP GTTDWERMSI GGRYVESVNK    60
GAKSFSLRIK DLTVADSATY ICRAWTSFEE QVKDVYGGGT KVEIK                    105

SEQ ID NO: 66          moltype = AA   length = 105
FEATURE                Location/Qualifiers
REGION                 1..105
                       note = E4V2
source                 1..105
                       mol_type = protein
                       organism = synthetic construct
SEQUENCE: 66
ASVNQSPSSL SASVGDRVTI TCVLTDTKYL YSTSWFRKNP GTTDWERMSI GGRYVESVNK    60
GAKSFTLTIS SLQPEDFATY YCRAWTSFEE QVKDVYGGGT KVEIK                    105

SEQ ID NO: 67          moltype = AA   length = 105
FEATURE                Location/Qualifiers
REGION                 1..105
                       note = E4V3
source                 1..105
```

```
                           mol_type = protein
                           organism = synthetic construct
SEQUENCE: 67
ASVNQSPSSL SASVGDRVTI TCVLTDTKYL YSTSWFRKNP GTTDWERMSI GGRFSGSGSK    60
GAKSFTLTIS SLQPEDFATY YCRAWTSFEE QVKDVYGGGT KVEIK                   105

SEQ ID NO: 68              moltype = AA  length = 105
FEATURE                    Location/Qualifiers
REGION                     1..105
                           note = E4V4
source                     1..105
                           mol_type = protein
                           organism = synthetic construct
SEQUENCE: 68
ASVNQSPSSL SASVGDRVTI TCVLTDTKYL YSTSWYQQKP GTTDWERMSI GGRYVESVNK    60
GAKSFTLTIS SLQPEDFATY YCRAWTSFEE QVKDVYGGGT KVEIK                   105

SEQ ID NO: 69              moltype = AA  length = 105
FEATURE                    Location/Qualifiers
REGION                     1..105
                           note = E4V5
source                     1..105
                           mol_type = protein
                           organism = synthetic construct
SEQUENCE: 69
ASVNQSPSSL SASVGDRVTI TCVLTDTKYL YSTSWYQQKP GTTDWERMSI GGRFSGSGSK    60
GAKSFTLTIS SLQPEDFATY YCRAWTSFEE QVKDVYGGGT KVEIK                   105

SEQ ID NO: 70              moltype = AA  length = 108
FEATURE                    Location/Qualifiers
REGION                     1..108
                           note = 78WT
source                     1..108
                           mol_type = protein
                           organism = synthetic construct
SEQUENCE: 70
TRVDQTPRTA TKETGESLTI NCVLTDTNYS LYATSWFRKN PGTTDWERMS IGGRYVESVN    60
KGAKSFSLRI KDLTVADSAT YICRAVWFPY FISDMWDVYG AGTVLTVN                108

SEQ ID NO: 71              moltype = AA  length = 108
FEATURE                    Location/Qualifiers
REGION                     1..108
                           note = 78V1
source                     1..108
                           mol_type = protein
                           organism = synthetic construct
SEQUENCE: 71
TRVDQSPSSL SASVGDRVTI TCVLTDTNYS LYATSWFRKN PGTTDWERMS IGGRYVESVN    60
KGAKSFSLRI KDLTVADSAT YICRAVWFPY FISHMWDVYG GGTKVEIK                108

SEQ ID NO: 72              moltype = AA  length = 108
FEATURE                    Location/Qualifiers
REGION                     1..108
                           note = 78V2
source                     1..108
                           mol_type = protein
                           organism = synthetic construct
SEQUENCE: 72
TRVDQSPSSL SASVGDRVTI TCVLTDTNYS LYATSWFRKN PGTTDWERMS IGGRYVESVN    60
KGAKSFTLTI SSLQPEDFAT YYCRAVWFPY FISDMWDVYG GGTKVEIK                108

SEQ ID NO: 73              moltype = AA  length = 108
FEATURE                    Location/Qualifiers
REGION                     1..108
                           note = 78V3
source                     1..108
                           mol_type = protein
                           organism = synthetic construct
SEQUENCE: 73
TRVDQSPSSL SASVGDRVTI TCVLTDTNYS LYATSWYQQK PGKTDWERMS IGGRYVESVN    60
KGAKSFTLTI SSLQPEDFAT YYCRAVWFPY FISDMWDVYG GGTKVEIK                108

SEQ ID NO: 74              moltype = AA  length = 108
FEATURE                    Location/Qualifiers
REGION                     1..108
                           note = 78V4
source                     1..108
                           mol_type = protein
                           organism = synthetic construct
```

```
SEQUENCE: 74
TRVDQSPSSL SASVGDRVTI TCVLTDTNYS LYATSWFRKN PGTTDWERMS IGGRFSGSGS    60
KGAKSFTLTI SSLQPEDFAT YYCRAVWFPY FISDMWDVYG GGTKVEIK                108

SEQ ID NO: 75           moltype = AA  length = 108
FEATURE                 Location/Qualifiers
REGION                  1..108
                        note = 78V5
source                  1..108
                        mol_type = protein
                        organism = synthetic construct
SEQUENCE: 75
TRVDQSPSSL SASVGDRVTI TCVLTDTNYS LYATSWYQQK PGKTDWERMS IGGRFSGSGS    60
KGAKSFTLTI SSLQPEDFAT YYCRAVWFPY FISDMWDVYG GGTKVEIK                108

SEQ ID NO: 76           moltype = AA  length = 105
FEATURE                 Location/Qualifiers
REGION                  1..105
                        note = E4V2B09
source                  1..105
                        mol_type = protein
                        organism = synthetic construct
SEQUENCE: 76
ASVNQSPSSL SASVGDRVTI TCVLTGTGYW YSTSWFRKNP GTSNEDRIII GGRYVESVNK    60
GTKSFTLTIS SLQPEDFATY YCRAWTSFEE QVKDVYGGGT KVEIK                   105

SEQ ID NO: 77           moltype = AA  length = 105
FEATURE                 Location/Qualifiers
REGION                  1..105
                        note = E4V2D10
source                  1..105
                        mol_type = protein
                        organism = synthetic construct
SEQUENCE: 77
ASVNQSPSSL SASVGDRVTI TCVLTGAGYW FATSWFRKNP GTSDKESISN SGRYVESVNK    60
RSMSFTLTIS SLQPEDFATY YCRAWTSFEE QVKDVYGGGT KVEIK                   105

SEQ ID NO: 78           moltype = AA  length = 105
FEATURE                 Location/Qualifiers
REGION                  1..105
                        note = E4V2F3
source                  1..105
                        mol_type = protein
                        organism = synthetic construct
SEQUENCE: 78
ASVNQSPSSL SASVGDRVTI TCVLTDTNYW YSTSWFRKNP GTTNEDRIII SGRYVESVNN    60
GPKSFTLTIS SLQPEDFATY YCRAWTSFEE QVKDVYGGGT KVEIK                   105

SEQ ID NO: 79           moltype = AA  length = 105
FEATURE                 Location/Qualifiers
REGION                  1..105
                        note = E4V2Cc8
source                  1..105
                        mol_type = protein
                        organism = synthetic construct
SEQUENCE: 79
ASVNQSPSSL SASVGDRVTI TCVLTSAGYL YATSWFRKNP GTSDKESMII GRRYVESVNN    60
RSMSFTLTIS SLQPEDFATY YCRAWTSFEE QVKDVYGGGT KVEIK                   105

SEQ ID NO: 80           moltype = AA  length = 105
FEATURE                 Location/Qualifiers
REGION                  1..105
                        note = E4V2Cc9
source                  1..105
                        mol_type = protein
                        organism = synthetic construct
SEQUENCE: 80
ASVNQSPSSL SASVGDRVTI TCVLTGTEYL YSTSWFRKNP GTPNEDRMIN GGRYVESVNK    60
GTMSFTLTIS SLQPEDFATY YCRAWTSFEE QVKDVYGGGT KVEIK                   105

SEQ ID NO: 81           moltype = AA  length = 105
FEATURE                 Location/Qualifiers
REGION                  1..105
                        note = E4V2Ee6
source                  1..105
                        mol_type = protein
                        organism = synthetic construct
SEQUENCE: 81
ASVNQSPSSL SASVGDRVTI TCVLTDTRYL YATSWFRKNP GTTNKESISN GGRYVESVNK    60
```

```
RSMSFTLTIS SLQPEDFATY YCRAWTSFEE QVKDVYGGGT KVEIK            105

SEQ ID NO: 82           moltype = AA   length = 105
FEATURE                 Location/Qualifiers
REGION                  1..105
                        note = E4V2Ee8
source                  1..105
                        mol_type = protein
                        organism = synthetic construct
SEQUENCE: 82
ASVNQSPSSL SASVGDRVTI TCVLTGASYW YSTSWFRKNP GTTDEESMSN GGRYVESVNK  60
RPMSFTLTIS SLQPEDFATY YCRAWTSFEE QVKDVYGGGT KVEIK                 105

SEQ ID NO: 83           moltype = AA   length = 105
FEATURE                 Location/Qualifiers
REGION                  1..105
                        note = E4V2Gg11
source                  1..105
                        mol_type = protein
                        organism = synthetic construct
SEQUENCE: 83
ASVNQSPSSL SASVGDRVTI TCVLTGTRYW FSTSWFRKNP GTTDEDSISN GGRYVESVNN  60
GSMSFTLTIS SLQPEDFATY YCRAWTSFEE QVKDVYGGGT KVEIK                 105

SEQ ID NO: 84           moltype = AA   length = 112
FEATURE                 Location/Qualifiers
REGION                  1..112
                        note = D3WT
source                  1..112
                        mol_type = protein
                        organism = synthetic construct
SEQUENCE: 84
ASVNQTPRTA TKETGESLTI NCVLTDTSYG LYSTSWFRKN PGTTDWERMS IGGRYVESVN  60
KRAKSFSLRI KDLTVADSAT YYCKAQSGMA ISTGSGHGYN WYDGAGTVLT VN         112

SEQ ID NO: 85           moltype = AA   length = 112
FEATURE                 Location/Qualifiers
REGION                  1..112
                        note = D3WT V1
source                  1..112
                        mol_type = protein
                        organism = synthetic construct
SEQUENCE: 85
ASVNQSPSSL SASVGDRVTI TCVLTDTSYG LYSTSWFRKN PGTTDWERMS IGGRYVESVN  60
KRAKSFSLRI KDLTVADSAT YYCKAQSGMA ISTGSGHGYN WYDGAGTKVE IK         112

SEQ ID NO: 86           moltype = AA   length = 112
FEATURE                 Location/Qualifiers
REGION                  1..112
                        note = D3WT V2
source                  1..112
                        mol_type = protein
                        organism = synthetic construct
SEQUENCE: 86
ASVNQSPSSL SASVGDRVTI TCVLTDTSYG LYSTSWFRKN PGTTDWERMS IGGRYVESVN  60
KRAKSFTLTI SSLQPEDFAT YYCKAQSGMA ISTGSGHGYN WYDGAGTKVE IK         112

SEQ ID NO: 87           moltype = AA   length = 112
FEATURE                 Location/Qualifiers
REGION                  1..112
                        note = D3WT V4
source                  1..112
                        mol_type = protein
                        organism = synthetic construct
SEQUENCE: 87
ASVNQSPSSL SASVGDRVTI TCVLTDTSYG LYSTSWYQQK PGTTDWERMS IGGRYVESVN  60
KRAKSFTLTI SSLQPEDFAT YYCKAQSGMA ISTGSGHGYN WYDGAGTKVE IK         112

SEQ ID NO: 88           moltype = AA   length = 112
FEATURE                 Location/Qualifiers
REGION                  1..112
                        note = D3WT V5
source                  1..112
                        mol_type = protein
                        organism = synthetic construct
SEQUENCE: 88
ASVNQSPSSL SASVGDRVTI TCVLTDTSYG LYSTSWYQQK PGTTDWERMS IGGRFSGSGS  60
KRAKSFTLTI SSLQPEDFAT YYCKAQSGMA ISTGSGHGYN WYDGAGTKVE IK         112
```

```
SEQ ID NO: 89           moltype = AA   length = 25
FEATURE                 Location/Qualifiers
REGION                  1..25
                        note = D3V2 FW1
source                  1..25
                        mol_type = protein
                        organism = synthetic construct
SEQUENCE: 89
ASVNQSPSSL SASVGDRVTI TCVLT                                        25

SEQ ID NO: 90           moltype = AA   length = 8
FEATURE                 Location/Qualifiers
REGION                  1..8
                        note = D3V2 CDR1
source                  1..8
                        mol_type = protein
                        organism = synthetic construct
SEQUENCE: 90
DTSYGLYS                                                            8

SEQ ID NO: 91           moltype = AA   length = 10
FEATURE                 Location/Qualifiers
REGION                  1..10
                        note = D3V2 FW2
source                  1..10
                        mol_type = protein
                        organism = synthetic construct
SEQUENCE: 91
TSWFRKNPGT                                                         10

SEQ ID NO: 92           moltype = AA   length = 9
FEATURE                 Location/Qualifiers
REGION                  1..9
                        note = D3V2 HV2
source                  1..9
                        mol_type = protein
                        organism = synthetic construct
SEQUENCE: 92
TDWERMSIG                                                           9

SEQ ID NO: 93           moltype = AA   length = 8
FEATURE                 Location/Qualifiers
REGION                  1..8
                        note = D3V2 FW3a
source                  1..8
                        mol_type = protein
                        organism = synthetic construct
SEQUENCE: 93
GRYVESVN                                                            8

SEQ ID NO: 94           moltype = AA   length = 5
FEATURE                 Location/Qualifiers
REGION                  1..5
                        note = D3V2 HV4
source                  1..5
                        mol_type = protein
                        organism = synthetic construct
SEQUENCE: 94
KRAKS                                                               5

SEQ ID NO: 95           moltype = AA   length = 20
FEATURE                 Location/Qualifiers
REGION                  1..20
                        note = D3V2 FW3b
source                  1..20
                        mol_type = protein
                        organism = synthetic construct
SEQUENCE: 95
FTLTISSLQP EDFATYYCKA                                              20

SEQ ID NO: 96           moltype = AA   length = 17
FEATURE                 Location/Qualifiers
REGION                  1..17
                        note = D3V2 CDR3
source                  1..17
                        mol_type = protein
                        organism = synthetic construct
SEQUENCE: 96
QSGMAISTGS GHGYNWY                                                 17
```

```
SEQ ID NO: 97           moltype = AA  length = 10
FEATURE                 Location/Qualifiers
REGION                  1..10
                        note = D3V2 FW4
source                  1..10
                        mol_type = protein
                        organism = synthetic construct
SEQUENCE: 97
DGAGTKVEIK                                                                10

SEQ ID NO: 98           moltype = AA  length = 228
FEATURE                 Location/Qualifiers
REGION                  1..228
                        note = D3 V2 PAN3 F11
source                  1..228
                        mol_type = protein
                        organism = synthetic construct
SEQUENCE: 98
ASVNQSPSSL SASVGDRVTI TCVLTDTNYG LYATSWFRKN PGTSNEDRII ISGRYVESVN          60
KRTKSFTLTI SSLQPEDFAT YYCKAQSGMA ISTGSGHGYN WYDGAGTKVE IKQASGAAAA         120
PSVFIFPPSD EQLKSGTASV VCLLNNFYPR EAKVQWKVDN ALQSGNSQES VTEQDSKDST         180
YSLSSTLTLS KADYEKHKVY ACEVTHQGLS SPVTKSFNRG ESHHHHHH                      228

SEQ ID NO: 99           moltype = AA  length = 228
FEATURE                 Location/Qualifiers
REGION                  1..228
                        note = D3 V2 PAN3 E08
source                  1..228
                        mol_type = protein
                        organism = synthetic construct
SEQUENCE: 99
ASVNQSPSSL SASVGDRVTI TCVLTDTRYG LYSTSWFRKN PGTTDKERIS IGGRYVESVN          60
KRTKSFTLTI SSLQPEDFAT YYCKAQSGMA ISTGSGHGYN WYDGAGTKVE IKQASGAAAA         120
PSVFIFPPSD EQLKSGTASV VCLLNNFYPR EAKVQWKVDN ALQSGNSQES VTEQDSKDST         180
YSLSSTLTLS KADYEKHKVY ACEVTHQGLS SPVTKSFNRG ESHHHHHH                      228

SEQ ID NO: 100          moltype = AA  length = 228
FEATURE                 Location/Qualifiers
REGION                  1..228
                        note = D3 V2 PAN F01
source                  1..228
                        mol_type = protein
                        organism = synthetic construct
SEQUENCE: 100
ASVNQSPSSL SASVGDRVTI TCVLTDTKYG LYSTSWFRKN PGTTDKERIS IGGRYVESVN          60
KRTKSFTLTI SSLQPEDFAT YYCKAQSGMA ISTGSGHGYN WYDGAGTKVE IKQASGAAAA         120
PSVFIFPPSD EQLKSGTASV VCLLNNFYPR EAKVQWKVDN ALQSGNSQES VTEQDSKDST         180
YSLSSTLTLS KADYEKHKVY ACEVTHQGLS SPVTKSFNRG ESHHHHHH                      228

SEQ ID NO: 101          moltype = AA  length = 228
FEATURE                 Location/Qualifiers
REGION                  1..228
                        note = D3 V2 PAN G02
source                  1..228
                        mol_type = protein
                        organism = synthetic construct
SEQUENCE: 101
ASVNQSPSSL SASVGDRVTI TCVLTDTNYG LYATSWFRKN PGTTDEERMS IGGRYVESVN          60
KRSKSFTLTI SSLQPEDFAT YYCKAQSGMA ISTGSGHGYN WYDGAGTKVE IKQASGAAAA         120
PSVFIFPPSD EQLKSGTASV VCLLNNFYPR EAKVQWKVDN ALQSGNSQES VTEQDSKDST         180
YSLSSTLTLS KADYEKHKVY ACEVTHQGLS SPVTKSFNRG ESHHHHHH                      228
```

FAST-TRACK HUMANISATION OF SPECIFIC BINDING MOLECULES

CROSS-REFERENCE TO RELATED APPLICATIONS

This application is a continuation of International Appln. PCT/EP2021/086492, filed on Dec. 17, 2021, which itself claims the benefit of GB Appln. 2020152.1 filed on Dec. 18, 2020, the contents of each of which are incorporated herein by reference in their entireties for all purposes.

REFERENCE TO SEQUENCE LISTING SUBMITTED ELECTRONICALLY

The contents of the electronic sequence listing (17932449_SL.xml; Size: 149,029 bytes; and Date of Creation: Oct. 18, 2023) is herein incorporated by reference in its entirety.

The present invention relates to a synthetic library of humanised antigen specific binding molecules derived from a member of a species in the Elasmobranchii subclass, processes for the production thereof and specific antigen specific binding molecules isolated from said library. The present invention also relates to the multi-domain specific binding molecules comprising humanised Ig-like Novel Antigen Receptor variable domains (VNARs). Specific binding domains that bind to Tumour Necrosis Factor alpha (TNFα) are also provided.

The invention generally relates to libraries of humanised antigen specific antigen binding molecules. The libraries include a plurality of different humanised antigen specific antigen binding molecules, including domains and/or fragments thereof, generated by creating diversity in both the CDR regions and framework regions and humanising the sequence of at least one framework region. In particular, diversity in CDR regions is designed to maximize the diversity while minimizing the structural perturbations of the VNAR sequences and domains of the antigen specific antigen binding molecules of the invention.

Such libraries provide combinatorial libraries useful for, for example, selecting and/or screening for synthetic VNAR clones with desirable activities such as binding affinities and avidities. These libraries are useful for identifying sequences that are capable of interacting with any of a wide variety of target antigens. For example, libraries comprising diversified VNAR polypeptides of the invention displayed on phage are particularly useful for, and provide a high throughput, efficient and automatable systems of, selecting and/or screening for antigen binding molecules of interest. The methods of the invention are designed to provide high affinity binders to target antigens with minimal changes to a source ortemplate molecule and provide for good production yields when the antibody or antigens binding fragments are produced in cell culture.

WO 2014/173959 describes a method for the production of a library of antigen specific antigen binding molecules, derived from RNA isolated from species in the Elasmobranchii subclass. Such libraries are useful to effectively source potential VNAR therapeutics for any given target. The usefulness of such libraries is based on the unexpected diversity, affinity, specificity and efficacy of VNARs isolated from a library created from two or more naturally occurring VNAR sequences from different isotypes within the same species and different isotypes across different Elasmobranchii species. The present inventors have now created libraries that incorporate humanised sequences for at least one framework region, contrary to the teaching of WO 2014/173959 relying on the advantages of using two or more naturally occurring VNAR sequences. The libraries of the invention allow the sourcing of improved potential VNAR therapeutics for any given target, since the potential VNAR therapeutics are already humanised. This allows early, efficient and high throughput testing of humanised potential VNAR therapeutics for any given target in the confidence the relevance of the testing data will not be diminished by the need to subsequently humanise (and re-test) the potential VNAR therapeutic.

The inventors have also identified multi-domain antigen specific antigen binding molecules with advantageous properties where one framework region is humanised while another framework region retains a sequence corresponding to a framework region from a member of a species in the Elasmobranchii subclass. Surprisingly, the inventors show the advantageous properties are abolished when a particular framework region (FW1) retains a sequence corresponding to a framework region from a member of a species in the Elasmobranchii subclass with another particular framework region (FW4) humanised, but in contrast are maintained when a FW1 is humanised and FW4 retains a sequence corresponding to a framework region from a member of a species in the Elasmobranchii subclass.

SUMMARY OF THE INVENTION

According to a first aspect, the invention provides a method for the production of a library of humanised antigen specific antigen binding molecules having a peptide domain structure represented by the following formula (I):

FW1-CDR1-FW2-HV2-FW3a-HV4-FW3b-CDR3-FW4 comprising
(1) amplifying DNA sequences encoding two or more contiguous peptide domains of FW1-CDR1-FW2-HV2-FW3a-HV4-FW3b-CDR3-FW4, wherein said two or more contiguous peptide domains when ligated encode an antigen specific antigen binding molecule of formula (I), in the presence of a plurality of heterologous oligomers complementary to CDR1 or CDR3 domains, to form a plurality of amplified DNA sequences encoding an antigen specific antigen binding molecule of formula (I) wherein FW1 comprises one or more humanised sequences according to –/D A/I/T S/Q/R V/M N/T/D Q S P S S L S A S V G D R V T I T C V L/V T/R D/G T/A/S (SEQ ID NO: 1);
(2) ligating together said amplified DNA sequences encoding two or more contiguous peptide domains to form DNA sequences encoding an antigen specific binding molecule having the peptide domain structure of formula (I);
(3) cloning the ligated DNA obtained in (2) into a display vector; and
(4) transforming a host with said display vector to produce a library of said antigen specific antigen binding molecules.

According to a second aspect of the invention, there is provided a process for the production of a humanised antigen specific antigen binding molecule, comprising
(1) selecting desired clones from the library prepared according to a method of any preceding claim;
(2) isolating and purifying the humanised antigen specific antigen binding molecules from these clones;

(3) cloning the DNA sequences encoding the humanised antigen specific antigen binding molecules into an expression vector; and
(4) transforming a host to allow expression of the expression vector.

According to a third aspect of the invention, there is provided a method for the production of a humanised antigen specific antigen binding molecule having a peptide domain structure represented by the following formula (I):

FW1-CDR1-FW2-HV2-FW3a-HV4-FW3b-CDR3-FW4 comprising
(1) amplifying DNA sequences encoding two or more contiguous peptide domains of FW1-CDR1-FW2-HV2-FW3a-HV4-FW3b-CDR3-FW4, wherein said two or more contiguous peptide domains when ligated encode an antigen specific antigen binding molecule of formula (I), in the presence of a plurality of heterologous oligomers complementary to CDR1 or CDR3 domains, to form a plurality of amplified DNA sequences encoding an antigen specific antigen binding molecule of formula (I) wherein FW1 comprises one or more humanised sequences according to –/D A/I/T S/Q/R V/M N/T/D Q S P S S L S A S V G D R V T I T C V L/V T/R D/G T/A/S (SEQ ID NO: 1)
(2) ligating together said amplified DNA sequences encoding two or more contiguous peptide domains to form DNA sequences encoding an antigen specific binding molecule having the peptide domain structure of formula (I);
(3) cloning the ligated DNA obtained in (2) into a display vector; and
(4) transforming a host with said display vector to produce a library of said antigen specific antigen binding molecules;
(5) selecting a desired clone from the library;
(6) isolating and purifying the antigen specific antigen binding molecule from the clone;
(7) cloning the DNA sequences encoding the antigen specific antigen binding molecule into an expression vector; and
(8) transforming a host to allow expression of the expression vector.

According to a fourth aspect of the invention, there is provided a multi-domain antigen specific antigen binding molecule comprising two or more VNAR domains, wherein each VNAR domain comprises an amino acid sequence having a peptide domain structure represented by the following formula (I):

FW1-CDR1-FW2-HV2-FW3a-HV4-FW3b-CDR3-FW4 wherein FW1 of at least one VNAR binding domain comprises a humanised sequence according to –/D A/I/T S/Q/R V/M N/T/D Q S P S S L S A S V G D R V T I T C V L/V T/R D/G T/A/S (SEQ ID NO: 1)
and wherein FW4 of at least one VNAR domain comprises a sequence corresponding to FW4 from a member of a species in the Elasmobranchii subclass, or an amino acid sequence with either
(i) at least 70% identity thereto, or
(ii) one, two, or three amino acid substitutions relative thereto.

According to a fifth aspect of the invention, there is provided an isolated nucleic acid comprising a polynucleotide sequence that encodes a multi-domain antigen specific antigen binding molecule according to the fourth aspect of the invention.

According to a sixth aspect of the invention, there is provided a method for preparing a multi-domain antigen specific antigen binding molecule, comprising cultivating or maintaining a host cell comprising the polynucleotide of the fifth aspect of the invention under conditions such that said host cell produces the multi-domain antigen specific antigen binding molecule, optionally further comprising isolating the multi-domain antigen specific antigen binding molecule.

According to a seventh aspect of the invention, there is provided a pharmaceutical composition comprising the multi-domain antigen specific binding molecule of the fourth aspect of the invention and optionally at least one pharmaceutically acceptable carrier.

According to a further aspect of the invention, there is provided a pharmaceutical composition of the previous aspect for use in medicine. Such uses include methods for the treatment of a disease associated with the interaction between the target antigen of the binding domain of the invention and its ligand partner(s) through administration of a therapeutically effective dose of a pharmaceutical composition of the invention as defined above. The composition may comprise at least one multi-domain specific binding molecule of the invention, or a combination of such molecules.

In accordance with this aspect of the invention, there is provided a composition for use in the manufacture of a medicament for the treatment of a disease associated with the interaction between target antigen of the binding domain of the invention and its ligand partner(s).

Such compositions may comprise a further pharmaceutically active agent as indicated. The additional agents may be therapeutic compounds, e.g. anti-inflammatory drugs, cytotoxic agents, cytostatic agents or antibiotics. Such additional agents may be present in a form suitable for administration to patient in need thereof and such administration may be simultaneous, separate or sequential. The components may be prepared in the form of a kit which may comprise instructions as appropriate.

According to the invention, there is provided a multi-domain specific binding molecule of the invention for use in medicine. This aspect of the invention therefore extends to the use of such of a multi-domain binding molecule of the invention in the manufacture of a medicament for the treatment of a disease in a patient in need thereof. Such uses also embrace methods of treatment of diseases in patients in need of treatment comprising administration to the patient of a therapeutically effective dosage of a pharmaceutical composition as defined herein comprising a multi-domain binding molecule of the invention.

In a further aspect the present invention provides a method for treating a condition mediated by TNFα, the method comprising the administration of a therapeutically effective amount of a composition of the invention that specifically binds to TNFα.

Figure 2:
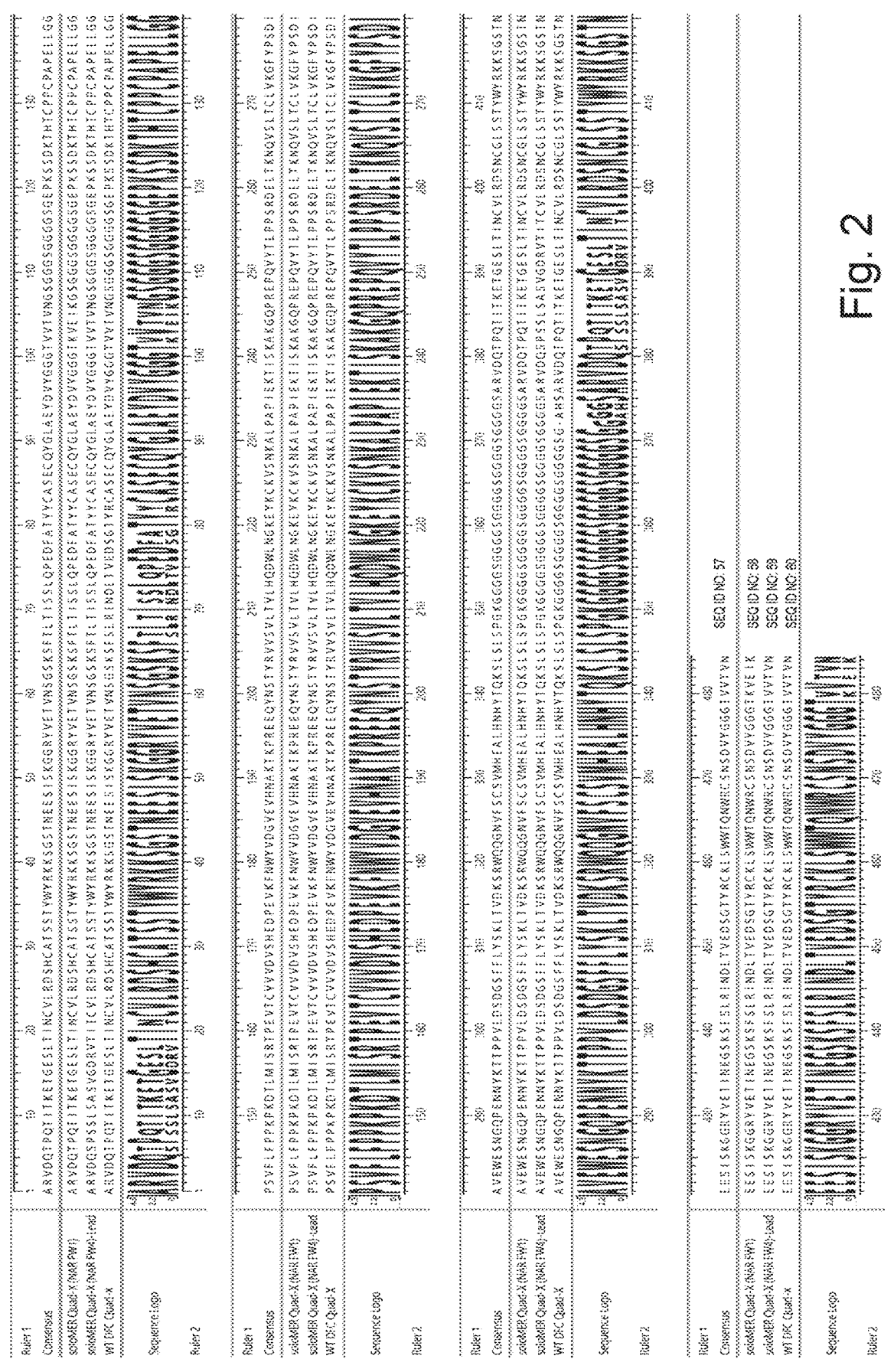

Reference is made to a number of Figures as follows:
FIG. 1. Humanisation illustrated by incorporating human residues into anti-TNF VNAR domains (D1 and C4) using DPK9, the human antibody light chain, as a template.
FIG. 2. Alignment of modified D1-huFc-C4 soloMER Quad-X constructs with restored VNAR FW1 or FW4.
FIG. 3. SDS-PAGE of reduced soloMER Quad-X variants. SoioMER Quad-X VNAR FW1 did not show expression in HEK293 cells, however soloMER Quad-X VNAR FW4 showed significant protein expression. Therefore, this format was taken forward for further characterisation and functional assessment in comparison with the native VNAR Quad-X (also referred to as WT Quad-X).

Figure 4A:
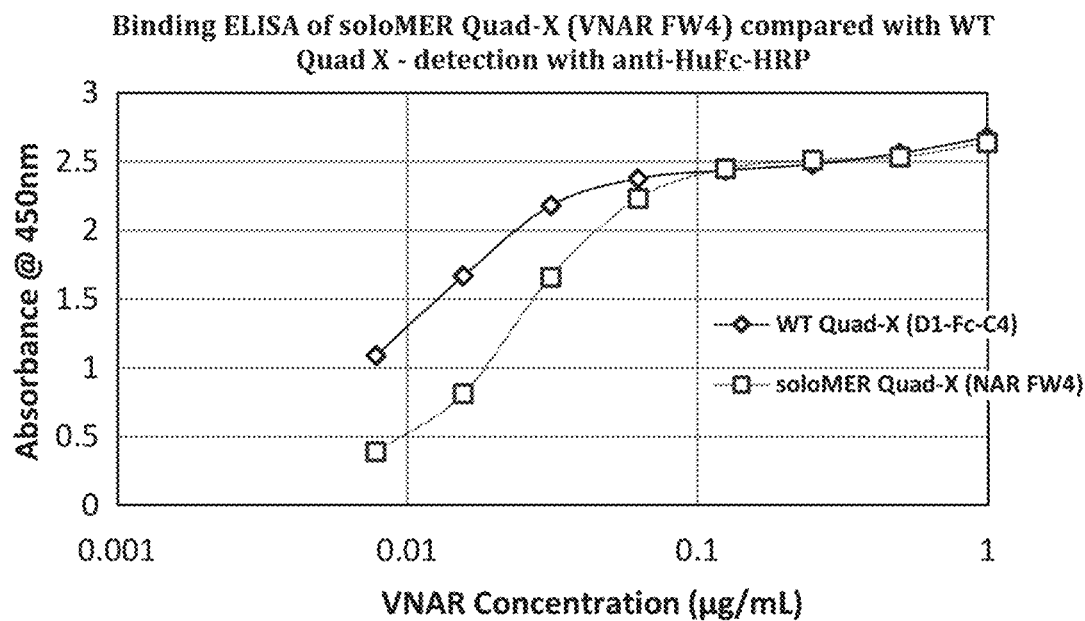
Figure 4B:
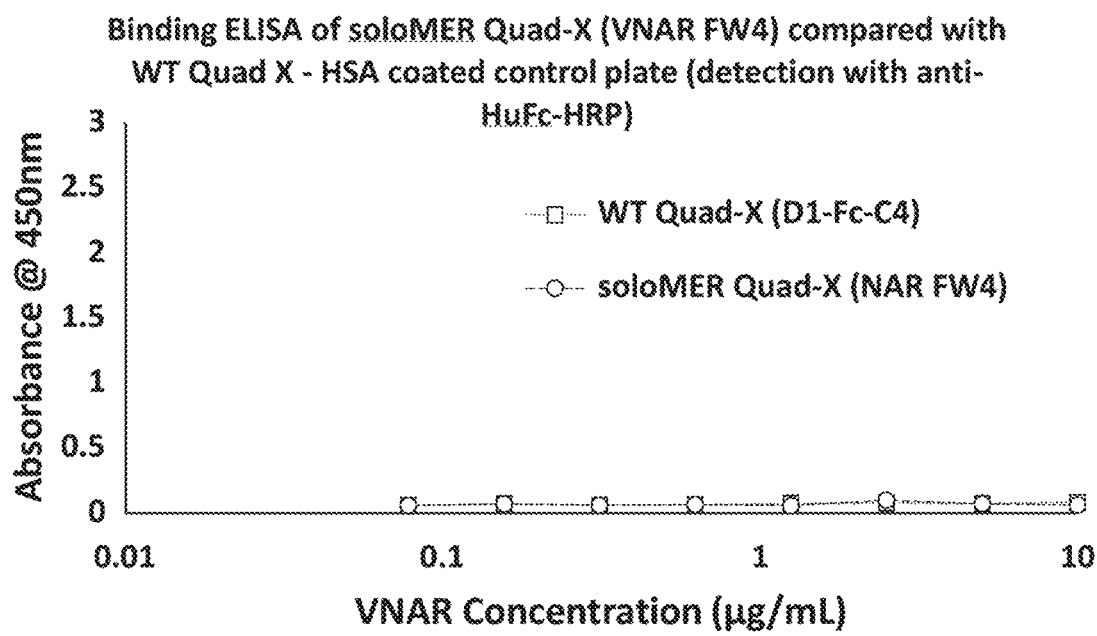

FIG. 4A-B. Binding ELISA of the soloMER Quad-X (VNAR FW4) in comparison with the native Quad-X. In this head-to-head target binding comparison, both the soloMER Quad-X (VNAR FW4) and native Quad-X showed comparable functionality recognising TNFα (FIG. 4A) and not recognising Human Serurm Albumin (FIG. 4B).

Figure 5:
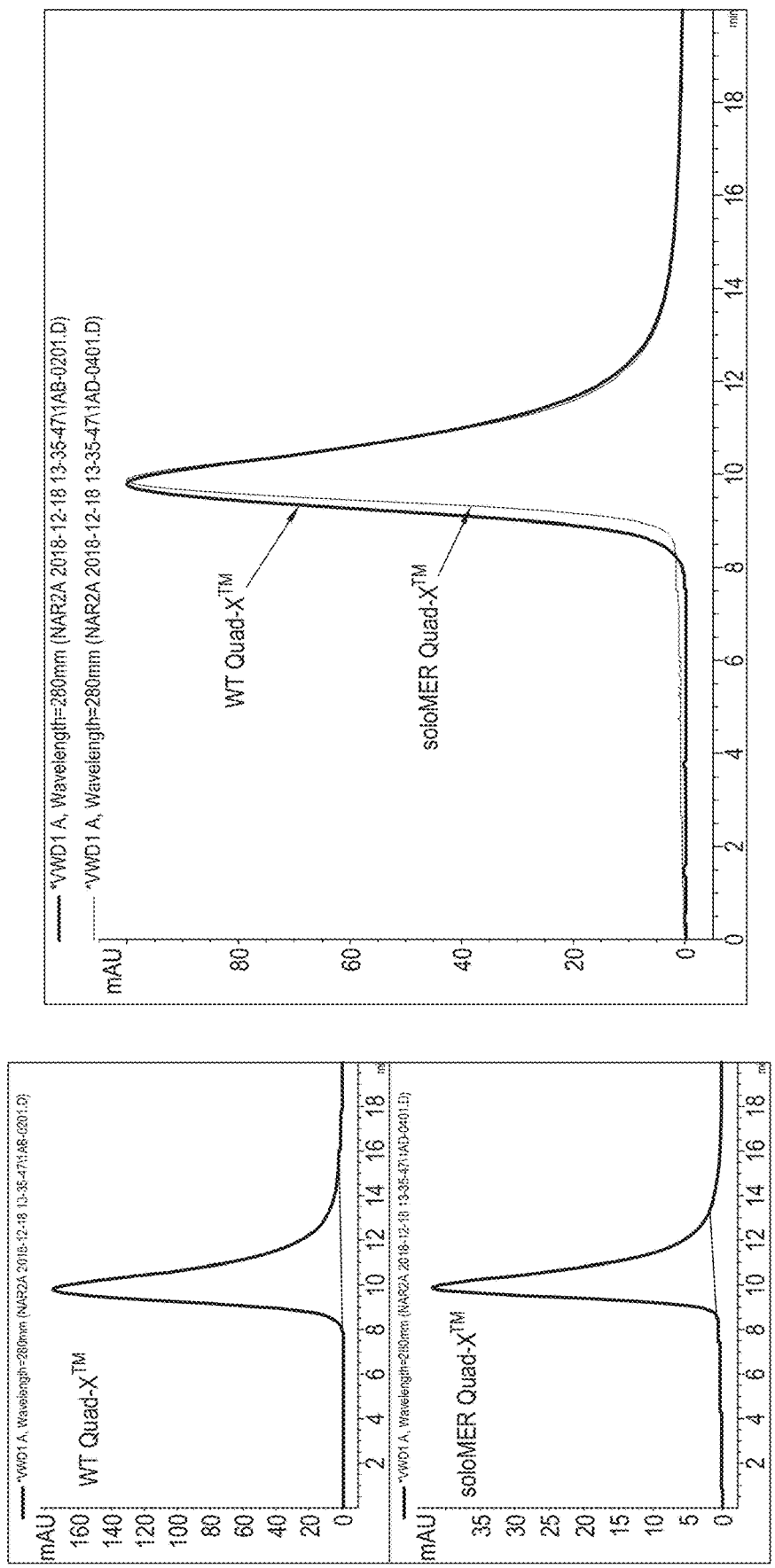

FIG. 5. Analytical size exclusion chromatography (SEC) of soloMER (soloMER VNAR FW4) and native Quad-X domains, showing SEC traces as individual peaks and overlaid. The SEC data confirms monomericity and similarity of the domains biochemical behaviour with no evidence of aggregation or instability.

Figure 6:
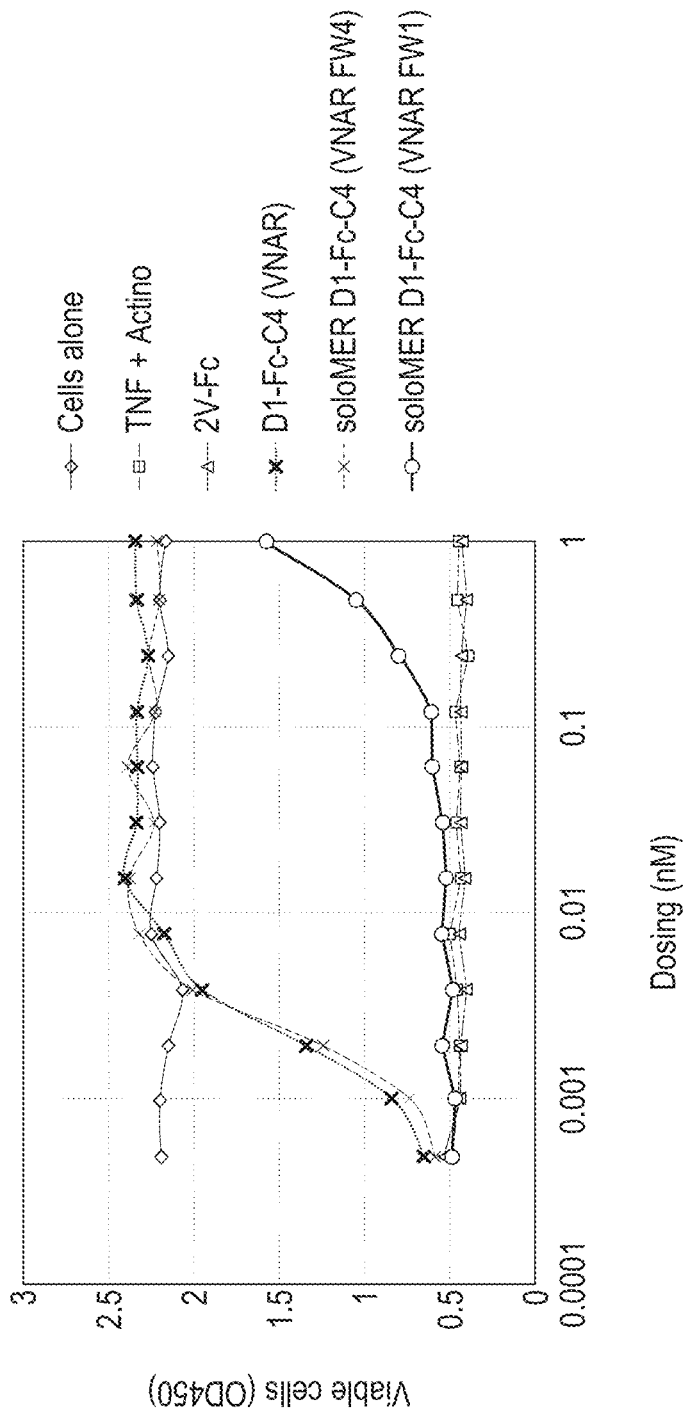

FIG. 6. Neutralisation of 0.3 ng/mL (LD80) hTNF-alpha induced cytotoxicity in L929 cells. The in vitro human TNF-alpha neutralisation assay, it was demonstrated that both the native WT Quad-X (D1-Fc-C4 VNAR) and the soloMER Quad-X (also known as the soloMER Quad-X VNAR FW4) showed an identical capacity to neutralise the cytotoxic effect of human TNF-alpha on mouse fibrosarcoma cell line (L929 cells). The achieved ND50 values for the native and soloMER Quad-X VNAR FW4 are 0.002 nM and 0.0017 nM, respectively.

Figure 7:
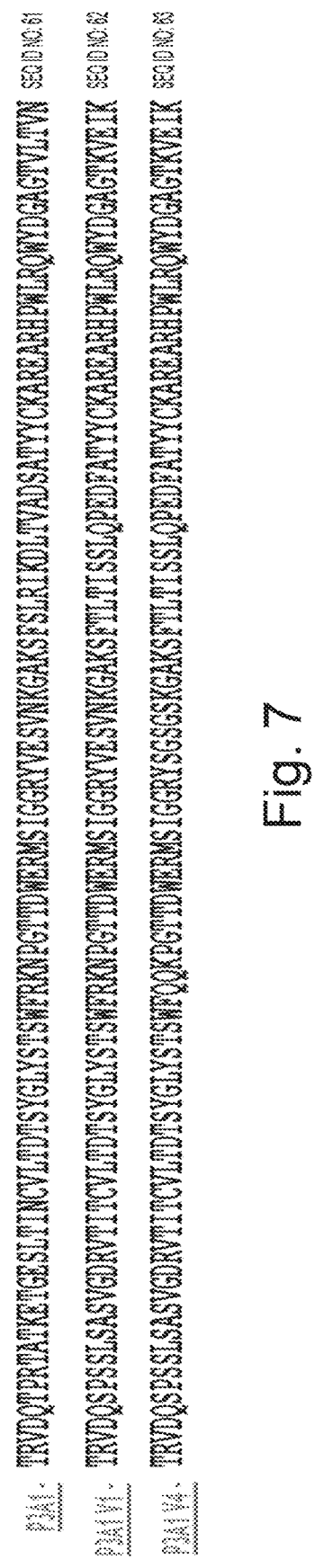

FIG. 7. Several humanised variants (V1 to V6) of the anti-ROR1 VNAR P3A1 were designed, synthesised as dimers (2×P3A1 VNAR variants joined with a short peptide linker and containing a HisMyc detection tag); sequences confirmed as correct and cloned into a suitable bacterial expression vector. See also Table 4. Constructs were expressed as dimers with HisMyc tags and as intein fusions.

Figure 8:
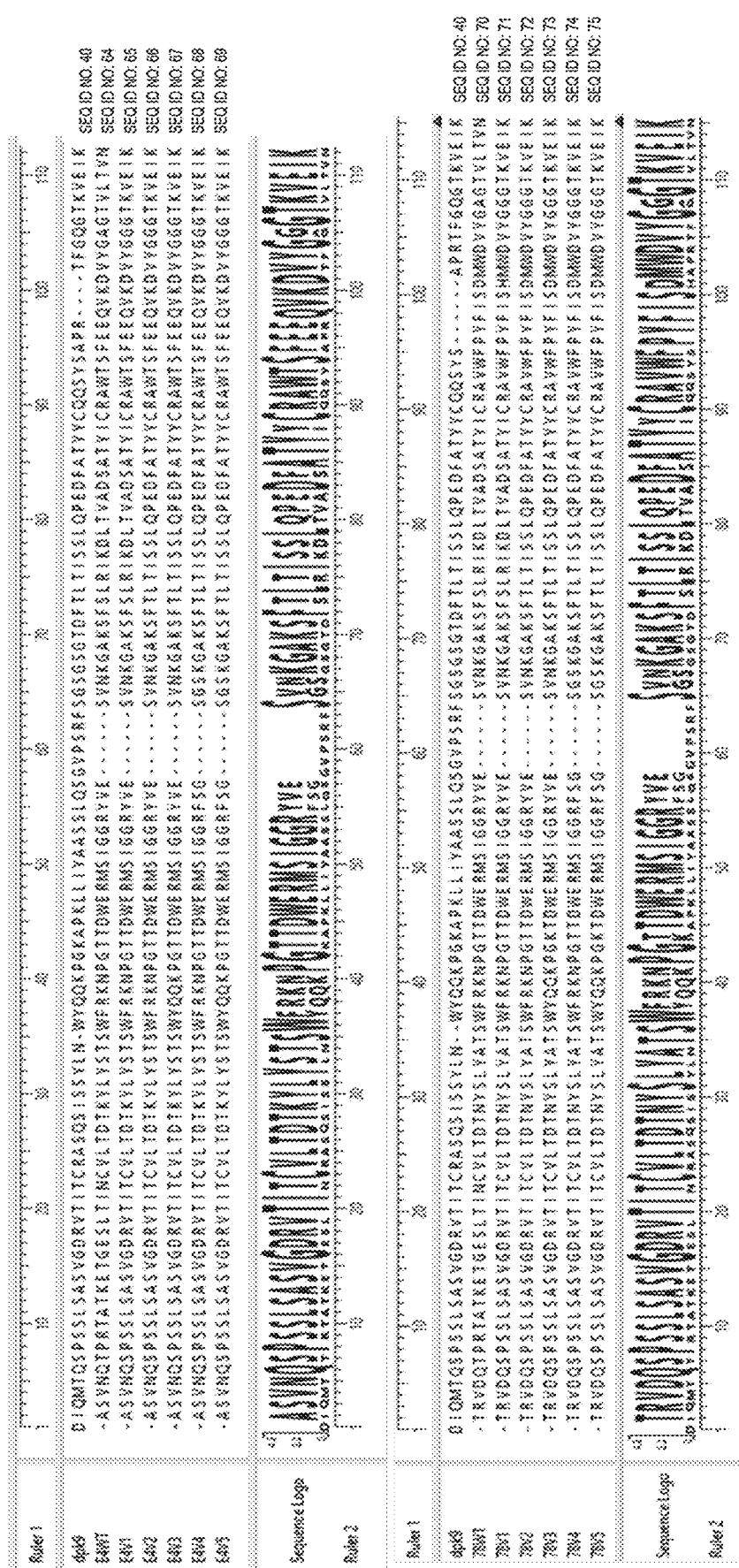

FIG. 8. Sequence alignment illustrating the humanised variants of VNAR E4 and 78. The human Ig family DPK9 sequence template utilised for the humanisation is depicted above the native (WT) anti-DLL4 VNAR sequences. The alignment illustrates the human residues from the human germline Vk1 sequence, DPK9 applied in the humanisation and the extent of increasing percentage of human residue grafting from soloMER-V1 to V5.

Figure 9:
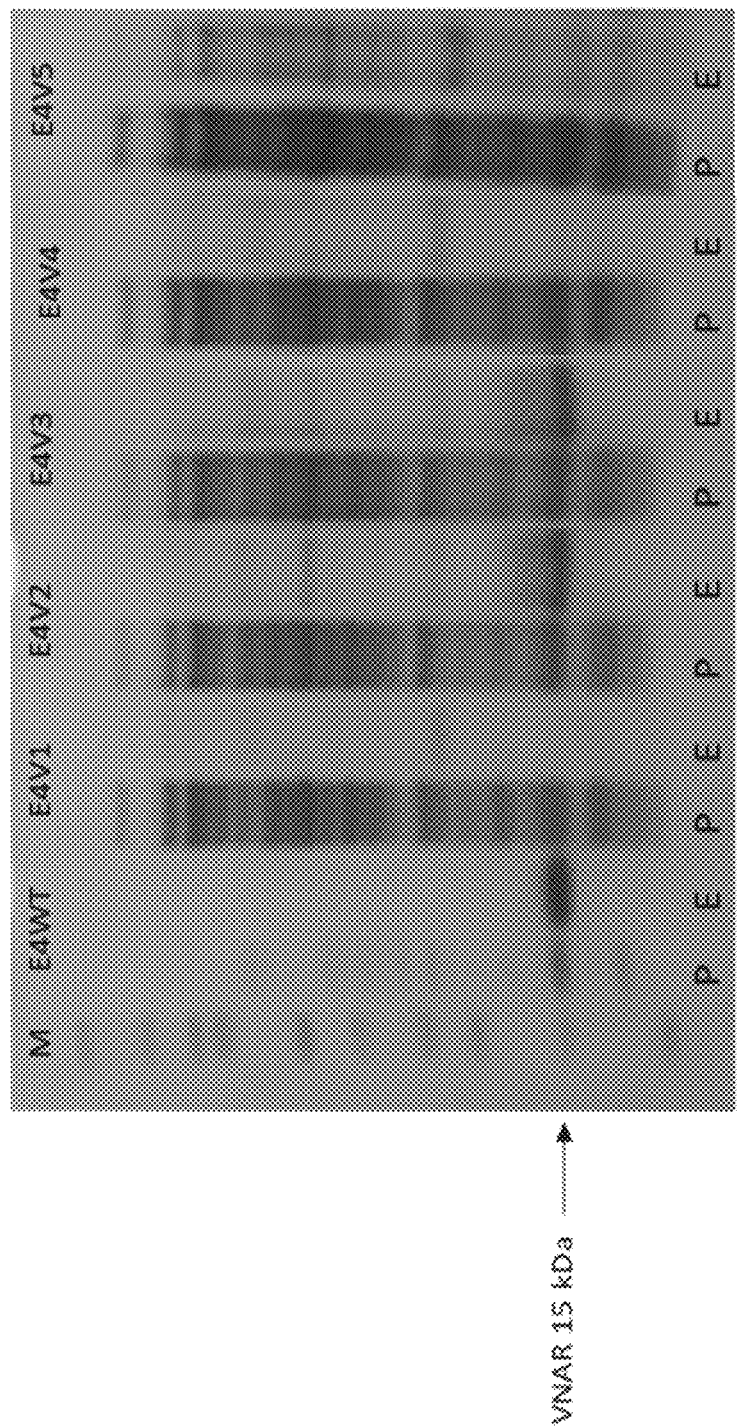

FIG. 9. SDS-PAGE of reduced soloMER variants for E4 clone; M represents the multi-colour protein marker.

Figure 10:
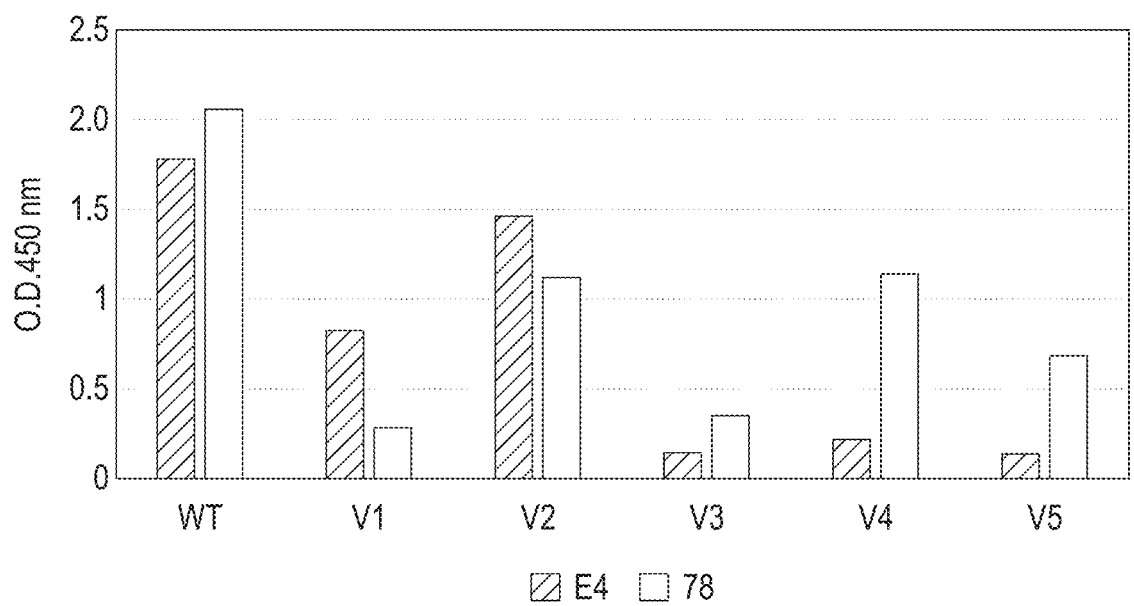

FIG. 10. Binding ELISA of the expressed and purified soloMER E4 and 78 variants against 1 μg/mL hDLL4-Fc coated ELISA plates. The best variants identified from these initial functional characterisations of the soloMER E4 and 78 variants were E4-V2 and 78-V2 and 78-V4 although each of the frameworks showed some level of functional binding and particularly for the 78 clone variants.

FIG. 11. E4-V2. Following the cloning of the library 96 sequences from each library (E4 and 78 parental sequences) were analysed and both libraries displayed greater than 90% correctness that is full sequences and different sequences from each other. The total library sizes (unique clones) were estimated to be approximately 1×109 clones.

Figure 12:
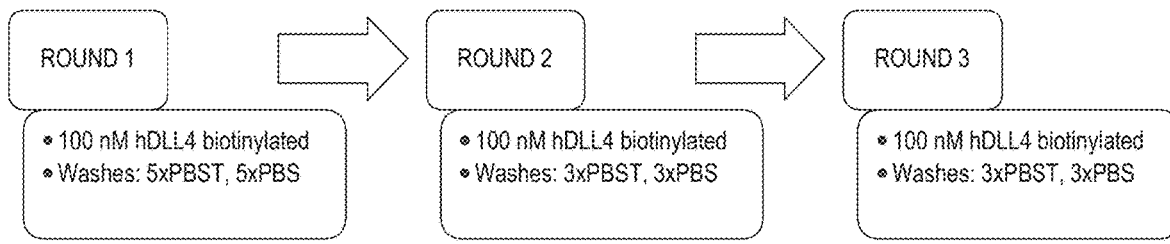

FIG. 12. E4-V2 humanised library panning strategy showing the concentration of DLL4 antigen and washing steps used (phospate buffered saline with or without tween) used at each round of panning.

Figure 13:
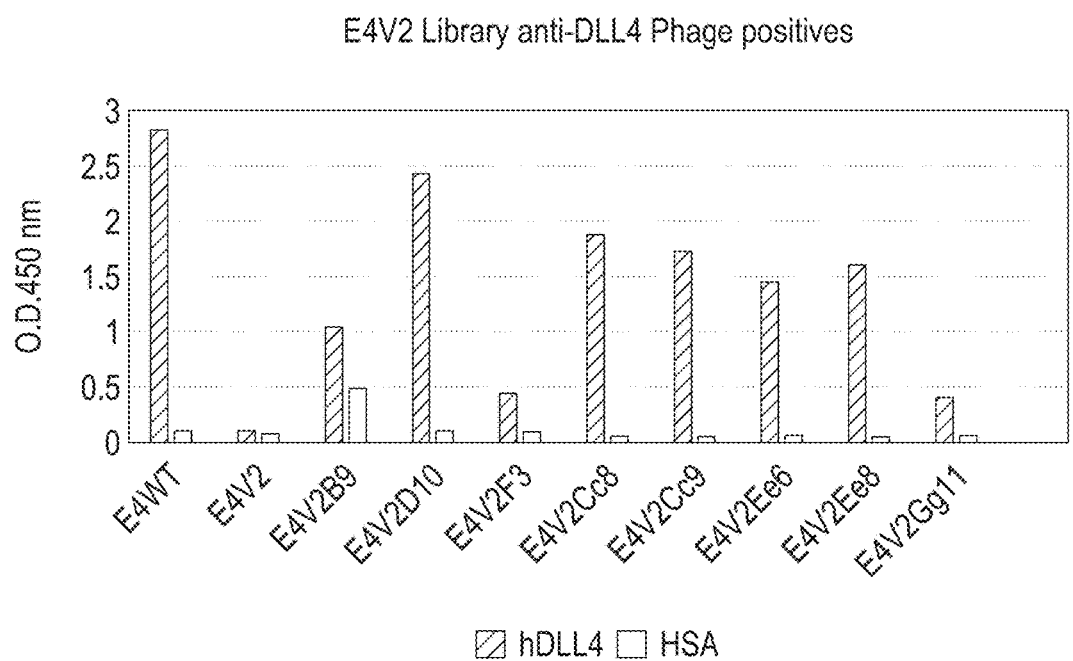

FIG. 13. E4V2 library anti-DLL4 Phage positives. The binding of the different clones was compared with the Wt DLL4 VNAR and V2 humanised parental framework and specificity confirmed by the lack of binding to Human Serum Albumin (HSA).

Figure 14:
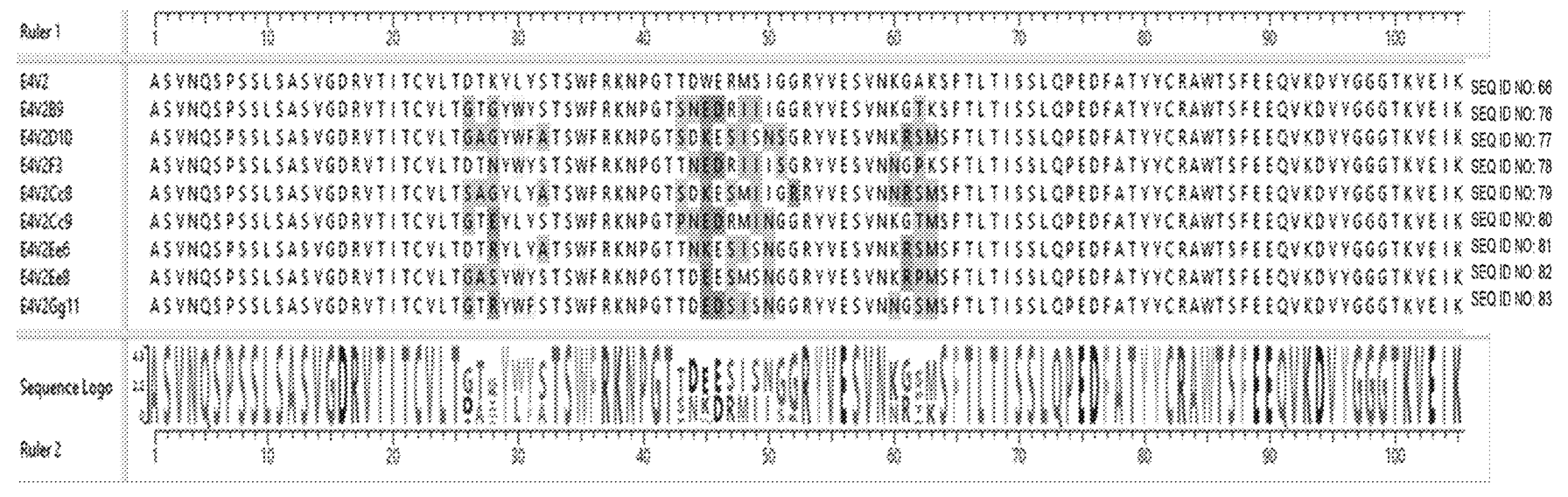

FIG. 14. Sequence analysis of anti-DLL4 phage binders derived from the libraries after selections.

FIG. 15. Several humanised variants of D3 were synthesised (V1, V2, V4, V5), sequences confirmed as correct and cloned into a suitable bacterial expression vector.

FIG. 16. Controlled mutagenesis in CDR1, HV2 and HV4, and in vitro affinity maturation against human ROR1 (hROR1) protein. Sequence and loop library design of D3V2:CDR1 diversity results in 488 combinations, HV2 diversity results in 768 combinations and HV4 diversity results in 24 combinations.

Figure 17:
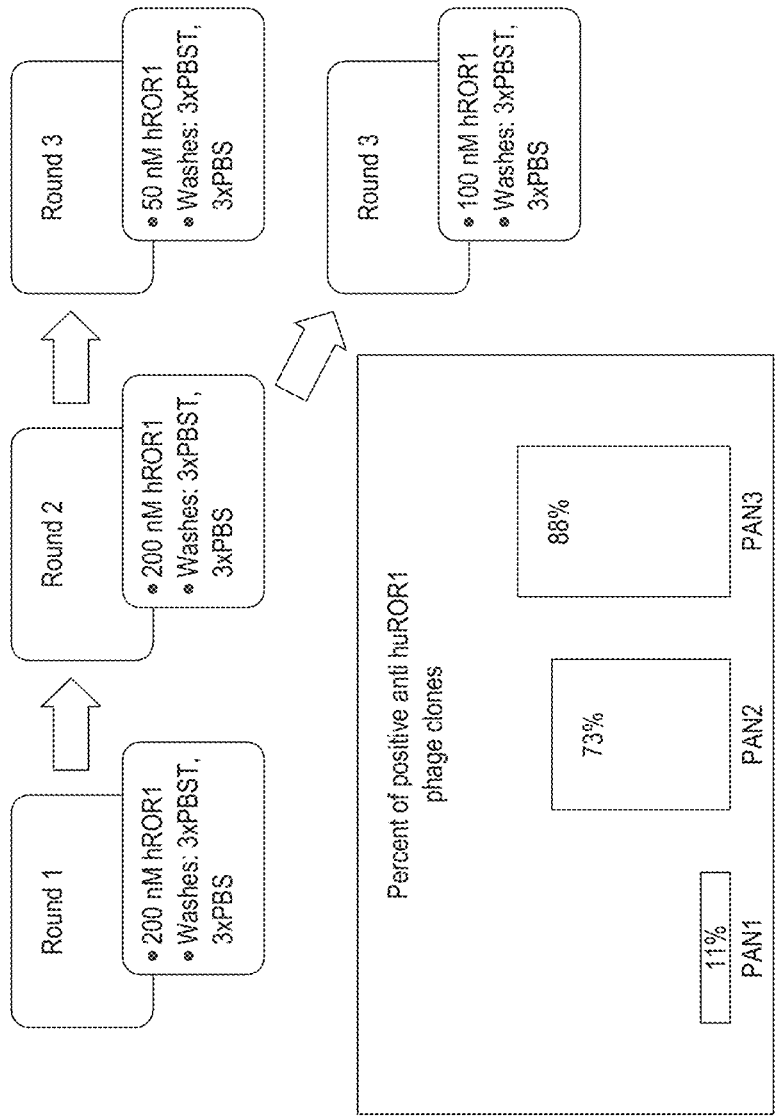

FIG. 17. Screening of soloMER library for antigen specific VNAR sequences. Selection strategy. Recombinant human ROR1 protein was used for selections and screening of the D3V2 soloMER library. To isolate ROR1 specific soloMERs biotinylated antigen was pre-decorated on streptavidin-coated beads and 3 rounds of panning with low stringency (200 nM antigen reducing to 50 nM in panning round three) were carried out. Antigen specific phage was detected by ELISA of phage monoclonals and the percentage of antigen specific phage enriched from PAN1 (11%) to PAN 3 (88%).

FIG. 18. Humanised sequences of the four best binding humanised anti-ROR1 soloMER clones. See also Table 6.

DETAILED DESCRIPTION OF THE INVENTION

The methods and compositions of the invention are useful for identifying novel antigen specific antigen binding molecules that can be used therapeutically or as reagents.

According to a first aspect, the invention provides a method for the production of a library of humanised antigen specific antigen binding molecules having a peptide domain structure represented by the following formula (I):

FW1-CDR1-FW2-HV2-FW3a-HV4-FW3b-CDR3-FW4 comprising
(1) amplifying DNA sequences encoding two or more contiguous peptide domains of FW1-CDR1-FW2-HV2-FW3a-HV4-FW3b-CDR3-FW4, wherein said two or more contiguous peptide domains when ligated encode an antigen specific antigen binding molecule of formula (I), in the presence of a plurality of heterologous oligomers complementary to CDR1 or CDR3 domains, to form a plurality of amplified DNA sequences encoding an antigen specific antigen binding molecule of formula (I) wherein FW1 comprises one or more humanised sequences according to –/D A/I/T S/Q/R V/M N/T/D Q S P S S L S A S V G D R V T I T C V L/V T/R D/G T/A/S (SEQ ID NO: 1)
(2) ligating together said amplified DNA sequences encoding two or more contiguous peptide domains to form DNA sequences encoding an antigen specific binding molecule having the peptide domain structure of formula (I);
(3) cloning the ligated DNA obtained in (2) into a display vector; and
(4) transforming a host with said display vector to produce a library of said antigen specific antigen binding molecules.

Antigen specific antigen binding molecules of the invention may therefore be constructed of any of the amino acid sequences for the various regions disclosed herein according to the basic structure (as defined herein):

FW1-CDR1-FW2-HV2-FW3a-HV4-FW3b-CDR3-FW4 in which each of FW1, CDR1, FW2, HV2, FW3a, HV4, FW3b, CDR3, and FW4 represent a peptide sequence, where "FW" is a "Framework" region, "CDR1" is a "Complementarity Determining Region 1", "HV" is a "Hypervariable" region, and "CDR3" is a "Complementarity Determining Region 3". Examples of suitable peptide domain sequences are described herein.

An antigen specific antigen binding molecule having a peptide domain structure represented by the following formula (I) may be termed a N-terminal variable domain (VNAR). The Novel or New antigen receptor (IgNAR) is an approximately 160 kDa homodimeric protein found in the sera of cartilaginous fish. Each molecule consists of a single N-terminal variable domain (VNAR) and five constant domains (CNAR). The IgNAR domains are members of the immunoglobulin-superfamily. The VNAR is a tightly folded domain with structural and some sequence similarities to the immunoglobulin and T-cell receptor Variable domains and to cell adhesion molecules and is termed the VNAR by analogy to the N Variable terminal domain of the classical immunoglobulins and T Cell receptors. The VNAR shares limited sequence homology to immunoglobulins, for example 25-30% similarity between VNAR and human light chain sequences (Dooley, H. and Flajnik, M. F., Eur. J. Immunol., 2005. 35(3): p. 936-945).

Kovaleva M. et al Expert Opin. Biol. Ther. 2014. 14(10): p. 1527-1539 and Zielonka S. et al mAbs 2015. 7(1): p. 15-25 have provided summaries of the structural characterization and generation of the VNARs which are hereby incorporated by reference.

The VNAR binding surface, unlike the variable domains in other natural immunoglobulins, derives from four regions of diversity: CDR1, HV2, HV4 and CDR3, joined by intervening framework sequences in the order: FW1-CDR1-FW2-HV2-FW3a-HV4-FW3b-CDR3-FW4. The combination of a lack of a natural light chain partner and lack of CDR2 make VNARs the smallest naturally occurring binding domains in the vertebrate kingdom.

The specific antigen binding molecules of the invention may be classified according to the general structure of the nomenclature for VNARs according to Liu et al (Liu et al Mol. Immunol. 44, 1775-1783 (2007) and Liu et al BMC Biotechnology, 7(78) doi:10.1186/1472-6750-7-78 (2007)).

In one embodiment of the invention, the amplification of DNA in step (1) is carried out in the presence of oligomers which encode a sequence of any amino acid except cysteine. In other words, the resulting CDR regions encoded by the amplified DNA will not include cysteine. However, in other embodiments cysteine may be present in the CDR regions.

All VNARs contain two canonical cys residues in FW1 and FW3 which create the classic immunoglobulin (Ig) fold. In addition, they are characterised by the addition of extra cysteine (cys) residues in the CDRs and FWs:

Type I: non-canonical cys residues in FW2 and FW4 in addition to two extra cys in CDR3—the FW-CDR3 pairings form a tightly constrained CDR3 structure.

Type II: non-canonical cys residues in CDR1 and CDR3 that create a disulphide bridge that results in the CDR3 being in a protruding position.

Type III: non-canonical cys residues as a Type II however they contain a conserved W in CDR1

All the above is based on nurse shark nomenclature. In the present invention other new isotypes have been isolated which are described as "type b" variants as follows:

Type IIb: no non-canonical cys residues in CDR1 and CDR3—resulting in a very flexible CDR3 (2V is an example of a type IIb variant).

Type IIIb: no non-canonical cys residues in CDR1 and CDR3 but does have the invariant W in CDR1 (5V is an example of a type IIIb variant).

It may be desirable to ensure that there are no non-canonical cysteine (C) residues in CDR1 and CDR3 which may provide for a more flexible CDR3 region. Such a structure may be referred to as a "Type IIb" isotype, following the general structure of nurse shark nomenclature for VNARs according to Liu et al (Liu et al Mol. Immunol. 44, 1775-1783 (2007) and Liu et al BMC Biotechnology, 7(78) doi:10.1186/1472-6750-7-78 (2007)).

In an alternative embodiment, it may also be desirable to ensure that there are no non-canonical cysteine (C) residues in CDR1 and CDR3, but also to have an invariant tryptophan (W) in CDR1. Such a structure may be referred to as a "Type IIIb" isotype, following the general structure of nurse shark nomenclature for VNARs according to Liu et al (cited above).

In one embodiment of the invention, the antigen specific antigen binding molecule may be a fusion of region FW1, CDR1, FW2, HV2, FW3a, HV4, FW3b, CDR3, and/or FW4 is from a type IIb and a type IIIb VNAR. The fused IIb and IIIb portions may be connected in either order as appropriate in order to form a VNAR structure.

In one embodiment of the invention, the DNA sequence may have the final three amino acid residues in domain FW3b as CKA or CRA and first three amino acid residues of FW4 as Y or D and GA. Other FW3b sequences may comprise variations such as CAN, CRG, CKV, CKT, and/or CHT. Accordingly, the final three amino acid residues of FW3b may be selected from the group consisting of CKA, CRA, CAN, CRG, CKV, CKT and CHT (preferably CKA and CRA) and/or the first three amino acid residues of FW4 may be DGA or YGA.

Other alternative fusions of isotypes may also be made according to the present invention. For example, regions from a type I VNAR may be fused with a type III VNAR, or regions from a type I VNAR may be fused with a type II VNAR. Variations of isotype regions type I, type II and type III, such as described in the present invention, of type Ib, type IIb and type IIIb are also included. Fusions can also include any isotype fusion across VNAR families, i.e. isotype regions isolated from any species of Elasmobranchii. For example, a type II region from nurse shark fused with a type II region from dogfish, or a type IIb from Wobbegong fused with a type IIIb from dogfish.

In the sequences disclosed herein, "/" means "or" and denotes residues that the inventors have shown may vary as specified. In this context, "–" means a gap or no amino acid. X is any amino acid. For example, "V/M" means a residue which may be either V or M. Likewise, "–/D" means a residue which may be either absent or D. Likewise, "A/I/T" means a residue may be A, I or T. Where sequence identity values are specified, sequence identity may be calculated starting from any one of the residues separated by a "/".

In one embodiment, at least one of FW2, FW3a, FW3b and FW4 each comprise one or more sequences selected from the group consisting of:

FW2 comprises one or more sequences according to T S/Y W F/Y R/Q K/Q N/K P/S G T/S (SEQ ID NO: 2);

FW3a comprises one or more sequences according to G R Y/F V/S E/G S/T V/G/I N/S (SEQ ID NO: 3);

FW3b comprises one or more sequences according to F S/T L R/T I K/S/N D/S L T/Q V/P A/E D S/F A/G T Y Y/R/I C K/R/A A/S/L (SEQ ID NO: 4), and FW4 comprises one or more sequences according to D/Y/F G A/G/Q G T K/V V/L E/T I/V K/N (SEQ ID NO: 5).

FW1 comprises one or more humanised sequences according to -/D A/I/T S/Q/R V/M N/T/D Q S P S S L S A S V G D R V T I T C V L/V T/R D/G T/AIS (SEQ ID NO: 1). However, in an alternative aspect, the sequence of FW1 is not defined and the library is alternatively characterised by one or more of:

FW2 comprises one or more sequences according to T S/T W F/Y R/Q K/Q N/K P/S G T/S (SEQ ID NO: 2);

FW3a comprises one or more sequences according to G R Y/F V/S E/G S/T V/G/I N/S (SEQ ID NO: 3);

FW3b comprises one or more sequences according to F S/T L R/T I K/S/N D/S L T/Q V/P A/E D S/F A/G T Y Y/R/I C K/R/A A/S/L (SEQ ID NO: 4), and FW4 comprises one or more sequences according to D/Y/F G A/G/Q G T K/V V/L E/T I/V K/N (SEQ ID NO: 5).

In this alternative aspect typically the one or more of FW2, FW3a, FW3b and FW4 sequences is humanized. The humanised FW2, FW3a, FW3b and/or FW4 sequences may be any humanised FW2, FW3a, FW3b and FW4 sequence or sequences disclosed herein.

FW2 may comprise one or more sequences according to T S/Y W F/Y R/Q K/Q N/K P/S G T/S (SEQ ID NO: 2).

FW3a may comprise one or more sequences according to G R Y/F V/S E/G S/T V/G/I N/S (SEQ ID NO: 3).

FW3b may comprise one or more sequences according to F S/T L R/T I K/S/N D/S L T/Q V/P A/E D S/F A/G T Y Y/R/1 C K/R/A A/S/L (SEQ ID NO: 4).

FW4 may comprise one or more sequences according to D/Y/F G A/G/Q G T K/V V/L E/T I/V K/N (SEQ ID NO: 5).

In one embodiment, two of FW2, FW3a, FW3b and FW4 comprise a humanised sequence and the remaining two of FW2, FW3a, FW3b and FW4 comprise a sequence for the corresponding at least one of FW2, FW3a, FW3b and FW4 from a member of a species in the Elasmobranchii subclass, or for each sequence from a member of a species in the Elasmobranchii subclass, an amino acid sequence with (i) at least 70% identity thereto, and/or (ii) one, two, or three amino acid substitutions relative thereto.

In one embodiment, three of FW2, FW3a, FW3b and FW4 comprise a humanised sequence and the remaining one of FW2, FW3a, FW3b and FW4 comprises a sequence for the corresponding at least one of FW2, FW3a, FW3b and FW4 from a member of a species in the Elasmobranchii subclass, or for each sequence from a member of a species in the Elasmobranchii subclass, an amino acid sequence with (i) at least 70% identity thereto, and/or (ii) one, two, or three amino acid substitutions relative thereto.

Elasmobranchii is a subclass of the class Chondrichthyes and includes the cartilaginous fish, sharks, rays and skates. Members of this subclass can be furthered subdivided into eleven orders; Carchariniformes; Heterodontiformes; Hexanchiformes; Lamniformes; Orectolobiformes; Pristiformes; Rajiformes; Squaliformes; Squatiniformes; Torpediniformes. Each order can then be subdivided into a number families. For example, the FW4 sequence may be from *Ginglymostoma cirratum*, from the family Ginglymostomatidae, of the order Orectolobformes and/or *Squalus acanthias* from the family Squalidae, of the order Squaliformes.

The amino acid sequence may have at least 70%, 75%, 80%, 85%, 90% and still more preferably 95% (still more preferably at least 96%, 97%, 98% or 99%) identity to a sequence from a member of a species in the Elasmobranchii subclass.

The amino acid sequence may have three, preferably two, or more preferably one amino acid substitution relative to a sequence from a member of a species in the Elasmobranchii subclass. The one or more substitutions may be conservative amino acid substitutions.

Sequence identity and/or amino acid substitutions may be relative to any FW4 sequence of any species in the Elasmobranchii subclass. For example, sequence identity and/or amino acid substitutions may be relative to an FW4 sequence from *Ginglymostoma cirratum*, from the family Ginglymostomatidae, of the order Orectolobformes and/or *Squalus acanthias* from the family Squalidae, of the order Squaliformes.

Sequence identity and/or amino acid substitutions may be relative to YGGGTVVTVN (SEQ ID NO: 21).

FW4 may comprise a sequence according to YGGGTVVTVN (SEQ ID NO: 21) or an amino acid sequence with either (i) at least 70% identity thereto, or (ii) one, two, or three amino acid substitutions relative thereto.

FW4 may comprise a sequence for FW4 from a member of a species in the Elasmobranchii subclass.

FW4 may comprise a sequence according to YGGGTVVTVN (SEQ ID NO: 21).

FW3a may comprise a sequence for FW3a from a member of a species in the Elasmobranchii subclass or FW3b may comprise a sequence for FW3b from a member of a species in the Elasmobranchii subclass.

FW3a may comprise a sequence for FW3a from a member of a species in the Elasmobranchii subclass.

FW3b may comprise a sequence for FW3b from a member of a species in the Elasmobranchii subclass.

At least three amino acid residues from the combined sequences of FW2, FW3a, FW3b and FW4 may be humanised. Accordingly, starting from the combined sequence of FW2, FW3a, FW3b and FW4 from a member of a species in the Elasmobranchii subclass at least three amino acid residues may be substituted for corresponding residues from DPK-9. The FW2, FW3a, FW3b and FW4 sequences may be from the same member of a species in the Elasmobranchii subclass or from two or more different members of a species in the Elasmobranchii subclass, such as different individuals of the same species. Alternatively, FW2, FW3a, FW3b and FW4 sequences may be from two or more different species in the Elasmobranchii subclass.

The at least three humanised residues may be selected from any three humanised residues in any FW2, FW3a, FW3b and/or FW4 sequences disclosed herein. For example, the at least three humanised residues may be selected from any three humanised residues illustrated in FIG. 1.

At least four, at least five, at least six, at least seven, at least eight, at least nine, at least ten, at least 11, at least 12, at least 13, at least 14 or at least 15 amino acid residues from the combined sequences of FW2, FW3a, FW3b and FW4 may be humanised.

The one or more humanised sequences for FW1 may be selected from the group consisting of:

A/T S/R V N/D Q S P S S L S A S V G D R V T I T C V L I V T D/G T/A; (SEQ ID NO: 6)

D I Q M T Q S P S S L S A S V G D R V T I T C V L/V T D/G T/A; (SEQ ID NO: 7)
and

ARVDQSPSSLSASVGDRVTITCVLRDS. (SEQ ID NO: 8)

The one or more sequences for FW2 may be selected from the group consisting of:

T S/Y W F/Y R K N P G T/S; (SEQ ID NO: 9)

T S/Y W Y/F Q Q K P G T/S; (SEQ ID NO: 10)
and

TYWYRKKSGS. (SEQ ID NO: 11)

The one or more sequences for FW3a may be selected from the group consisting of:

GRYVESVN; (SEQ ID NO: 12)

GRFSGSGS; (SEQ ID NO: 13)

GRYVETVN; (SEQ ID NO: 14)
and

GRYVETIN. (SEQ ID NO: 15)

The one or more sequences for FW3b may be selected from the group consisting of:

F S L R I K D L T V A D S A T Y Y/I C K/R A; (SEQ ID NO: 16)

F T L T I S S L Q P E D F A T Y Y/I C K/R A; (SEQ ID NO: 17)

FTLTISSLQPEDFATYYCAS; (SEQ ID NO: 18)
and

FSLRINDLTVEDSGTYRCKL. (SEQ ID NO: 19)

The one or more sequences for FW4 may be selected from the group consisting of:

D/Y/F G A/G/Q G T K V/L E I K; (SEQ ID NO: 20)
and

YGGGTVVTVN. (SEQ ID NO: 21)

At least one of FW2, FW3a, FW3b and FW4 may each comprise one or more sequences selected from the group consisting of:
FW2 comprises one or more sequences according to T S/Y W F/Y R/Q K/Q N/K P/S G T/S (SEQ ID NO: 22);
FW3a comprises one or more sequences according to G R Y/F V/S E/G S/T V/G/I N/S (SEQ ID NO: 23);
FW3b comprises one or more sequences according to F S/T L R/T I K/S/N D/S L T/Q V/P A/E D S/F A/G T Y Y/R/I C K/R/A A/S/L (SEQ ID NO: 24); and
FW4 comprises one or more sequences according to D/Y G A G T K V E I K (SEQ ID NO: 25);

The method may be defined by any combination of the above sequences. For example, the method may be defined by at least two of FW2, FW3a, FW3b and FW4 each comprising one or more or the above sequences, at least three of FW2, FW3a, FW3b and FW4 each comprising one or more or the above sequences or all four of FW2, FW3a, FW3b and FW4 each comprising one or more or the above sequences. Preferably,
FW2 comprises one or more sequences according to T S/Y W F/Y R/Q K/Q N/K P/S G T/S (SEQ ID NO: 22);
FW3a comprises one or more sequences according to G R Y/F V/S E/G S/T V/G/I N/S (SEQ ID NO: 23);
FW3b comprises one or more sequences according to F S/T L R/T I K/S/N D/S L T/Q V/P A/E D S/F A/G T Y Y/R/I C K/R/A A/S/L (SEQ ID NO: 24); and
FW4 comprises one or more sequences according to D/Y G A G T K V E I K (SEQ ID NO: 25).

The humanised antigen specific antigen binding molecules may comprise CDRs and hyper-variable regions (HV) of certain lengths. In one embodiment,
CDR1 is a region of 6 amino acids,
HV2 is a region of 9 amino acids,
HV4 is a region of 5 amino acids, and/or
CDR3 is a region of 8 to 36 amino acids.

The library may comprise a diversity of CDR and HV sequences. In one embodiment, at least one of CDR1, HV2, HV4 and CDR3 each comprise one or more sequences selected from the group consisting of:
CDR1 comprises one or more sequences according to Y/T/R/I/K/N/S C/Y P/S/A/G W/L H/S/Y N/R/G/S (SEQ ID NO: 26), wherein if CDR1 comprises a Cysteine residue CDR3 also comprises a Cysteine residue;
HV2 comprises one or more sequences according to S/T/P N/D Q/W E R I/M S I G/S (SEQ ID NO: 27);
HV4 comprises one or more sequences according to K G/R T/P/S K/M S (SEQ ID NO: 28); and CDR3 comprises one or more sequences according to the following formula (II):

J-J-[Xaa]$_n$-O-U-U'

Wherein:
J is any naturally occurring amino acid apart from Cysteine,
Xaa is any naturally occurring amino acid,
n is 3 to 31,
O is an amino acid selected from the group consisting of Cysteine, Aspartic acid, Glutamic acid, Phenylalanine, Glycine, Lysine, Asparagine, Serine, Valine and Tyrosine, U is an amino acid selected from the group consisting of Cysteine, Aspartic acid, Glycine, Histidine, Tryptophan and Tyrosine, U' is an amino acid selected from the group consisting of Tyrosine, Leucine, Valine and Phenylalanine; and wherein CDR3 comprises either one Cysteine residue or no Cysteine residues and if CDR3 comprises a Cysteine residue CDR1 also comprises a Cysteine residue.

The incorporation of a cysteine (Cys) residue into each of the CDR regions increases the diversity of the library by creating the potential for CDR1 to CDR3 disulphide bridging as seen in classical Type II VNAR domains.

In some embodiments, no Cysteine residues are present in CDR1, HV2, HV4 and CDR3.

The number of possible combinations for each position of each CDR and HV region is illustrated in FIG. 16.

The library clones may have equivalent levels of diversity and/or amino acid content to a naïve repertoire.

The diversity of CDR and HV sequences according to the present invention cumulatively allows a very wide diversity of clone sequences in the library. This in turn has the effect of making the library extremely versatile and likely to provide an improved hit-rate of pre-humanised antigen specific antigen binding molecules for a given target of interest.

In some embodiments, the library may comprise a population of clones at least 90% of which comprises an amino acid sequence for FW1, FW2, FW3a, FW3b and/or FW4 having at least 90% identity to the amino acid sequence for FW1, FW2, FW3a, FW3b and/or FW4 respectively of 90% of the other clones.

This library may be termed a "sub-library". The sub-library may comprise a population of clones which each comprise an amino acid sequence for FW1, FW2, FW3a, FW3b and/or FW4 having up to three, up to two or up to one non-identical amino acid relative to the amino acid sequence for FW1, FW2, FW3a, FW3b and/or FW4 respectively of 90% of the other clones. The sub-library may comprise a population of clones which each comprise an amino acid sequence for FW1, FW2, FW3a, FW3b and/or FW4 having an identical amino acid sequence to the amino acid sequence for FW1, FW2, FW3a, FW3b and/or FW4 respectively of 90% of the other clones. The sub-library may comprise a population of clones which each comprise an amino acid sequence for FW1, FW2, FW3a, FW3b and FW4 having an identical amino acid sequence to the amino acid sequence for FW1, FW2, FW3a, FW3b and FW4 respectively of the other clones. The method may therefore be a method for the production of a sub-library, optionally wherein the sub-library comprises diversity in the CDR1, HV2, HV4 and CDR3 regions but not in the FW1, FW2, FW3a, FW3b and/or FW4 regions. Such a sub-library may be useful when a user wishes to rapidly prepare humanised antigen specific antigen binding molecules for a given antigen with a known level of humanisation needed is known. The method of the invention may be run in parallel as a method for production of a super-library of sub-libraries, wherein each sub-library comprises diversity in the CDR1, HV2, HV4 and CDR3 regions but not in the FW1, FW2, FW3a, FW3b and/or FW4 regions and the level of humanisation of the FW1, FW2, FW3a, FW3b and/or FW4 regions varies between sub-libraries. The method may therefore be a method for the production of a super-library of sub-libraries of humanised antigen specific antigen binding molecules wherein the method of the first aspect of the invention is repeated using a different FW1, FW2, FW3a, FW3b and/or FW4 sequence for each sub-library.

The method may further comprise:

Subjecting the sequences of one or more of CDR1, HV2, HV4 and CDR3 to controlled mutagenesis, and Selecting desired CDR1, HV2, HV4 and/or CDR3 sequences by affinity maturation against a target molecule.

Methods of controlled mutagenesis for example overlapping PCR are known to the skilled person. Likewise, methods of affinity maturation against a target molecule, such as surface-panning and solution-sorting are known to the skilled person.

Equivalent to the first aspect of the invention defined in the claims is an alternative statement of the first aspect wherein the method comprises (i) synthesising a population of DNA sequences each encoding a humanised antigen specific antigen binding molecule having a peptide domain structure represented by the following formula (i) wherein FW1 comprises one or more humanised sequences according to –/D A/I/T S/Q/R V/M N/T/D Q S P S S L S A S V G D R V T I T C V L/V T/R D/G T/A/S (SEQ ID NO: 1);

(ii) amplifying the population of DNA sequences;

(iii) cloning the amplified DNA obtained in (ii) into a display vector; and (iv) transforming a host with said display vector to produce a library of said antigen specific antigen binding molecules.

The skilled person will appreciate that steps (i) to (iv) of this equivalent may be substituted for steps (1) to (4) of the claimed approach, mutatis mutandis. Any further features of the first aspect of the invention as defined in the claims may be combined with the above alternative statement of the first aspect. For example, any sequence of FW2, FW3a, FW3b and/or FW4 disclosed herein may be combined with the above alternative statement of the first aspect. Either the claimed approach or this equivalent approach can be used to make a library according to the invention. When describing the library construction, one would first synthesise the library DNA population prior to its amplification for cloning with all the required variation at the positions described/designed. This could be done as a single continuous sequence population or as contiguous sequences that can be joined through the amplification process. The common feature is how the inventors design the library (or parts of a library) to drive amino acid variation and clone differences in the final library. More diversity typically results in a better library.

The method may further comprise the following steps before step (1):

(1a) isolating RNA from a member of a species in the Elasmobranchii subclass;

(2a) amplifying DNA sequences from RNA obtained in (1a) which encode antigen specific antigen binding molecules to create a database of DNA sequences encoding antigen specific binding molecules;

(3a) selecting a DNA sequence from the database prepared in (2a).

Where the method further comprises steps (1a), (2a) and (3a) the said two or more contiguous peptide domains of (1) may be from at least two heterologous DNA sequences selected in (3a). RNA may be isolated from one member or several different members of species in the Elasmobranchii subclass. References to a member of a species in the Elasmobranchii subclass therefore include references to one or more different members of a species in the Elasmobranchii subclass also. Step (1a) may therefore comprise isolating RNA from a member or members of species in the Elasmobranchii subclass.

Elasmobranchii is a subclass of the class Chondrichthyes and includes the cartilaginous fish, sharks, rays and skates.

Potential combinations of contiguous peptide domains of FW1-CDR1-FW2-HV2-FW3a-HV4-FW3b-CDR3-FW4 which when ligated encode an antigen specific antigen binding molecule of formula (I) can be defined by the formula (III):

P-Q-R, where P-Q-R is FW1-CDR1-FW2-HV2-FW3a-HV4-FW3b-CDR3-FW4 and where each of P, Q and R represent the contiguous peptide domains and optionally where Q or R is absent. Some non-limiting examples of contiguous peptide domains which when ligated together encode an antigen specific antigen binding molecule of formula (I) shown in Table 1 below:

TABLE 1

| No. | P | Q | R |
|---|---|---|---|
| 1 | FW1 | CDR1-FW2-HV2-FW3a-HV4-FW3b | CDR3-FW4 |
| 2 | FW1 | CDR1-FW2-HV2-FW3a-HV4 | FW3b-CDR3-FW4 |
| 3 | FW1 | CDR1-FW2-HV2 | FW3a-HV4-FW3b-CDR3-FW4 |
| 4 | FW1-CDR1 | FW2-HV2-FW3a-HV4-FW3b-CDR3-FW4 | |
| 5 | FW1-CDR1-FW2 | HV2-FW3a-HV4-FW3b | CDR3-FW4 |
| 6 | FW1-CDR1-FW2-HV2-FW3a | HV4-FW3b | CDR3-FW4 |
| 7 | FW1-CDR1-FW2-HV2-FW3a-HV4-FW3b | | CDR3-FW4 |
| 8 | FW1-CDR1-FW2-HV2 | FW3a-HV4-FW3b-CDR3-FW4 | |
| 9 | FW1-CDR1-FW2-HV2-FW3a | HV4-FW3b-CDR3-FW4 | |
| 10 | FW1-CDR1-FW2-HV2-FW3a-HV4 | | FW3b-CDR3-FW4 |

Members of this subclass can be furthered subdivided into eleven orders; Carchariniformes; Heterodontiformes; Hexanchiformes; Lamniformes; Orectolobiformes; Pristiformes; Rajiformes; Squaliformes; Squatiniformes; Torpediniformes. Each order can then be subdivided into a number families. For example, the methods of the invention may relate to *Ginglymostoma cirratum*, from the family Ginglymostomatidae, of the order Orectolobformes and/or *Squalus acanthias* from the family Squalidae, of the order Squaliformes.

It is therefore possible for two, three, four, five, six, seven or eight peptide domains to be used which when ligated encode an antigen specific antigen binding molecule of formula (I) as represented by FW1-CDR1-FW2-HV2-FW3a-HV4-FW3b-CDR3-FW4

The said two or more contiguous peptide domains of FW1-CDR1-FW2-HV2-FW3a-HV4-FW3b-CDR3-FW4 can be are selected from the group consisting of FW1, CDR1, FW2, HV2, FW3a, HV4, FW3, CDR3, and FW4, and combinations thereof. There may be two, three, four or five such peptide domains.

Other fragments of contiguous peptide domains which when ligated together encode an antigen specific antigen binding molecule of formula (I) can be prepared by dividing up the peptide domain sequence defined by formula (I) in an alternative manner as convenient.

If each Framework (FW) region is in a separate fragment then potentially 4 or 5 peptide domains may be prepared. In which case, the formula (III) is represented by:

P-Q-R-S where there are 4 separate peptide domains, where P-Q-R-S is FW1-CDR1-FW2-HV2-FW3a-HV4-FW3b-CDR3-FW4 and where each of P, Q, R and S represent the contiguous peptide domains; or

P-Q-R-S-T where there are 5 separate peptide domains where P-Q-R-S-T is FW1-CDR1-FW2-HV2-FW3a-HV4-FW3b-CDR3-FW4, and where each of P, Q, R, S and T represent the contiguous peptide domains.

Examples of contiguous peptide domains according to these alternative embodiments are shown in Table 2 below:

TABLE 2

| No. | P | Q | R | S |
|---|---|---|---|---|
| 11 | FW1 | CDR1-FW2-HV2- | FW3a- | HV4-FW3b-CDR3-FW4 |
| 12 | FW1 | CDR1-FW2- | HV2-FW3a-HV4 | FW3b-CDR3-FW4 |
| 13 | FW1- CDR1 | FW2- HV2- FW3a-HV4- | FW3b- CDR3 | -FW4 |

TABLE 2-continued

| No. | P | Q | R | S | T |
|---|---|---|---|---|---|
| 14 | FW1 | CDR1-FW2-HV2- | FW3a- | HV4-FW3b | CDR3-FW4 |
| 15 | FW1 | CDR1-FW2- | HV2-FW3a-HV4 | FW3b- | CDR3-FW4 |
| 16 | FW1- CDR1 | FW2- HV2- | FW3a-HV4 | FW3b- CDR3 | -FW4 |

In one embodiment of this aspect of the invention, the two or more contiguous peptide domains are the three domains represented by FW1-CDR1-FW2-HV2-FW3a-HV4-FW3b-CDR3-FW4 are FW1, CDR1-FW2-HV2-FW3a-HV4-FW3b, and CDR3-FW4.

In this embodiment of the invention step (1) may be defined as being (1) amplifying DNA sequences encoding peptide domains FW1, CDR1-FW2-HV2-FW3a-HV4-FW3, and CDR3-FW4 from at least two heterologous DNA sequences selected in (3a) in the presence of a plurality of heterologous oligomers complementary to CDR1 or CDR3 domains in sequences selected in (3a) to form a plurality of amplified DNA sequences encoding peptide domains FW1, CDR1-FW2-HV2-FW3a-HV4-FW3, and CDR3-FW4. Consequently, step (2) according this embodiment of the invention can be defined as being ligating together said amplified DNA sequences encoding peptide domains FW1, CDR1-FW2-HV2-FW3a-HV4-FW3, and CDR3-FW4 to form DNA sequences encoding an antigen specific binding molecule having the peptide domain structure of formula (I).

In one embodiment of the invention, the template derived HV2 and HV4 loops within different contexts may be achieved through alternatively splicing PCR fragments encoding template derived HV2 and HV4 pairings with respectively derived FW1, and CDR1 and CDR3 fragments.

Selection of the DNA sequence from the database prepared in step (2a) according to step (3a) of the method of the first aspect of the invention can be made according to an analysis of the expressed amino acid sequences for the DNA sequences prepared. The translated DNA sequences can be examined in terms of amino acid (AA) content, relative positional conservation and frequency across the analysed population in addition to CDR3 length distribution.

From an analysis of the expressed DNA sequences in the database of natural sequences compared to expressed sequences from the library it is possible to select DNA sequences based upon the degree of natural content in either CDR1 and/or CDR3 and the relative diversity present in CDR1 and/or CDR3 also.

Natural sequence content is defined as a sequence identity of at least about 80%, 85%, 90% or 95%, for example about 80% to about 95%, or about 85% to about 90%, compared with a corresponding naturally expressed VNAR sequence. A high level of diversity is defined as a sequence identity of about 60% to about 75%, suitably about 65% to about 70%, where a diversity of about 60% to about 65% may be suitable compared to a corresponding naturally expressed VNAR sequence.

For example, it may be desirable to have a natural version of CDR1 and a high level of diversity on CDR3. The addition of cysteine residues can be achieved by using TRM oligonucleotides in the DNA amplification process.

According to a second aspect of the invention, there is provided a process for the production of a humanised antigen specific antigen binding molecule, comprising
(1) selecting desired clones from the library prepared according to a method of any preceding claim;
(2) isolating and purifying the humanised antigen specific antigen binding molecules from these clones;
(3) cloning the DNA sequences encoding the humanised antigen specific antigen binding molecules into an expression vector; and
(4) transforming a host to allow expression of the expression vector.

According to a third aspect of the invention, there is provided a method for the production of a humanised antigen specific antigen binding molecule having a peptide domain structure represented by the following formula (I):

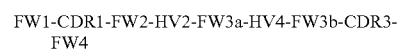

comprising
(1) amplifying DNA sequences encoding two or more contiguous peptide domains of FW1-CDR1-FW2-HV2-FW3a-HV4-FW3b-CDR3-FW4, wherein said two or more contiguous peptide domains when ligated encode an antigen specific antigen binding molecule of formula (I), in the presence of a plurality of heterologous oligomers complementary to CDR1 or CDR3 domains, to form a plurality of amplified DNA sequences encoding an antigen specific antigen binding molecule of formula (I) wherein FW1 comprises one or more humanised sequences according to –/D A/I/T S/Q/R V/M N/T/D Q S P S S L S A S V G D R V T I T C V L/V T/R D/G T/A/S (SEQ ID NO: 1)
(2) ligating together said amplified DNA sequences encoding two or more contiguous peptide domains to form DNA sequences encoding an antigen specific binding molecule having the peptide domain structure of formula (I);
(3) cloning the ligated DNA obtained in (2) into a display vector; and
(4) transforming a host with said display vector to produce a library of said antigen specific antigen binding molecules;
(5) selecting a desired clone from the library;
(6) isolating and purifying the antigen specific antigen binding molecule from the clone;
(7) cloning the DNA sequences encoding the antigen specific antigen binding molecule into an expression vector; and
(8) transforming a host to allow expression of the expression vector.

In one embodiment of the invention, the amplification of DNA in step (1) is carried out in the presence of oligomers which encode a sequence of any amino acid except cysteine. In other words, the resulting CDR regions encoded by the amplified DNA will not include cysteine. However, in other embodiments cysteine may be present in the CDR regions.

Definitions

An antigen specific antigen binding molecule of the invention comprises amino acid sequence which may be derived from a synthetic library of VNAR molecules prepared according to a method of the invention. The terms VNAR, IgNAR and NAR may be used interchangeably also.

Amino acids are represented herein as either a single letter code or as the three letter code or both.

The term "affinity purification" means the purification of a molecule based on a specific attraction or binding of the molecule to a chemical or binding partner to form a combination or complex which allows the molecule to be separated from impurities while remaining bound or attracted to the partner moiety. The term "Complementarity Determining Regions" or CDRs (i.e., CDR1 and CDR3) refers to the amino acid residues of a VNAR domain the presence of which are necessary for antigen binding. Each VNAR typically has three CDR regions identified as CDR1 and CDR3. Each complementarity determining region may comprise amino acid residues from a "complementarity determining region" and/or those residues from a "hypervariable loop" (HV). In some instances, a complementarity determining region can include amino acids from both a CDR region and a hypervariable loop. According to the generally accepted nomenclature for VNAR molecules, a CDR2 region is not present. As used herein, whenever a CDR or HV is said to "comprise" a sequence, this term also includes a CDR or HV "consisting of" the same sequence.

"Framework regions" (FW) are those VNAR residues other than the CDR residues. Each VNAR typically has five framework regions identified as FW1, FW2, FW3a, FW3b and FW4. As used herein, whenever a FW is said to "comprise" a sequence, this term also includes a FW "consisting of" the same sequence.

A "codon set" refers to a set of different nucleotide triplet sequences used to encode desired variant amino acids. A set of oligonucleotides can be synthesized, for example, by solid phase synthesis, including sequences that represent all possible combinations of nucleotide triplets provided by the codon set and that will encode the desired group of amino acids. A standard form of codon designation is that of the IUB code, which is known in the art and described herein.

A codon set is typically represented by 3 capital letters in italics, e.g. NNK, NNS, XYZ, DVK etc. A "non-random codon set" therefore refers to a codon set that encodes select amino acids that fulfill partially, preferably completely, the criteria for amino acid selection as described herein. Synthesis of oligonucleotides with selected nucleotide "degeneracy" at certain positions is well known in that art, for example the TRIM approach (Knappek et al.; J. Mol. Biol. (1999), 296, 57-86); Garrard & Henner, Gene (1993), 128, 103). Such sets of oligonucleotides having certain codon sets can be synthesized using commercial nucleic acid synthesizers (available from, for example, Applied Biosystems, Foster City, CA), or can be obtained commercially (for example, from Life Technologies, Rockville, MD). A set of oligonucleotides synthesized having a particular codon set will typically include a plurality of oligonucleotides with different sequences, the differences established by the codon set within the overall sequence. Oligonucleotides used according to the present invention have sequences that allow for hybridization to a VNAR nucleic acid template and also may where convenient include restriction enzyme sites.

"Cell", "cell line", and "cell culture" are used interchangeably (unless the context indicates otherwise) and such designations include all progeny of a cell or cell line. Thus, for example, terms like "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

"Control sequences" when referring to expression means DNA sequences necessary for the expression of an operably linked coding sequence in a particular host organism. The control sequences that are suitable for prokaryotes, for example, include a promoter, optionally an operator sequence, a ribosome binding site, etc. Eukaryotic cells use control sequences such as promoters, polyadenylation signals, and enhancers.

The term "coat protein" means a protein, at least a portion of which is present on the surface of the virus particle. From a functional perspective, a coat protein is any protein which associates with a virus particle during the viral assembly process in a host cell, and remains associated with the assembled virus until it infects another host cell.

The "detection limit" for a chemical entity in a particular assay is the minimum concentration of that entity which can be detected above the background level for that assay. For example, in the phage ELISA, the "detection limit" for a particular phage displaying a particular antigen binding fragment is the phage concentration at which the particular phage produces an ELISA signal above that produced by a control phage not displaying the antigen binding fragment.

A "fusion protein" and a "fusion polypeptide" refer to a polypeptide having two portions covalently linked together, where each of the portions is a polypeptide having a different property. The property may be a biological property, such as activity in vitro or in vivo. The property may also be a simple chemical or physical property, such as binding to a target antigen, catalysis of a reaction, etc. The two portions may be linked directly by a single peptide bond or through a peptide linker containing one or more amino acid residues. Generally, the two portions and the linker will be in reading frame with each other. Preferably, the two portions of the polypeptide are obtained from heterologous or different polypeptides. The multi-domain antigen specific antigen binding molecules of the invention are an example of a fusion protein since they comprise two or more VNAR domains.

The term "fusion protein" in this text means, in general terms, one or more proteins joined together by chemical means, including hydrogen bonds or salt bridges, or by peptide bonds through protein synthesis or both.

"Heterologous DNA" is any DNA that is introduced into a host cell. The DNA may be derived from a variety of sources including genomic DNA, cDNA, synthetic DNA and fusions or combinations of these. The DNA may include DNA from the same cell or cell type as the host or recipient cell or DNA from a different cell type, for example, from an allogenic or xenogenic source. The DNA may, optionally, include marker or selection genes, for example, antibiotic resistance genes, temperature resistance genes, etc.

A "highly diverse position" refers to a position of an amino acid located in the variable regions of the light and heavy chains that have a number of different amino acid represented at the position when the amino acid sequences of known and/or naturally occurring antibodies or antigen binding fragments are compared. The highly diverse positions are typically in the CDR regions.

"Identity" describes the relationship between two or more polypeptide sequences or two or more polynucleotide sequences, as determined by comparing the sequences. Identity also means the degree of sequence relatedness (homology) between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic acids Research, 12, 387 (1984), BLASTP, BLASTN, and FASTA (Atschul et al., J. Molec. Biol. (1990) 215, 403).

Preferably, the amino acid sequence of the protein has at least 50% identity, using the default parameters of the BLAST computer program (Atschul et al., J. Mol. Biol. (1990) 215, 403-410) provided by HGMP (Human Genome Mapping Project), at the amino acid level, to the amino acid sequences disclosed herein.

More preferably, the protein sequence may have at least 55%, 60%, 65%, 66%, 67%, 68%, 69%, 70%, 75%, 80%, 85%, 90% and still more preferably 95% (still more preferably at least 96%, 97%, 98% or 99%) identity, at the nucleic acid or amino acid level, to the amino acid sequences as shown herein.

The protein may also comprise a sequence which has at least 50%, 55%, 60%, 65%, 66%, 67%, 68%, 69%, 70%, 75%, 80%, 85%, 90%, 95%, 96%, 97%, 98%, or 99% identity with a sequence disclosed herein, using the default parameters of the BLAST computer program provided by HGMP, thereto A "library" refers to a plurality of VNARs or VNAR fragment sequences (for example, polypeptides of the invention), or the nucleic acids that encode these sequences, the sequences being different in the combination of variant amino acids that are introduced into these sequences according to the methods of the invention.

"Ligation" is the process of forming phosphodiester bonds between two nucleic acid fragments. For ligation of the two fragments, the ends of the fragments must be compatible with each other. In some cases, the ends will be directly compatible after endonuclease digestion. However, it may be necessary first to convert the staggered ends commonly produced after endonuclease digestion to blunt ends to make them compatible for ligation. For blunting the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroform extraction and ethanol precipitation or by silica purification. The DNA fragments that are to be ligated together are put in solution in about equimolar amounts. The solution will also contain ATP, ligase buffer, and a ligase such as T4 DNA ligase at about 10 units per 0.5 μg of DNA. If the DNA is to be ligated into a vector, the vector is first linearized by digestion with the appropriate restriction endonuclease(s). The linearized fragment is then treated with bacterial alkaline phosphatase or calf intestinal phosphatase to prevent self-ligation during the ligation step.

A "mutation" is a deletion, insertion, or substitution of a nucleotide(s) relative to a reference nucleotide sequence, such as a wild type sequence.

"Natural" or "naturally occurring" VNARs, refers to VNARs identified from a non-synthetic source, for example, from a tissue source obtained ex vivo, or from the serum of an animal of the Elasmobranchii subclass. These VNARs can include VNARs generated in any type of immune response, either natural or otherwise induced. Natural VNARs include the amino acid sequences, and the nucleotide sequences that constitute or encode these antibodies. As used herein, natural VNARs are different than "synthetic VNARs", synthetic VNARs referring to VNAR sequences that have been changed from a source or template sequence, for example, by the replacement, deletion, or addition, of an amino acid, or more than one amino acid, at a certain position with a different amino acid, the different amino acid providing an antibody sequence different from the source antibody sequence.

The term "nucleic acid construct" generally refers to any length of nucleic acid which may be DNA, cDNA or RNA such as mRNA obtained by cloning or produced by chemical synthesis. The DNA may be single or double stranded. Single stranded DNA may be the coding sense strand, or it may be the non-coding or anti-sense strand. For therapeutic use, the nucleic acid construct is preferably in a form capable of being expressed in the subject to be treated.

"Operably linked" when referring to nucleic acids means that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promotor or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contingent and in reading frame. However, enhancers do not have to be contiguous. Linking is accomplished by ligation at convenient restriction sites. If such sites do not exist, the synthetic oligonucleotide adapters or linkers are used in accord with conventional practice.

"Phage display" is a technique by which variant polypeptides are displayed as fusion proteins to at least a portion of coat protein on the surface of phage, e.g., filamentous phage, particles. Phage display technology allows for the preparation of large libraries of randomized protein variants which can be rapidly and efficiently sorted for those sequences that bind to a target antigen with high affinity. The display of peptide and protein libraries on phage can be used for screening millions of polypeptides for ones with specific binding properties. Polyvalent phage display methods have been used for displaying small random peptides and small proteins through fusions to the genes encoding coat proteins pIII, pVIII, pVI, pVII or pIX of filamentous phage.

A "phagemid" is a plasmid vector having a bacterial origin of replication, e.g., ColEI, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle. An example of a phagemid display vector is pWRIL-1.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, fl, fd, Pf3 phage or a derivative thereof, or a lambdoid phage, such as lambda, 21, phi80, phi81, or a derivative thereof.

The term "protein" means, in general terms, a plurality of amino acid residues joined together by peptide bonds. It is used interchangeably and means the same as peptide, oligopeptide, oligomer or polypeptide, and includes glycoproteins and derivatives thereof. The term "protein" is also intended to include fragments, analogues, variants and derivatives of a protein wherein the fragment, analogue, variant or derivative retains essentially the same biological activity or function as a reference protein. Examples of protein analogues and derivatives include peptide nucleic acids, and DARPins (Designed Ankyrin Repeat Proteins).

A fragment, analogue, variant or derivative of the protein may be at least 25 preferably 30 or 40, or up to 50 or 100, or 60 to 120 amino acids long, depending on the length of the original protein sequence from which it is derived. A length of 90 to 120, 100 to 110 amino acids may be convenient in some instances.

The fragment, derivative, variant or analogue of the protein may be (i) one in which one or more of the amino acid residues are substituted with a conserved or non-conserved amino acid residue (preferably, a conserved amino acid residue) and such substituted amino acid residue may or may not be one encoded by the genetic code, or (ii) one in which one or more of the amino acid residues includes a substituent group, or (iii) one in which the additional amino acids are fused to the mature polypeptide, such as a leader or auxiliary sequence which is employed for purification of the polypeptide. Such fragments, derivatives, variants and analogues are deemed to be within the scope of those skilled in the art from the teachings herein.

"Oligonucleotides" are short-length, single- or double-stranded polydeoxynucleotides that are chemically synthesized by known methods (such as phosphotriester, phosphite, or phosphoramidite chemistry, using solid-phase techniques). Further methods include the polymerase chain reaction (PCR) used if the entire nucleic acid sequence of the gene is known, or the sequence of the nucleic acid complementary to the coding strand is available. Alternatively, if the target amino acid sequence is known, one may infer potential nucleic acid sequences using known and preferred coding residues for each amino acid residue. The oligonucleotides can be purified on polyacrylamide gels or molecular sizing columns or by precipitation. DNA is "purified" when the DNA is separated from non-nucleic acid impurities (which may be polar, non-polar, ionic, etc.).

A "source" or "template" VNAR", as used herein, refers to a VNAR or VNAR antigen binding fragment whose antigen binding sequence serves as the template sequence upon which diversification according to the criteria described herein is performed. An antigen binding sequence generally includes within a VNAR preferably at least one CDR, preferably including framework regions.

A "transcription regulatory element" will contain one or more of the following components: an enhancer element, a promoter, an operator sequence, a repressor gene, and a transcription termination sequence.

"Transformation" means a process whereby a cell takes up DNA and becomes a "transformant". The DNA uptake may be permanent or transient. A "transformant" is a cell which has taken up and maintained DNA as evidenced by the expression of a phenotype associated with the DNA (e.g., antibiotic resistance conferred by a protein encoded by the DNA).

A "variant" or "mutant" of a starting or reference polypeptide (for example, a source VNAR or a CDR thereof), such as a fusion protein (polypeptide) or a heterologous polypeptide (heterologous to a phage), is a polypeptide that (1) has an amino acid sequence different from that of the starting or reference polypeptide and (2) was derived from the starting or reference polypeptide through either natural or artificial mutagenesis. Such variants include, for example, deletions from, and/or insertions into and/or substitutions of, residues within the amino acid sequence of the polypeptide of interest. For example, a fusion polypeptide of the invention generated using an oligonucleotide comprising a non-random codon set that encodes a sequence with a variant amino acid (with respect to the amino acid found at the corresponding position in a source VNAR or antigen binding fragment) would be a variant polypeptide with respect to a source VNAR or antigen binding fragment. Thus, a variant CDR refers to a CDR comprising a variant sequence with respect to a starting or reference polypeptide sequence (such as that of a source VNAR or antigen binding fragment). A variant amino acid, in this context, refers to an amino acid different from the amino acid at the corresponding position in a starting or reference polypeptide sequence (such as that of a source VNAR or antigen binding fragment). Any combination of deletion, insertion, and substitution may be made to arrive at the final variant or mutant construct, provided that the final construct possesses the desired functional characteristics. The amino acid changes also may alter post-translational processes of the polypeptide, such as changing the number or position of glycosylation sites.

A "wild-type" or "reference" sequence or the sequence of a "wild-type" or "reference" protein/polypeptide, such as a coat protein, or a CDR of a source VNAR, may be the reference sequence from which variant polypeptides are derived through the introduction of mutations. In general, the "wild-type" sequence for a given protein is the sequence that is most common in nature. Similarly, a "wild-type" gene sequence is the sequence for that gene which is most commonly found in nature. Mutations may be introduced into a "wild-type" gene (and thus the protein it encodes) either through natural processes or through man induced means. The products of such processes are "variant" or "mutant" forms of the original "wild-type" protein or gene.

A "humanised" antigen specific antigen binding molecule may be modified at one or more amino acid sequence position to reduce the potential for immunogenicity in vivo, while retaining functional binding activity for the specific epitopes on the specific antigen.

Humanization of antibody variable domains is a technique well-known in the art to modify an antibody which has been raised, in a species other than humans, against a therapeutically useful target so that the humanized form may avoid unwanted immunological reaction when administered to a human subject. The methods involved in humanization are summarized in Almagro J. C and William Strohl W. *Antibody Engineering: Humanization, Affinity Maturation, and Selection Techniques in Therapeutic Monoclonal Antibodies: From Bench to Clinic*. Edited by An J. 2009 John Wiley & Sons, Inc and in Strohl W. R. and Strohl L. M., *Therapeutic Antibody Engineering*, Woodhead Publishing 2012.

Although IgNARs have distinct origins compared to immunoglobulins and have very little sequence homology compared to immunoglobulin variable domains there are some structural similarities between immunoglobulin and IgNAR variable domains, so that similar processes can be applied to the VNAR domain. For example, WO2013/167883, incorporated by reference, provides a description of the humanization of VNARs, see also Kovalenko O. V., et al. J Biol Chem. 2013. 288(24): p. 17408-19.

A humanised antigen specific binding molecule may differ from a wild-type antigen specific binding molecule by substituting one or more framework amino acid residues with a corresponding framework amino acid residue of DPK-9. DPK-9 is a human germline VL scaffold, a member of the variable kappa subgroup 1 (VK1). DPK-9 has a sequence according to:

(SEQ ID NO: 40)
DIQMTQSPSSLSASVGDRVTITCRASQSISSYLNWYQQKPGKAPKLLIY

AASSLQSGVPSRFSGSGSGTDFTLTISSLQPEDFATYYCQQSYSTPNTF

GQGTKVEIK

The sequences of VNARs and DPK-9 may be aligned as illustrated in (FIG. 1).

Library Diversity

Amino acid positions in the CDR regions CDR1 and CDR3 can be each mutated using a non-random codon set encoding the commonly occurring amino acids at each position. In some embodiments, when a position in a CDR region is to be mutated, a codon set is selected that encodes preferably at least about 50%, preferably at least about 60%, preferably at least about 70%, preferably at least about 80%, preferably at least about 90%, preferably all the amino acids for that position. In some embodiments, when a position in a CDR region is to be mutated, a codon set is selected that encodes preferably from about 50% to about 100%, preferably from about 60% to about 95%, preferably from at least about 70% to about 90%, preferably from about 75% to about 90% of all the amino acids for that position.

The diversity of the library of the VNARs is designed to maximize diversity while minimizing structural perturbations of the VNAR to provide for increased ability to isolate high affinity antigen specific antigen binding molecules and to provide for such molecules that can be produced in high yield in cell culture. The number of positions mutated in the VNAR variable domain is minimized and the variant amino acids at each position are designed to include the commonly occurring amino acids at each position with the exception of cysteine, while suitably (where possible) excluding uncommonly occurring amino acids and stop codons.

The diversity in the library is designed by mutating those positions in at least one CDR using nonrandom codon sets. The nonrandom codon set preferably encodes at least a subset of the commonly occurring amino acids at those positions while minimizing non-target sequences such as cysteine and stop codons.

The nonrandom codon set for each position preferably encodes at least two amino acids and does not encode cysteine. Non-target amino acids at each position are minimized and cysteines and stop codons are generally and preferably excluded because they can adversely affect the structure.

As discussed above, the variant amino acids are encoded by nonrandom codon sets. A codon set is a set of different nucleotide triplet sequences which can be used to form a set of oligonucleotides used to encode the desired group of amino acids. A set of oligonucleotides can be synthesized, for example, by solid phase synthesis, containing sequences that represent all possible combinations of nucleotide triplets provided by the codon set and that will encode the desired group of amino acids. Synthesis of oligonucleotides with selected nucleotide "degeneracy" at certain positions is a standard procedure.

Such sets of nucleotides having certain codon sets can be synthesized using commercial nucleic acid synthesizers (available from, for example, Applied Biosystems, Foster City, CA), or can be obtained commercially (for example, from Gene Link Inc, Hawthorn, NY, or Life Technologies, Rockville, MD). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

In one embodiment, a polypeptide having a variant CDR1 and CDR3, or mixtures thereof is formed, wherein at least one variant CDR comprises a variant amino acid in at least one amino acid position, wherein the variant amino acid is encoded by a nonrandom codon set, and wherein at least 70% of the amino acids encoded by the nonrandom codon set are target amino acids for that position in known variable domain sequences.

Methods of substituting an amino acid of choice into a template nucleic acid are well established in the art, some of which are described herein. For example, libraries can be created by targeting amino acid positions in at least one CDR region for amino acid substitution with variant amino acids using the Kunkel method (Kunkel et al., Methods Enzymol. (1987), 154, 367-382).

A codon set is a set of different nucleotide triplet sequences used to encode desired variant amino acids. Codon sets can be represented using symbols to designate particular nucleotides or equimolar mixtures of nucleotides as shown in below according to the IUB code. Typically, a codon set is represented by three capital letters e.g. RRK, GST, TKG, TWC, KCC, KCT, and TRM.

Iub Codes
  G Guanine
  A Adenine
  T Thymine
  C Cytosine
  R (A or G)
  Y (C or T)
  M (A or C)
  K (G or T)
  S (C or G)
  W (A or T)
  H (A or C or T)
  B (C or G or T)
  V (A or C or G)
  D (A or G or T)
  N (A or C or G or T)

Oligonucleotide or primer sets can be synthesized using standard methods. A set of oligonucleotides can be synthesized, for example, by solid phase synthesis, containing sequences that represent all possible combinations of nucleotide triplets provided by the codon set and that will encode the desired group of amino acids.

Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, CA), or can be obtained commercially (for example, from Gene Link Inc, Hawthorn NY, or Life Technologies, Rockville, MD). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

In one method, nucleic acid sequences encoding variant amino acids can be created by oligonucleotide-mediated mutagenesis of a nucleic acid sequence encoding a source or template polypeptide such as the VNAR sequence D1 or C4 disclosed herein. This technique is well known in the art as described by Zoller et al. Nucleic Acids Res. (1987), 10, 6487-6504 (1987). Briefly, nucleic acid sequences encoding variant amino acids are created by hybridizing an oligonucleotide set encoding the desired codon sets to a DNA template, where the template is the single-stranded form of the plasmid containing a variable region nucleic acid template sequence. After hybridization, DNA polymerase is used to synthesize an entire second complementary strand of the template that will thus incorporate the oligonucleotide primer, and will contain the codon sets as provided by the oligonucleotide set.

Nucleic acids encoding other source or template molecules are known or can be readily determined. Generally, oligonucleotides of at least 25 nucleotides in length are used. An optimal oligonucleotide will have 12 to 15 nucleotides that are completely complementary to the template on either side of the nucleotide(s) coding for the mutation(s). This ensures that the oligonucleotide will hybridize properly to the single-stranded DNA template molecule. The oligonucleotides are readily synthesized using techniques known in the art such as that described by Crea et al., Proc. Nat'l. Acad. Sci. USA, (1987) 75: 5765).

The DNA template can be generated by those vectors that are either derived from bacteriophage M13 vectors (the commercially available M13mpl8 and M13mpl9 vectors are suitable), or those vectors that contain a single-stranded phage origin of replication as described by Viera et al., Methods Enzymol., (1987) 153, 3). Thus, the DNA that is to be mutated can be inserted into one of these vectors in order to generate single-stranded template.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of coding sequence 1, and the other strand (the original template) encodes the native, unaltered sequence of coding sequence 1. This heteroduplex molecule is then transformed into a suitable host cell, usually a prokaryote such as E. coli JM101. After growing the cells, they are plated onto agarose plates and screened using the oligonucleotide primer radiolabelled with a $^{32}$-Phosphate to identify the bacterial colonies that contain the mutated DNA.

The method described immediately above may be modified such that a homoduplex molecule is created wherein both strands of the plasmid contain the mutation(s). The modifications are as follows: The single stranded oligonucleotide is annealed to the single-stranded template as described above. A mixture of three deoxyribonucleotides, deoxyriboadenosine (dATP), deoxyriboguanosine (dGTP), and deoxyribothymidine (dTT), is combined with a modified thiodeoxyribocytosine called dCTP- (aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP- (aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site (s) to be mutagenized. The reaction is then stopped to leave a molecule that is only partially single-stranded.

A complete double-stranded DNA homoduplex is then formed using DNA polymerase in the presence of all four deoxyribonucleotide triphosphates, ATP, and DNA ligase. This homoduplex molecule can then be transformed into a suitable host cell.

As indicated previously the sequence of the oligonucleotide set is of sufficient length to hybridize to the template nucleic acid and may also, but does not necessarily, contain restriction sites. The DNA template can be generated by those vectors that are either derived from bacteriophage M13 vectors or vectors that contain a single-stranded phage origin of replication as described by Viera et al. (Meth. Enzymol. (1987), 153, 3). Thus, the DNA that is to be mutated must be inserted into one of these vectors in order to generate a single-stranded template.

Oligonucleotide sets can be used in a polymerase chain reaction using a nucleic acid template sequence as the template to create nucleic acid cassettes. The nucleic acid template sequence can be any portion of a VNAR molecule (i.e., nucleic acid sequences encoding amino acids targeted for substitution). The nucleic acid template sequence is a portion of a double stranded DNA molecule having a first nucleic acid strand and complementary second nucleic acid strand. The nucleic acid template sequence contains at least a portion of a VNAR domain and has at least one CDR. In some cases, the nucleic acid template sequence contains more than one CDR. An upstream portion and a downstream portion of the nucleic acid template sequence can be targeted for hybridization with members of an upstream oligonucleotide set and a downstream oligonucleotide set.

A first oligonucleotide of the upstream primer set can hybridize to the first nucleic acid strand and a second oligonucleotide of the downstream primer set can hybridize to the second nucleic acid strand. The oligonucleotide primers can include one or more codon sets and be designed to hybridize to a portion of the nucleic acid template sequence. Use of these oligonucleotides can introduce two or more codon sets into the PCR product (i.e., the nucleic acid cassette) following PCR. The oligonucleotide primer that hybridizes to regions of the nucleic acid sequence encoding the VNAR domain includes portions that encode CDR residues that are targeted for amino acid substitution.

The upstream and downstream oligonucleotide sets can also be synthesized to include restriction sites within the oligonucleotide sequence. These restriction sites can facilitate the insertion of the nucleic acid cassettes (i.e., PCR reaction products) into an expression vector having additional VNAR sequences.

Protein Expression

Nucleic acid sequences encoding antigen specific antigen binding molecules of the invention may be present in a nucleic acid construct. Such nucleic acid constructs may be in the form of a vector, for example, an expression vector, and may include, among others, chromosomal, episomal and virus-derived vectors, for example, vectors derived from bacterial plasmids, from bacteriophage, from transposons, from yeast episomes, from insertion elements, from yeast chromosomal elements, from viruses such as baculo-viruses, papova-viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. Generally, any vector suitable to maintain, propagate or express nucleic acid to express a polypeptide in a host, may be used for expression in this regard.

The nucleic acid construct may suitably include a promoter or other regulatory sequence which controls expression of the nucleic acid. Promoters and other regulatory sequences which control expression of a nucleic acid have been identified and are known in the art. The person skilled in the art will note that it may not be necessary to utilise the whole promoter or other regulatory sequence. Only the minimum essential regulatory element may be required and, in fact, such elements can be used to construct chimeric sequences or other promoters. The essential requirement is, of course, to retain the tissue and/or temporal specificity. The promoter may be any suitable known promoter, for example, the human cytomegalovirus (CMV) promoter, the CMV immediate early promoter, the HSV thymidine kinase, the early and late SV40 promoters or the promoters of retroviral LTRs, such as those of the Rous Sarcoma virus (RSV) and metallothionine promoters such as the mouse metallothionine-I promoter. The promoter may comprise the minimum comprised for promoter activity (such as a TATA element, optionally without enhancer element) for example, the minimum sequence of the CMV promoter. Preferably, the promoter is contiguous to the nucleic acid sequence.

As stated herein, the nucleic acid construct may be in the form of a vector. Vectors frequently include one or more expression markers which enable selection of cells transfected (or transformed) with them, and preferably, to enable a selection of cells containing vectors incorporating heterologous DNA. A suitable start and stop signal will generally be present.

The vector may be any suitable expression vector, such as pET. The vector may include such additional control sequences as desired, for example selectable markers (e.g. antibiotic resistance, fluorescence, etc.), transcriptional control sequences and promoters, including initiation and termination sequences.

The promoter may be any suitable promoter for causing expression of the protein encoded by a nucleic acid sequence of the invention, e.g. a CMV promoter, human phosphoglycerate kinase (hPGK) promoter.

Such vectors may be present in a host cell. Representative examples of appropriate host cells for expression of the nucleic acid construct of the invention include virus packaging cells which allow encapsulation of the nucleic acid into a viral vector; bacterial cells, such as Streptococci, Staphylococci, *E. coli, Streptomyces* and *Bacillus subtilis*; single cells, such as yeast cells, for example, *Saccharomyces cerevisiae*, and *Aspergillus* cells; insect cells such as *Drosophila* S2 and *Spodoptera* Sf9 cells, animal cells such as CHO, COS, C127, 3T3, PHK.293, and Bowes Melanoma cells and other suitable human cells; and plant cells e.g. *Arabidopsis thaliana*. Suitably, the host cell is a eukaryotic cell, such as a CHO cell or a HEK293 cell.

Introduction of an expression vector into the host cell can be achieved by calcium phosphate transfection, DEAE-dextran mediated transfection, microinjection, cationic—lipid-mediated transfection, electroporation, transduction, scrape loading, ballistic introduction, infection or other methods. Such methods are described in many standard laboratory manuals, such as Sambrook et al, Molecular Cloning, a Laboratory Manual, Second Edition, Cold Spring Harbor Laboratory Press, Cold Spring Harbor, N.Y. (1989).

Mature proteins can be expressed in host cells, including mammalian cells such as CHO cells, yeast, bacteria, or other cells under the control of appropriate promoters. Cell-free translation systems can be employed to produce such proteins using RNAs derived from the nucleic acid construct of the third aspect of the present invention. Appropriate cloning and expression vectors for use with prokaryotic and eukaryotic hosts are described by Sambrook et al, Molecular Cloning, a Laboratory Manual, Second Edition, Cold Spring Harbor Laboratory Press, Cold Spring Harbor, N.Y. (1989).

The invention also provides a host cell comprising any of the polynucleotides and/or vectors of the invention described herein. According to the invention, there is provided a process for the production of an antigen specific antigen binding molecule of the invention, comprising the step of expressing a nucleic acid sequence encoding said molecule in a suitable host cell as defined herein.

Proteins can be recovered and purified from recombinant cell cultures by standard methods including ammonium sulphate or ethanol precipitation, acid extraction, anion or cation exchange chromatography, phosphocellulose chromatography, hydrophobic interaction chromatography, affinity chromatography, hydroxyapatite chromatography, lectin and/or heparin chromatography. For therapy, the nucleic acid construct, e.g. in the form of a recombinant vector, may be purified by techniques known in the art, such as by means of column chromatography as described in Sambrook et a, Molecular Cloning, a Laboratory Manual, Second Edition, Cold Spring Harbor Laboratory Press, Cold Spring Harbor, N.Y. (1989).

The invention also extends to a fusion protein comprising an antigen specific antigen binding molecule defined herein. The antigen specific antigen binding molecule is fused to a biologically active protein. The invention also extends to a nucleic acid encoding an antigen specific antigen binding molecule disclosed herein, or a fusion protein thereof.

This aspect of the invention therefore extends to processes for preparing a fusion protein of the invention comprising production of the fusion protein recombinantly by expression in a host cell, purification of the expressed fusion protein by means of peptide bond linkage, hydrogen or salt bond or chemical cross linking. In some embodiments of this aspect of the invention, the fusion protein could be prepared using hydrogen or salt bonds where the peptide is capable or multimerisation, for example dimerisation or trimerisation.

Protein Expression as a Library

In another aspect, the invention provides a library comprising a plurality of vectors of the invention, wherein the plurality of vectors encode a plurality of polypeptides. Accordingly, the invention provides a virus or viral particle (such as phage or phagemid particles) displaying a polypeptide of the invention on its surface. The invention also provides a library comprising a plurality of the viruses or viral particles of the invention, each virus or virus particle displaying a polypeptide of the invention. A library of the invention may comprise any number of distinct polypeptides (sequences), at least about $1\times10^8$, at least about $1\times10^9$, at least about $1\times10^{10}$ distinct sequences, more suitably at least about 9×10$^{10}$ sequences. The invention also provides libraries containing a plurality of polypeptides, wherein each type of polypeptide is a polypeptide of the invention as described herein.

Nucleic acid cassettes can be cloned into any suitable vector for expression of a portion or the entire VNAR containing the targeted amino acid substitutions generated. The nucleic acid cassette can be cloned into a vector allowing production of a portion or the entire VNAR chain sequence fused to all or a portion of a viral coat protein (i.e., creating a fusion protein) and displayed on the surface of a particle or cell. While several types of vectors are available and may be used to practice this invention, phagemid vectors are the preferred vectors for use herein, as they may be constructed with relative ease, and can be readily amplified. Phagemid vectors generally contain a variety of components including promoters, signal sequences, phenotypic selection genes, origin of replication sites, and other necessary components.

In another embodiment, wherein a particular variant amino acid combination is to be expressed, the nucleic acid cassette contains a sequence that is able to encode all or a portion of the VNAR sequence, and is able to encode the variant amino acid combinations. For production of antigen specific antigen binding molecules containing these variant amino acids or combinations of variant amino acids, as in a library, the nucleic acid cassettes can be inserted into an expression vector containing additional VNAR sequence, for example all or portions of the various CDR, Framework and/or Hypervariable regions. These additional sequences can also be fused to other nucleic acids sequences, such as sequences which encode viral coat protein components and therefore allow production of a fusion protein.

One aspect of the invention includes a replicable expression vector comprising a nucleic acid sequence encoding a gene fusion, wherein the gene fusion encodes a fusion protein comprising a VNAR sequence and a second VNAR sequence, fused to all or a portion of a viral coat protein. Also included is a library of diverse replicable expression vectors comprising a plurality of gene fusions encoding a plurality of different fusion proteins including a plurality of VNAR sequences generated with diverse sequences as described above. The vectors can include a variety of components and are preferably constructed to allow for movement of VNAR sequences between different vectors and/or to provide for display of the fusion proteins in different formats.

Examples of vectors include phage vectors. The phage vector has a phage origin of replication allowing phage replication and phage particle formation. The phage is preferably a filamentous bacteriophage, such as an M13, fl, fd, Pf3 phage or a derivative thereof, or a lambdoid phage, such as lambda, 21, phi80, phi81, 82, 424, 434, etc., or a derivative thereof.

Examples of viral coat proteins include infectivity protein PIII, major coat protein PVIII, p3, Soc (T4), Hoc (T4), gpD (of bacteriophage lambda), minor bacteriophage coat protein 6 (pVI) (filamentous phage; Hufton et al, J Immunol Methods. (1999), 231, (1-2): 39-51), variants of the M13 bacteriophage major coat protein (P8) (Weiss et al, Protein Sci (2000) 9 (4): 647-54). The fusion protein can be displayed on the surface of a phage and suitable phage systems include M13K07 helper phage, M13R408, M13-VCS, and Phi X 174, pJuFo phage system (Pereboev at al J Virol. (2001); 75(15): 7107-13), and hyperphage (Rondot et al Nat Biotechnol. (2001); 19(1): 75-8). The preferred helper phage is M13K07, and the preferred coat protein is the M13 Phage gene III coat protein. The preferred host is E. coli, and protease deficient strains of E. coli. Vectors, such as the fth1 vector (Enshell-Seijffers et al, Nucleic Acids Res. (2001); 29(10): E50-0) can be useful for the expression of the fusion protein.

The expression vector also can have a secretory signal sequence fused to the DNA encoding each VNAR or fragment thereof. This sequence is typically located immediately 5' to the gene encoding the fusion protein, and will thus be transcribed at the amino terminus of the fusion protein. However, in certain cases, the signal sequence has been demonstrated to be located at positions other than 5' to the gene encoding the protein to be secreted. This sequence targets the protein to which it is attached across the inner membrane of the bacterial cell. The DNA encoding the signal sequence may be obtained as a restriction endonuclease fragment from any gene encoding a protein that has a signal sequence. Suitable prokaryotic signal sequences may be obtained from genes encoding, for example, LamB or OmpF (Wong et al, Gene, (1983) 68, 1931), MalE, PhoA and other genes.

A preferred prokaryotic signal sequence for practicing this invention is the E. coli heat-stable enterotoxin II (STII) signal sequence as described by Chang et al (Gene 55. 189 (1987)), and malE.

The vector also typically includes a promoter to drive expression of the fusion protein. Promoters most commonly used in prokaryotic vectors include the lac Z promoter system, the alkaline phosphatase pho A promoter (Ap), the bacteriophage XPL promoter (a temperature sensitive promoter), the tac promoter (a hybrid trp-lac promoter that is regulated by the lac repressor), the tryptophan promoter, and the bacteriophage T7 promoter. For general descriptions of promoters, see section 17 of Sambrook et al. supra. While these are the most commonly used promoters, other suitable microbial promoters may be used as well.

The vector can also include other nucleic acid sequences, for example, sequences encoding gD tags, c-Myc epitopes, poly-histidine tags, fluorescence proteins (e.g., GFP), or beta-galactosidase protein which can be useful for detection or purification of the fusion protein expressed on the surface of the phage or cell.

Nucleic acid sequences encoding, for example, a gD tag, also provide for positive or negative selection of cells or virus expressing the fusion protein. In some embodiments, the gD tag is preferably fused to a VNAR sequence which is not fused to the viral coat protein component. Nucleic acid sequences encoding, for example, a polyhistidine tag, are useful for identifying fusion proteins including VNAR sequences that bind to a specific antigen using immunohistochemistry. Tags useful for detection of antigen binding can be fused to either a VNAR sequence not fused to a viral coat protein component or a VNAR sequence fused to a viral coat protein component.

Another useful component of the vectors used to practice this invention is phenotypic selection genes. Typical phenotypic selection genes are those encoding proteins that confer antibiotic resistance upon the host cell. By way of illustration, the ampicillin resistance gene (Amp$^r$), and the tetracycline resistance gene (Tetr) are readily employed for this purpose.

The vector can also include nucleic acid sequences containing unique restriction sites and suppressible stop codons. The unique restriction sites are useful for moving VNAR sequences between different vectors and expression systems. The suppressible stop codons are useful to control the level of expression of the fusion protein and to facilitate purification of soluble VNAR fragments. For example, an amber stop codon can be read as Gln in a supE host to enable phage display, while in a non-supE host it is read as a stop codon to produce soluble VNAR fragments without fusion to phage coat proteins. These synthetic sequences can be fused to one or more VNAR sequences in the vector.

It may be convenient to use vector systems that allow the nucleic acid encoding a sequence of interest, for example a CDR having variant amino acids, to be easily removed from the vector system and placed into another vector system. For example, appropriate restriction sites can be engineered in a vector system to facilitate the removal of the nucleic acid sequence encoding a VNAR. The restriction sequences are usually chosen to be unique in the vectors to facilitate efficient excision and ligation into new vectors. VNAR sequences can then be expressed from vectors without extraneous fusion sequences, such as viral coat proteins or other sequence tags.

Between nucleic acid encoding VNAR sequences (gene 1) and the viral coat protein component (gene 2), DNA encoding a termination or stop codon may be inserted, such termination codons including UAG (amber), UAA (ocher) and UGA (opel). (Microbiology, Davis et al., Harper & Row, New York, 1980, pp. 237, 245-47 and 374). The termination or stop codon expressed in a wild type host cell results in the synthesis of the gene 1 protein product without the gene 2 protein attached. However, growth in a suppressor host cell results in the synthesis of detectable quantities of fused protein. Such suppressor host cells are well known and described, such as E. coli suppressor strain (Bullock et al., BioTechniques 5: 376-379 (1987)). Any acceptable method may be used to place such a termination codon into the mRNA encoding the fusion polypeptide.

The suppressible codon may be inserted between the first gene encoding a VNAR sequence, and a second gene encoding at least a portion of a phage coat protein. Alternatively, the suppressible termination codon may be inserted adjacent to the fusion site by replacing the last amino acid triplet in the VNAR sequence or the first amino acid in the phage coat protein. The suppressible termination codon may be located at or after the C-terminal end of a dimerization domain. When the plasmid containing the suppressible codon is grown in a suppressor host cell, it results in the detectable production of a fusion polypeptide containing the polypeptide and the coat protein. When the plasmid is grown in a non-suppressor host cell, the VNAR sequence is synthesized substantially without fusion to the phage coat protein due to termination at the inserted suppressible triplet UAG, UAA, or UGA. In the non-suppressor cell the antibody variable domain is synthesized and secreted from the host cell due to the absence of the fused phage coat protein which otherwise anchored it to the host membrane.

In some embodiments, the CDR being diversified (randomized) may have a stop codon engineered in the template sequence (referred to herein as a "stop template"). This feature provides for detection and selection of successfully diversified sequences based on successful repair of the stop codon(s) in the template sequence due to incorporation of the oligonucleotide (s) comprising the sequence(s) for the variant amino acids of interest.

Multi-Domain Antigen Specific Antigen Binding Molecules of the Invention

In a further aspect, the invention provides a multi-domain antigen specific antigen binding molecule comprising two or more VNAR domains, wherein each VNAR domain comprises an amino acid sequence having a peptide domain structure represented by the following formula (I):

FW1-CDR1-FW2-HV2-FW3a-HV4-FW3b-CDR3-FW4 wherein FW1 of at least one VNAR binding domain comprises a humanised sequence according to -/D A/I/T S/Q/R V/M N/T/D Q S P S S L S A S V G D R V T I T C V L/T/R D/G T/A/S (SEQ ID NO: 1)

and wherein FW4 of at least one VNAR domain comprises a sequence corresponding to FW4 from a member of a species in the Elasmobranchii subclass, or an amino acid sequence with either
(i) at least 70% identity thereto, or
(ii) one, two, or three amino acid substitutions relative thereto.

The effect of maintaining an FW4 sequence from or related to (as defined above) a sequence corresponding to FW4 from a member of a species in the Elasmobranchii subclass whilst adopting a humanised FW1 sequence may be equivalent or slightly increased neutralising potency compared to a corresponding multi-domain antigen specific antigen binding molecule where FW4 is also humanised.

This effect may be seen even when the neutralising potency of the molecule where FW4 is humanised is high (around 0.002 nM). The inventors have surprisingly identified that this effect is unpredictably related to humanisation of FW1 and not FW4 but not to humanisation of FW4 and not FW1. Humanisation of FW4 and not FW1 may markedly impair neutralising potency.

Features of the invention disclosed in connection with the methods of the first, second and third aspects of the invention may be used in defining the invention disclosed in connection with the multi-domain antigen specific antigen binding molecule of the fourth aspect of the invention and vice versa.

The two or more VNAR domains may be the same or may be different. Typically, the multi-domain antigen specific binding molecule comprises at least two different VNAR domains. The two different VNAR domains may share some sequence identity, for example at least 50%, at least 60%, at least 70%, at least 80%, at least 90% or at least 95% sequence identity. The two different VNAR domains may share the same sequence for one or more domains selected from the group consisting of FW1, CDR1, FW2, HV2, FW3a, HV4, FW3b, CDR3 and FW4. Typically, the two different VNAR domains share the same sequence for at least FW1 and FW4. The two different VNAR domains may share the same sequence for CDR1, HV2, HV4 and CDR3. The two different VNAR domains may share the same sequence for FW1, FW2, CDR1, HV2, HV4 and CDR3.

Typically, the FW1 of the two or more VNAR binding domains each comprises a humanised sequence according to -/D A/I/T S/Q/R V/M N/T/D Q S P S S L S A S V G D R V T I T C V L/V T/R D/G T/A/S (SEQ ID NO: 1).

Typically, the FW4 of the two or more VNAR binding domains each comprises a sequence corresponding to FW4 from a member of a species in the Elasmobranchii subclass, or an amino acid sequence with either
(i) at least 70% identity thereto, or
(ii) one, two, or three amino acid substitutions relative thereto.

In one embodiment, the multi-domain antigen specific antigen binding molecule comprises two or more VNAR domains, wherein each VNAR domain comprises an amino acid sequence having a peptide domain structure represented by the following formula (I):

FW1-CDR1-FW2-HV2-FW3a-HV4-FW3b-CDR3-FW4 wherein FW1 of at least one VNAR binding domain comprises a humanised sequence according to –/D A/I/T S/Q/R V/M N/T/D Q S P S S L S A S V G D R V T I T C V L T/R D/G T/A/S (SEQ ID NO: 1)
and wherein FW4 of at least one VNAR domain comprises a sequence corresponding to FW4 from a member of a species in the Elasmobranchii subclass.

In one embodiment, the multi-domain antigen specific antigen binding molecule comprises two or more VNAR domains, wherein each VNAR domain comprises an amino acid sequence having a peptide domain structure represented by the following formula (I):

FW1-CDR1-FW2-HV2-FW3a-HV4-FW3b-CDR3-FW4 wherein FW1 of at least two VNAR binding domains comprises a humanised sequence according to –/D A/I/T S/Q/R V/M N/T/D Q S P S S L S A S V G D R V T I T C V L/V T/R D/G T/A/S (SEQ ID NO: 1)
and wherein FW4 of at least two VNAR domains comprises a sequence corresponding to FW4 from a member of a species in the Elasmobranchii subclass.

In one embodiment, at least one of FW1, FW2, FW3a, FW3b and FW4 each comprise one or more sequences selected from the group consisting of:
FW1 comprises a sequence selected from the group consisting of:

```
                                         (SEQ ID NO: 8)
ARVDQSPSSLSASVGDRVTITCVLRDS;

(SEQ ID NO: 6)
A/T S/R V N/D Q S P S S L S A S V G D R V T I T
C V L A V T D/G T/A;
and (SEQ ID NO: 7)
D I Q M T Q S P S S L S A S V G D R V T I T C
VL/VT D/G T/A;
```

FW2 comprises a sequence according to T S/Y W F/Y R/Q K/Q N/K P/S G T/S (SEQ ID NO: 2);
FW3a comprises a sequence according to G R Y/F V/S E/G S/T V/G/I N/S (SEQ ID NO: 3);
FW3b comprises a sequence according to F S/T L R/T I K/S/N D/S L T/Q V/P A/E D S/F A/G T Y Y/R/I C K/R/A A/S/L (SEQ ID NO: 4), and
FW4 comprises a sequence according to YGGGTVVTVN (SEQ ID NO: 21) or an amino acid sequence with either
(i) at least 70% identity thereto, or
(ii) one, two, or three amino acid substitutions relative thereto.

FW1 may comprise a sequence selected from the group consisting of:

```
                                         (SEQ ID NO: 8)
ARVDQSPSSLSASVGDRVTITCVLRDS;

(SEQ ID NO: 6)
A/T S/R V N/D Q S P S S L S A S V G D R V T I T C
V L/V T D/G T/A;
and (SEQ ID NO: 7)
D I Q M T Q S P S S L S A S V G D R V T I T C V
L/V T D/G T/A.
```

FW2 may comprise a sequence according to T S/Y W F/Y R/Q K/Q N/K P/S G T/S (SEQ ID NO: 2).

FW3a may comprise a sequence according to G R Y/F V/S E/G S/T V/G/I N/S (SEQ ID NO: 3).

FW3b may comprise a sequence according to F S/T L R/T I K/S/N D/S L T/Q V/P A/E D S/F A/G T Y Y/R/I C K/R/A A/S/L (SEQ ID NO: 4).

The amino acid sequence may have at least 70%, 75%, 80%, 85%, 90% and still more preferably 95% (still more preferably at least 96%, 97%, 98% or 99%) identity to an FW4 sequence from a member of a species in the Elasmobranchii subclass.

The amino acid sequence may have three, preferably two, or more preferably one amino acid substitution relative to an FW4 sequence from a member of a species in the Elasmobranchii subclass. The one or more substitutions may be conservative amino acid substitutions.

Sequence identity and/or amino acid substitutions may be relative to any FW4 sequence of any species in the Elasmobranchii subclass. For example, sequence identity and/or amino acid substitutions may be relative to an FW4 sequence from *Ginglymostoma cirratum*, from the family Ginglymostomatidae, of the order Orectolobformes and/or *Squalus acanthias* from the family Squalidae, of the order Squaliformes. Sequence identity and/or amino acid substitutions may be relative to YGGGTVVTVN (SEQ ID NO: 21).

FW4 may comprise a sequence according to YGGGTVVTVN (SEQ ID NO: 21) or an amino acid sequence with either
(i) at least 70% identity thereto, or
(ii) one, two, or three amino acid substitutions relative thereto.

FW4 may comprise a sequence according to YGGGTVVVN (SEQ ID NO: 21).

At least three amino acid residues from the combined sequences of FW2, FW3a and FW3b may be humanised. Accordingly, starting from the combined sequence of FW2, FW3a and FW3b from a member of a species in the Elasmobranchii subclass at least three amino acid residues may be substituted for corresponding residues from DPK-9. The FW2, FW3a and FW3b sequences may be from the same member of a species in the Elasmobranchii subclass or from two or more different members of a species in the Elasmobranchii subclass, such as different individuals of the same species. Alternatively FW2, FW3a and FW3b sequences may be from two or more different species in the Elasmobranchii subclass.

The at least three humanised residues may be selected from any three humanised residues in any FW2, FW3a and/or FW3b sequences disclosed herein. For example, the at least three humanised residues may be selected from any three humanised residues illustrated in FIG. 1.

At least four, at least five, at least six, at least seven, at least eight, at least nine, at least ten, at least 11, at least 12, at least 13, at least 14 or at least 15 amino acid residues from the combined sequences of FW2, FW3a and FW3b may be humanised.

The one or more sequences for FW2 may be selected from the group consisting of:

TYWYRKKSGS;                              (SEQ ID NO: 11)

T S/Y W F/Y R K N P G T/S;               (SEQ ID NO: 9)
    and

T S/Y WY/F Q Q K P G T/S.                (SEQ ID NO: 10)

The one or more sequences for FW3a may be selected from the group consisting of:

GRYVETVN;                                (SEQ ID NO: 14)

GRYVETIN;                                (SEQ ID NO: 15)

GRYVESVN;                                (SEQ ID NO: 12)
    and

GRFSGSGS.                                (SEQ ID NO: 13)

In one embodiment, FW3a of a first VNAR domain comprises GRYVETVN (SEQ ID NO: 14) and FW3a of a second VNAR domain comprises GRYVETIN (SEQ ID NO: 15).

The one or more sequences for FW3b may be selected from the group consisting of:

FTLTISSLQPEDFATYYCAS;                    (SEQ ID NO: 18)

FSLRINDLTVEDSGTYRCKL;                    (SEQ ID NO: 19)

F S L R I K D L T V A D S A T Y Y/I C K/R A;  (SEQ ID NO: 16)
    and

F T L T I S S L Q P E D F A T Y Y/I C K/R A   (SEQ ID NO: 17)

In one embodiment, FW3b of a first VNAR domain comprises FTLTISSLQPEDFATYYCAS (SEQ ID NO: 18) and FW3b of a second VNAR domain comprises FSLRINDLTVEDSGTYRCKL (SEQ ID NO: 19).

The one or more sequences for FW4 may comprise YGGGTVVTVN (SEQ ID NO: 21).

The one or more sequences for FW1 may comprise ARVDQSPSSLSASVGDRVTITCVLRDS (SEQ ID NO: 8).

In one embodiment, the one or more sequences for FW4 comprises YGGGTVVTVN (SEQ ID NO: 21) and the one or more sequences for FW1 comprises ARVDQSPSSL-SASVGDRVTITCVLRDS (SEQ ID NO: 8).

In one embodiment, the multi-domain antigen specific antigen binding molecule comprises at least two VNAR domains each comprising:
  a sequence for FW4 comprising YGGGTVVTVN (SEQ ID NO: 21), and
  a sequence for FW1 comprises ARVDQSPSSL-SASVGDRVTITCVLRDS (SEQ ID NO: 8).

The multi-domain antigen specific antigen binding molecule may comprise a first VNAR domain and a second VNAR domain wherein FW1 of the firstVNAR domain comprises ARVDQSPSSLSASVGDRVTITCVLRDS (SEQ ID NO: 8);
FW2 of the first VNAR domain comprises TYWYRKKSGS (SEQ ID NO: 11);
FW3a of the first VNAR domain comprises GRYVETVN (SEQ ID NO: 14);
FW3b of the first VNAR domain comprises FTLTISSLQPEDFATYYCAS (SEQ ID NO: 18);
FW4 of the first VNAR domain comprises YGGGTVVTVN (SEQ ID NO: 21);
FW1 of the second VNAR domain comprises ARVDQSPSSLSASVGDRVTITCVLRDS (SEQ ID NO: 8);
FW2 of the second VNAR domain comprises TYWYRKKSGS (SEQ ID NO: 11);
FW3a of the second VNAR domain comprises GRYVETIN (SEQ ID NO: 15);
FW3b of the second VNAR domain comprises FSLRINDLTVEDSGTYRCKL (SEQ ID NO: 19); and
FW4 of the second VNAR domain comprises YGGGTVVTVN (SEQ ID NO: 21).

According to this aspect of the invention, FW1 comprises one or more humanised sequences according to -/D A/I/T S/Q/R V/M N/T/D Q S P S S L S A S V G D R V T I T C V L/V T/R D/G T/A/S (SEQ ID NO: 1). However, in an alternative aspect, the sequence of FW1 is not defined and the library is alternatively characterised by one or more of:
FW2 comprises one or more sequences according to T S/Y W F/Y R/Q K/Q N/K P/S G T/S (SEQ ID NO: 2);
FW3a comprises one or more sequences according to G R Y/F V/S E/G S/T V/G/I N/S (SEQ ID NO: 3); and
FW3b comprises one or more sequences according to F S/T L R/T I K/S/N D/S L T/Q V/P A/E D S/F A/G T Y Y/R/l C K/R/A A/S/L (SEQ ID NO: 4).

In this alternative aspect typically the one or more of FW2, FW3a and FW3b sequences is humanized. The humanised FW2, FW3a and FW3b sequences may be any humanised FW2, FW3a, FW3b and FW4 sequence or sequences disclosed herein.

The present invention relates to VNAR domain sequences that have the capability of being combined into multivalent or multispecific entities and within which multidomain entity each domain retains binding function. The multi-domain antigen specific antigen binding molecule may be a bi- or a multi-valent VNAR.

The multi-domain specific binding molecule may comprise two or more VNAR domains which bind to the same or different epitopes of one or more specific antigens.

In certain preferred embodiments the VNARs in the multi-domain specific binding molecule of the first aspect of the invention bind the same antigen on a specific antigen.

In further preferred embodiments, the VNARs of multi-domain specific binding molecule bind different epitopes on a specific antigen. Multi-domain specific binding molecules in accordance with these embodiments may be termed bi-paratopic molecules, as further described herein.

In one embodiment, specific VNAR binding domain sequences are combined into multivalent or multispecific entities and, within which multidomain entity each domain retains binding function, wherein the binding domains recognize distinct epitopes on a single antigen.

In one embodiment, at least one of the VNAR domains in the multi-domain specific binding molecule exhibits higher binding affinity for its target compared to the monomeric VNAR.

In one embodiment, the at least two VNAR domains bind to the same or different epitopes of one specific antigen.

In one embodiment, the at least two VNAR domains bind to different epitopes of one specific antigen.

In one embodiment, the at least two VNAR domains each bind to a different specific antigen.

A preferred embodiment of the invention is a bi- or multi-specific binding molecule comprising two (or more) different VNAR domains wherein the binding specificity is for distinct epitopes on a single specific antigen and in which the resultant entity shows improved properties compared to the individual VNAR binding domains. An example of an improved property includes increased agonistic or antagonistic effect compared to the monomer VNARs.

Preferably the VNAR domains of the multi-domain specific binding molecule of the present invention are separated by a spacer sequence. More preferably, the spacer sequence has independent functionality which is exhibited in the binding molecule. In one embodiment, the spacer sequence is a VNAR domain or functional fragment thereof. In a specific example the spacer sequence may be the Fc portion of an immunoglobulin, including but not limited to a human immunoglobulin Fc region. The improved properties may partially or completely derive from the properties of the spacer, for example by passively separating the VNAR domains in space or by the inherent properties of a spacer such as serum albumin binding which may lead to a longer in vivo half-life for the resultant entity, or by the recognition of a second therapeutic auto-immune target such as ICOSL or by introduction of a capacity for engagement with cells of the immune system or complement, in the case of immunoglobulin Fc regions.

Embodiments of the multi-domain specific binding molecule of the invention comprising two or more VNAR domains separated by a spacer sequence may be referred to herein as a Quad-X format. Preferably, the multi-domain specific binding molecule comprises two or more VNAR domains separated by a spacer sequence derived from an immunoglobulin Fc region.

In other embodiments, the multi-domain specific binding molecule may further comprise one or more non-VNAR domains. The one or more non-VNAR domains may be placed in any position relative to the VNAR domains. Typically, and in preferred embodiments, the non-VNAR domain will be C-terminal or N-terminal to the VNAR domains.

Embodiments of the multi-domain specific binding molecule of the invention comprising two or more VNAR domains and a non-VNAR domain that is C-terminal or N-terminal to the VNAR domains may be referred to herein as a Quad-Y format.

Exemplary non-VNAR domains include, but are not limited to, TNF R1 and immunoglobulin Fc.

The specific antigen can be from a group comprising a cytokine, a growth factor, an enzyme, a cell surface associated molecule, a cell-surface membrane component, an intracellular molecule, an extracellular matrix component, a stromal antigen, a serum protein, a skeletal antigen, a microbial antigen or an antigen from a normally immune-privileged location.

A further aspect of the invention is the specific combination of VNAR binding domains that recognize cytokines.

Also provided by the present invention are specific domains that recognize human TNF and bind to an epitope that is different from all other well characterized anti-TNF antibody and VHH binders that are currently used to treat disease.

In one embodiment, one or more of the VNAR domains is a TNF-alpha specific VNAR binding domain comprising the following CDRs and hyper-variable regions (HV):

```
CDR1:
                                       (SEQ ID NO: 29)
    HCATSS
    or
                                       (SEQ ID NO: 30)
    NCGLSS
    or
                                       (SEQ ID NO: 31)
    NCALSS

HV2:
                                       (SEQ ID NO: 32)
    TNEESISKG

HV4:
                                       (SEQ ID NO: 33)
    SGSKS
    or
                                       (SEQ ID NO: 34)
    EGSKS

CDR3:
                                       (SEQ ID NO: 35)
    ECQYGLAEYDV
    or
                                       (SEQ ID NO: 36)
    SWWTQNWRCSNSDV
    or
                                       (SEQ ID NO: 37)
    YIPCIDELVYMISGGTSGPIHDV.
```

The multi-domain antigen specific antigen binding molecule may comprise a first VNAR domain and a second VNAR domain wherein:

CDR1 of the first VNAR domain comprises HCATSS (SEQ ID NO: 29);

HV2 of the first VNAR domain comprises TNEESISKG (SEQ ID NO: 32);

HV4 of the first VNAR domain comprises SGSKS (SEQ ID NO: 33);

CDR3 of the first VNAR domain comprises ECQYGLAEYDV (SEQ ID NO: 35);

CDR1 of the second VNAR domain comprises NCGLSS (SEQ ID NO: 30);

HV2 of the second VNAR domain comprises TNEESISKG (SEQ ID NO: 32);

HV4 of the second VNAR domain comprises EGSKS (SEQ ID NO: 34); and

CDR3 of the second VNAR domain comprises SWWTQNWRCSNSDV (SEQ ID NO: 36).

In one embodiment, the first VNAR domain comprises the sequence ARVDQSPSSLSASVGDRVTITCVLRDSHCATSSTYWYRKKSGSTNEESISKGGRYVETVNSGSKSFTL TISSLQPEDFATYYCASECQYGLAEYDVYGGGTVVT/N (SEQ ID NO: 38) and the second VNAR domain comprises the sequence ARVDQSPSSLSASVGDRVTITCVLRDSNCGLSSTYWYRKKSGSTNEESISKGGRYVETINEGSKSFSL RINDLTVEDSGTYRCKLSWWTQNWRCSNSDVYGGGTVVTVN (SEQ ID NO: 39).

In one embodiment the multi-domain antigen specific antigen binding molecule may comprise the sequence:

(SEQ ID NO: 59)
```
ARVDQSPSSLSASVGDRVTITCVLRDSHCATSSTYWYRKKS

GSTNEESISKGGRYVETVNSGSKSFTLTISSLQPEDFATY

YCASECQYGLAEYDVYGGGTVVTVNGSGGGSGGGGSGEPK

SSDKTHTCPPCPAPELLGGPSVFLFPPKPKDTLMISRTPE

VTCVVVDVSHEDPEVKFNWYVDGVEVHNAKTKPREEQYNS

TYRVVSVLTVLHQDWLNGKEYKCKVSNKALPAPIEKTISK

AKGQPREPQVYTLPPSRDELTKNQVSLTCLVKGFYPSDIA

VEWESNGQPENNYKTTPPVLDSDGSFFLYSKLTVDKSRWQ

QGNVFSCSVMHEALHNHYTQKSLSLSPGKGGGGSGGGGSG

GGGSGGGGSGGGGSARVDQSPSSLSASVGDRVTITCVLRD

SNCGLSSTYWYRKKSGSTNEESISKGGRYVETINEGSKSF

SLRINDLTVEDSGTYRCKLSWWTQNWRCSNSDVYGGGTVV

TVN.
```

In preferred embodiments the TNF-alpha specific VNAR domain of the invention is modified at one or more amino acid sequence position to reduce the potential for immunogenicity in vivo, by for example humanization, deimmunization or similar technologies, while retaining functional binding activity for the specific epitopes on the specific antigen.

The TNF-alpha specific VNAR binding domains described herein may be used as one or both VNAR domains in the multi-domain specific binding molecule of the invention.

The antigen specific antigen binding molecule may comprise additional N-terminal or C-terminal sequences which are cleaved off prior to use which may assist in purification and/or isolation during processes for the production of the molecule as described herein. For example, (Ala)$_3$(His)$_6$ at the C-terminal end of the molecule.

Also included within the invention are variants, analogues, derivatives and fragments having the amino acid sequence of the protein in which several e.g. 5 to 10, or 1 to 5, or 1 to 3, 2, 1 or no amino acid residues are substituted, deleted or added in any combination. Especially preferred among these are silent substitutions, additions and deletions, which do not alter the properties and activities of the protein of the present invention. Also especially preferred in this regard are conservative substitutions where the properties of a protein of the present invention are preserved in the variant form compared to the original form. Variants also include fusion proteins comprising an antigen specific antigen binding molecule according to the invention.

As discussed above, an example of a variant of the present invention includes a protein in which there is a substitution of one or more amino acids with one or more other amino acids. The skilled person is aware that various amino acids have similar properties. One or more such amino acids of a substance can often be substituted by one or more other such amino acids without interfering with or eliminating a desired activity of that substance. Such substitutions may be referred to as "non-conservative" amino acid substitutions.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains). Substitutions of this nature are often referred to as "conservative" or "semi-conservative" amino acid substitutions.

Amino acid deletions or insertions may also be made relative to the amino acid sequence for the fusion protein referred to above. Thus, for example, amino acids which do not have a substantial effect on the activity of the polypeptide, or at least which do not eliminate such activity, may be deleted. Such deletions can be advantageous since the overall length and the molecular weight of a polypeptide can be reduced whilst still retaining activity. This can enable the amount of polypeptide required for a particular purpose to be reduced—for example, dosage levels can be reduced.

Amino acid insertions relative to the sequence of the fusion protein above can also be made. This may be done to alter the properties of a substance of the present invention (e.g. to assist in identification, purification or expression, as explained above in relation to fusion proteins).

Amino acid changes relative to the sequence for the fusion protein of the invention can be made using any suitable technique e.g. by using site-directed mutagenesis.

It should be appreciated that amino acid substitutions or insertions within the scope of the present invention can be made using naturally occurring or non-naturally occurring amino acids. Whether or not natural or synthetic amino acids are used, it is preferred that only L-amino acids are present.

A protein according to the invention may have additional N-terminal and/or C-terminal amino acid sequences. Such sequences can be provided for various reasons, for example, glycosylation.

A fusion protein may comprise an antigen specific antigen binding molecule of the present invention fused to a heterologous peptide or protein sequence providing a structural element to the fusion protein.

In other embodiments, the fusion protein may comprise an antigen specific antigen binding molecule of the present invention fused with a molecule having biological activity, i.e. a therapeutic protein having a pharmacologically useful activity. The molecule may be a peptide or protein sequence, or another biologically active molecule.

For example, the antigen specific antigen binding molecule may be fused to a heterologous peptide sequence which may be a poly-amino acid sequence, for example a plurality of histidine residues or a plurality of lysine residues (suitably 2, 3, 4, 5, or 6 residues), or an immunoglobulin domain (for example an Fc domain).

References to heterologous peptides sequences include sequences from other mammalian species, such as murine and human and any heterologous peptides sequences originated from other VNAR domains.

Where the fusion protein comprises an antigen specific antigen binding molecule of the present invention fused with a molecule having biological activity, a biologically active moiety may be a peptide or protein having biological activity such as an enzyme, immunoglobulin, cytokine or a fragment thereof. Alternatively, the biologically active molecule may be an antibiotic, an anti-cancer drug, an NSAID, a steroid, an analgesic, a toxin or other pharmaceutically active agent. Anti-cancer drugs may include cytotoxic or cytostatic drugs.

In some embodiments, the fusion protein may comprise an antigen specific antigen binding molecule of the invention fused to another immunoglobulin variable or constant region, or another antigen specific antigen binding molecule of the invention. In other words, fusions of antigen specific antigen binding molecules of the invention may be of variable length, e.g. dimers, trimers, tetramers, or higher order multimer (i.e. pentamers, hexamers, heptamers octamers, nonamers, or decamers, or greater). In specific embodiments this can be represented as a multimer of monomer VNAR subunits.

For example, where the VNAR CDRs are fused to an additional peptide sequence, the additional peptide sequence can provide for the interaction of one or more fusion polypeptides on the surface of the viral particle or cell. These peptide sequences can therefore be referred to as "dimerization domains". Dimerization domains may comprise at least one or more of a dimerization sequence, or at least one sequence comprising a cysteine residue or both. Suitable dimerization sequences include those of proteins having amphipathic alpha helices in which hydrophobic residues are regularly spaced and allow the formation of a dimer by interaction of the hydrophobic residues of each protein; such proteins and portions of proteins include, for example, leucine zipper regions.

Dimerization domains can also comprise one or more cysteine residues (e.g. as provided by inclusion of an antibody hinge sequence within the dimerization domain). The cysteine residues can provide for dimerization by formation of one or more disulfide bonds. In one embodiment, wherein a stop codon is present after the dimerization domain, the dimerization domain comprises at least one cysteine residue. The dimerization domains are preferably located between the antibody variable or constant domain and the viral coat protein component.

In fusion proteins of the present invention, the antigen specific antigen binding molecule may be directly fused or linked via a linker moiety to the other elements of the fusion protein. The linker may be a peptide, peptide nucleic acid, or polyamide linkage. Suitable peptide linkers may include a plurality of amino acid residues, for example, 4, 5, 6, 7, 8, 9, 10, 15, 20 or 25 amino acids, such as (Gly)$_4$, (Gly)$_5$, (Gly)$_4$Ser, (Gly)$_4$(Ser)(Gly)$_4$, or combinations thereof or a multimer thereof (for example a dimer, a trimer, or a tetramer, or greater). For example, a suitable linker may be (GGGGS)$_3$. Alternative linkers include (Ala)$_3$(His)$_6$ or multimers thereof. Also included is a sequence which has at least 50%, 60%, 70%, 80%, 90%, 95% or 99% identity, using the default parameters of the BLAST computer program provided by HGMP, thereto.

In some cases the vector encodes a single VNAR-phage polypeptide fused to a coat protein. In these cases the vector is considered to be "monocistronic", expressing one transcript under the control of a certain promoter.

Illustrative examples of such vectors utilize the alkaline phosphatase (AP) or Tac promoter to drive expression of a monocistronic sequence encoding VNAR regions, with a linker peptide between the domains. The cistronic sequence can be connected at the 5'-end to an *E. coli* malE or heat-stable enterotoxin II (STII) signal sequence and at its 3'end to all or a portion of a viral coat protein (for example, the pill protein). The vector may further comprise a sequence encoding a dimerization domain (such as a leucine zipper) at its 3-end, between the second variable domain sequence and the viral coat protein sequence. Fusion polypeptides comprising the dimerization domain are capable of dimerizing to form a complex of two polypeptides.

In other cases, the VNAR sequences (multiple VNAR sequences or fragments) can be expressed as separate polypeptides, the vector thus being "bicistronic", allowing the expression of separate transcripts. In these vectors, a suitable promoter, such as the Ptac or PhoA promoter, can be used to drive expression of a bicistronic message. A first cistron, encoding, for example, a first VNAR sequence, can be connected at the 5'-end to a *E. coli* malE or heat-stable enterotoxin II (STII) signal sequence and at the 3'-end to a nucleic acid sequence encoding a gD tag. A second cistron, encoding, for example, a second VNAR sequence, can be connected at its 5'-end to a *E. coli* malE or heat-stable enterotoxin II (STII) signal sequence and at the 3'-end to all or a portion of a viral coat protein.

An example vector can comprise, a suitable promoter, such as Ptac or PhoA (AP) promoter which drives expression of first cistron encoding a VNAR sequence operably linked at 5'-end to an *E. coli* malE or heat stable enterotoxin II (STII) signal sequence and at the 3-end to a nucleic acid sequence encoding a gD tag. The second cistron encodes, for example, another VNAR sequence operatively linked at 5'-end to a *E. coli* malE or heat stable enterotoxin II (STII) signal sequence and at 3-end has a dimerization domain comprising IgG hinge sequence and a leucine zipper sequence followed by at least a portion of viral coat protein.

Fusion polypeptides of a VNAR sequence can be displayed on the surface of a cell, virus, or phagemid particle in a variety of formats. These formats include single chain fragment and multivalent forms of these fragments. The multivalent forms may be a dimer, or a higher multimer. The multivalent forms of display may be convenient because they have more than one antigen binding site which generally results in the identification of lower affinity clones and also allows for more efficient sorting of rare clones during the selection process.

Vectors constructed as described in accordance with the invention are introduced into a host cell for amplification and/or expression. Vectors can be introduced into host cells using standard transformation methods including electroporation, calcium phosphate precipitation and the like. If the vector is an infectious particle such as a virus, the vector itself provides for entry into the host cell. Transfection of host cells containing a replicable expression vector which encodes the gene fusion and production of phage particles according to standard procedures provides phage particles in which the fusion protein is displayed on the surface of the phage particle.

Replicable expression vectors are introduced into host cells using a variety of methods. In one embodiment, vectors can be introduced into cells using. Cells are grown in culture in standard culture broth, optionally for about 6-48 hours (or to OD600=0.6-0.8) at about 37° C., and then the broth is centrifuged and the supernatant removed (e.g. decanted). Initial purification is preferably by resuspending the cell pellet in a buffer solution (e.g. 1.0 mM HEPES pH 7.4) followed by recentrifugation and removal of supernatant. The resulting cell pellet is resuspended in dilute glycerol (e.g. 5-20% v/v) and again recentrifuged to form a cell pellet and the supernatant removed. The final cell concentration is obtained by resuspending the cell pellet in water or dilute glycerol to the desired concentration.

The use of higher DNA concentrations during electroporation (about 10x) increases the transformation efficiency and increases the amount of DNA transformed into the host cells. The use of high cell concentrations also increases the efficiency (about 10×). The larger amount of transferred DNA produces larger libraries having greater diversity and representing a greater number of unique members of a combinatorial library. Transformed cells are generally selected by growth on antibiotic containing medium.

Use of phage display for identifying target antigen binders, with its various permutations and variations in methodology, are well established in the art. One approach involves constructing a family of variant replicable vectors containing a transcription regulatory element operably linked to a gene fusion encoding a fusion polypeptide, transforming suitable host cells, culturing the transformed cells to form phage particles which display the fusion polypeptide on the surface of the phage particle, followed by a process that entails selection or sorting by contacting the recombinant phage particles with a target antigen so that at least a portion of the population of particles bind to the target with the objective to increase and enrich the subsets of the particles which bind from particles relative to particles that do not bind in the process of selection. The selected pool can be amplified by infecting host cells for another round of sorting on the same target with different or same stringency. The resulting pool of variants is then screened against the target antigens to identify novel high affinity binding proteins.

These novel high affinity binding proteins can be useful as therapeutic agents as antagonists or agonists, and/or as diagnostic and research reagents.

Fusion polypeptides such as antibody variable domains comprising the variant amino acids can be expressed on the surface of a phage, phagemid particle or a cell and then selected and/or screened for the ability of members of the group of fusion polypeptides to bind a target antigen which is typically an antigen of interest.

Such fusion proteins may be prepared by any suitable route, including by recombinant techniques by expression in host cell or cell-free systems, as well as by chemical synthetic routes.

Selection of Library Members

The processes of selection for binders to target can also be include sorting on a generic protein having affinity for antibody variable domains such as protein L or a tag specific antibody which binds to antibody or antibody fragments displayed on phage, which can be used to enrich for library members that display correctly folded antibody fragments (fusion polypeptides).

Target proteins, such as receptors, may be isolated from natural sources or prepared by recombinant methods by procedures known in the art. Target antigens can include a number of molecules of therapeutic interest.

Two main strategies of selection (sorting) for affinity which can be are (i) the solid-support method or plate sorting or immobilized target sorting; and (ii) the solution-binding method.

For the solid support method, the target protein may be attached to a suitable solid or semi-solid matrix which are known in the art such as agarose beads, acrylamide beads, glass beads, cellulose, various acrylic copolymers, hydroxyalkyl methacrylate gels, polyacrylic and polymethacrylic copolymers, nylon, neutral and ionic carriers, etc.

After attachment of the target antigen to the matrix, the immobilized target is contacted with the library expressing the fusion polypeptides under conditions suitable for binding of at least a subset of the phage particle population with the immobilized target antigen. Normally, the conditions, including pH, ionic strength, temperature and the like will mimic physiological conditions. Bound particles ("binders") to the immobilized target are separated from those particles that do not bind to the target by washing. Wash conditions can be adjusted to result in removal of all but the high affinity binders. Binders may be dissociated from the immobilized target by a variety of methods. These methods include competitive dissociation using the wild-type ligand (e.g. excess target antigen), altering pH and/or ionic strength, and methods known in the art. Selection of binders typically involves elution from an affinity matrix with a suitable elution material such as acid like 0.1 M HCl or ligand. Elution with increasing concentrations of ligand could elute displayed binding molecules of increasing affinity.

The binders can be isolated and then re-amplified in suitable host cells by infecting the cells with the viral particles that are binders (and helper phage if necessary, e.g. when viral particle is a phagemid particle) and the host cells are cultured under conditions suitable for amplification of the particles that display the desired fusion polypeptide. The phage particles are then collected and the selection process is repeated one or more times until binders of the target antigen are enriched in a way. Any number of rounds of selection or sorting can be utilized. One of the selection or sorting procedures can involve isolating binders that bind to a generic affinity protein such as protein L or an antibody to a polypeptide tag present in a displayed polypeptide such as antibody to the gD protein or polyhistidine tag.

Another selection method is the "solution-binding method" which allows solution phase sorting with an improved efficiency over the conventional solution sorting method. The solution binding method has been used for finding original binders from a random library or finding improved binders from a library that was designated to improve affinity of a particular binding clone or group of clones. The method comprises contacting a plurality of polypeptides, such as those displayed on phage or phagemid particles (library), with a target antigen labeled or fused with a tag molecule. The tag could be biotin or other moieties for which specific binders are available. The stringency of the solution phase can be varied by using decreasing concentrations of labeled target antigen in the first solution binding phase.

To further increase the stringency, the first solution binding phase can be followed by a second solution phase having high concentration of unlabeled target antigen after the initial binding with the labeled target in the first solution phase. Usually, 100 to 1000 fold of unlabeled target over labeled target is used in the second phase (if included). The length of time of incubation of the first solution phase can vary from a few minutes to one to two hours or longer to reach equilibrium. Using a shorter time for binding in this first phase may bias or select for binders that have fast on-rate. The length of time and temperature of incubation in second phase can be varied to increase the stringency. This provides for a selection bias for binders that have slow rate of coming off the target (off-rate).

After contacting the plurality of polypeptides (displayed on the phage/phagemid particles) with a target antigen, the phage or phagemid particles that are bound to labeled targets are separated from phage that do not bind. The particle-target mixture from solution phase of binding is isolated by contacting it with the labeled target moiety and allowing for its binding to, a molecule that binds the labeled target moiety for a short period of time (e.g. 2-5 min). The initial concentration of the labeled target antigen can range from about 0.1 nM to about 1000 nM. The bound particles are eluted and can be propagated for next round of sorting. Multiple rounds of sorting are preferred using a lower concentration of labeled target antigen with each round of sorting.

For example, an initial sort or selection using about 100 to 250 nM labeled target antigen should be sufficient to capture a wide range of affinities, although this factor can be determined empirically and/or to suit the desire of the practitioner. In the second round of selection, about 25 to 100 nM of labeled target antigen may be used. In the third round of selection, about 0.1 to 25 nM of labeled target antigen may be used. For example, to improve the affinity of a 100 nM binder, it may be desirable to start with nM and then progress to 5 and 1 nM labeled target, then, followed by even lower concentrations such as about 0.1 nM labeled target antigen.

As described herein, combinations of solid support and solution sorting methods can be advantageously used to isolate binders having desired characteristics. After selection/sorting on target antigen for a few rounds, screening of individual clones from the selected pool generally is performed to identify specific binders with the desired properties/characteristics. Preferably, the process of screening is carried out by automated systems to allow for high-throughput screening of library candidates.

Two major screening methods are described below. However, other methods may also be used. The first screening method comprises a phage ELISA assay with immobilized target antigen, which provides for identification of a specific binding clone from a non-binding clone. Specificity can be determined by simultaneous assay of the clone on target coated well and BSA or other non-target protein coated wells. This assay is automatable for high throughput screening.

One embodiment provides a method of selecting for an antibody variable domain that binds to a specific target antigen from a library of antibody variable domain by generating a library of replicable expression vectors comprising a plurality of polypeptides; contacting the library with a target antigen and at least one nontarget antigen under conditions suitable for binding; separating the polypeptide binders in the library from the nonbinders; identifying the binders that bind to the target antigen and do not bind to the nontarget antigen; eluting the binders from the target antigen; and amplifying the replicable expression vectors comprising the polypeptide binder that bind to a specific antigen.

The second screening assay is an invention embodied in this application which is an affinity screening assay that provides for screening for clones that have high affinity from clones that have low affinity in a high throughput manner. In the assay, each clone is assayed with and without first incubating with target antigen of certain concentration for a period of time (for e.g 30-60 min) before application to target coated wells briefly (e.g. 5-15 min). Then bound phage is measured by usual phage ELISA method, e.g. using anti-M13 HRP conjugates. The ratio of binding signal of the two wells, one well having been preincubated with target and the other well not preincubated with target antigen is an indication of affinity. The selection of the concentration of target for first incubation depends on the affinity range of interest. For example, if binders with affinity higher than 10 nM are desired, 1000 nM of target in the first incubation is often used. Once binders are found from a particular round of sorting (selection), these clones can be screened with affinity screening assay to identify binders with higher affinity.

Combinations of any of the sorting/selection methods described above may be combined with the screening methods. For example, in one embodiment, polypeptide binders are first selected for binding to immobilized target antigen. Polypeptide binders that bind to the immobilized target antigen can then be amplified and screened for binding to the target antigen and for lack of binding to nontarget antigens. Polypeptide binders that bind specifically to the target antigen are amplified. These polypeptide binders can then selected for higher affinity by contact with a concentration of a labeled target antigen to form a complex, wherein the concentration ranges of labeled target antigen from about 0.1 nM to about 1000 nM, the complexes are isolated by contact with an agent that binds to the label on the target antigen. The polypeptide binders are then eluted from the labeled target antigen and optionally, the rounds of selection are repeated, each time a lower concentration of labeled target antigen is used. The high affinity polypeptide binders isolated using this selection method can then be screened for high affinity using for example, a solution phase ELISA assay or a spot competition ELISA assay.

After binders are identified by binding to the target antigen, the nucleic acid can be extracted. Extracted DNA can then be used directly to transform *E. coli* host cells or alternatively, the encoding sequences can be amplified, for example using PCR with suitable primers, and sequenced by typical sequencing method. Variable domain DNA of the binders can be restriction enzyme digested and then inserted into a vector for protein expression.

In some embodiments, libraries comprising polypeptides of the invention are subjected to a plurality of sorting rounds, wherein each sorting round comprises contacting the binders obtained from the previous round with a target antigen distinct from the target antigen(s) of the previous round(s).

In another aspect of the invention provides methods for selecting for high affinity binders to specific target antigens such as growth hormone, bovine growth hormone, insulin like growth factors, human growth hormone including n-methionyl human growth hormone, parathyroid hormone, thyroxine, insulin, proinsulin, amylin, relaxin, prorelaxin, glycoprotein hormones such as follicle stimulating hormone (FSH), leutinizing hormone (LH), hemapoietic growth factor, fibroblast growth factor, prolactin, placenta lactogen, tumor necrosis factors, mullerian inhibiting substance, mouse gonadotropin-associated polypeptide, inhibin, activin, vascular endothelial growth factors, integrin, nerve growth factors such as NGF-beta, insulin-like growth factor-I and II, erythropoietin, osteoinductive factors, interferons, colony stimulating factors, interleukins, bone morphogenetic proteins, LIF, SCF, FLT-3 ligand and kit-ligand.

The methods of the invention provide for libraries of polypeptides (e.g. antigen specific antigen binding molecules) with one or more diversified CDR regions. These libraries are sorted (selected) and/or screened to identify high affinity binders to a target antigen. In one aspect, polypeptide binders from the library are selected for binding to target antigens, and for affinity. The polypeptide binders selected using one or more of these selection strategies, then, may be screened for affinity and/or for specificity (binding only to target antigen and not to non-target antigens).

A method comprises generating a plurality of polypeptides with one or more diversified CDR regions, sorting the plurality of polypeptides for binders to a target antigen by contacting the plurality of polypeptides with a target antigen under conditions suitable for binding; separating the binders to the target antigen from those that do not bind; isolating the binders; and identifying the high affinity binders. The affinity of the binders that bind to the target antigen can be determined using competition ELISA such as described herein. Optionally, the polypeptides can be fused to a polypeptide tag such as gD, poly his or FLAG which can be used to sort binders in combination with sorting for the target antigen.

Another embodiment provides a method of selecting for an antigen specific antigen binding molecule that binds to a target antigen from a library of VNARs comprising: a) generating a library of replicable expression vectors comprising a plurality of polypeptides of the invention; b) isolating polypeptide binders to a target antigen from the library by contacting the library with an immobilized target antigen under conditions suitable for binding; c) separating the polypeptide binders in the library from the nonbinders and eluting the binders from the target antigen; d) amplifying the replicable expression vectors having the polypeptide binders; and e) optionally, repeating steps a-d at least twice.

The method may further comprise: f) incubating the amplified replicable expression vectors comprising polypeptide binders with a concentration of labeled target antigen in the range of 0.1 nM to 1000 nM under conditions suitable for binding to form a mixture; g) contacting the mixture with an immobilized agent that binds to the label on the target antigen; h) separating the polypeptide binders bound to labeled target antigen and eluting the polypeptide binders from the labeled target antigen; i) amplifying replicable expression vectors comprising the polypeptide binders; and j) optionally, repeating steps f) to i) at least twice, using a lower concentration of labeled target antigen each time. Optionally, the method may comprise adding an excess of unlabeled target antigen to the mixture and incubating for a period of time sufficient to elute low affinity binders from the labeled target antigen.

Another embodiment provides a method of isolating or selecting for high affinity binders to a target antigen from a library of replicable expression vectors comprising: a) generating a library of replicable expression vectors comprising a plurality of polypeptides of the invention; b) contacting the library with a target antigen in a concentration of at least about 0.1 nM to 1000 nM to isolate polypeptide binders to the target antigen; c) separating the polypeptide binders from the target antigen and amplifying the replicable expression vector comprising the polypeptide binders; d) optionally, repeating steps a-c at least twice, each time with a lower concentration of target antigen to isolate polypeptide binders that bind to lowest concentration of target antigen; e) selecting the polypeptide binder that binds to the lowest concentration of the target antigen for high affinity by incubating the polypeptide binders with several different dilutions of the target antigen and determining the IC50 of the polypeptide binder; and f) identifying a polypeptide binder that has an affinity for the target antigen of about 0.1 nM to 200 nM.

Another embodiment provides an assay for selecting polypeptide binders from a library of replicable expression vectors comprising a plurality of polypeptides of the invention comprising: a) contacting the library with a concentration of labeled target antigen in a concentration range of 0.1 nM to 1000 nM, under conditions suitable for binding to form a complex of a polypeptide binders and the labeled target antigen; b) isolating the complexes and separating the polypeptide binders from the labeled target antigen; c) amplifying the replicable expression vector comprising the polypeptide binders; d) optionally, repeating steps a-c at least twice, each time using a lower concentration of target antigen.

Optionally, the method may further comprise adding an excess of unlabeled target antigen to the complex of the polypeptide binder and target antigen. In a preferred embodiment, the steps of the method are repeated twice and the concentrations of target in the first round of selection is about 100 nM to 250 nM, and in the second round of selection is about 25 nM to 100 nM, and in the third round of selection is about 0.1 nM to 25 nM.

The invention also includes a method of screening a library of replicable expression vectors comprising a plurality of polypeptides of the invention comprising: a) incubating first a sample of the library with a concentration of a target antigen under conditions suitable for binding of the polypeptides to the target antigen; b) incubating a second sample of the library without a target antigen; c) contacting each of the first and second sample with immobilized target antigen under conditions suitable for binding of the polypeptide to the immobilized target antigen; d) detecting the amount of the bound polypeptides to immobilized target antigen for each sample; e) determining the affinity of the polypeptide for the target antigen by calculating the ratio of the amounts of bound polypeptide from the first sample over the amount of bound polypeptide from the second sample.

The libraries generated as described herein may also be screened for binding to a specific target and for lack of binding to nontarget antigens. In one aspect, another embodiment provides a method of screening for an antibody variable domain that binds to a specific target antigen from a library of VNARs comprising: a) generating a library of replicable expression vectors comprising a plurality of polypeptides of the invention; b) contacting the library with a target antigen and at least one nontarget antigen under conditions suitable for binding; c) separating the polypeptide binders in the library from the nonbinders; d) identifying the binders that bind to the target antigen and do not bind to the nontarget antigen; e) eluting the binders from the target antigen; and f) amplifying the replicable expression vectors comprising the polypeptide binder that bind to a specific antigen.

Combinations of any of the sorting/selection methods described above may be combined with the screening methods. For example, in one embodiment, polypeptide binders are first selected for binding to immobilized target antigen. Polypeptide binders that bind to the immobilized target antigen can then be amplified and screened for binding to the target antigen and for lack of binding to nontarget antigens. Polypeptide binders that bind specifically to the target antigen are amplified. These polypeptide binders can then selected for higher affinity by contact with a concentration of a labeled target antigen to form a complex, wherein the concentration range of labeled target antigen is from about 0.1 nM to about 1000 nM, the complexes are isolated by contact with an agent that binds to the label on the target antigen. The polypeptide binders are then eluted from the labeled target antigen and optionally, the rounds of selection are repeated, each time a lower concentration of labeled target antigen is used. The high affinity polypeptide binders isolated using this selection method can then be screened for high affinity using for example, a solution phase ELISA assay or a spot competition ELISA assay.

Isolation of VNARs

VNAR domains may be obtained from phage-displayed libraries constructed using tissues from target-immunized sharks (Dooley, H., et al. *Mol Immunol,* 2003. 40(1): p. 25-33; Nuttall, S. D., et al, Proteins, 2004. 55(1): p. 187-97; and Dooley, H., et al., *Proc Natl Acad Sci USA,* 2006. 103(6): p. 1846-51), WO2003/014161, incorporated by reference describes a useful method for immunizing a shark and obtaining binding domains.

VNAR binding domains may also be obtained from synthetic libraries comprising VNAR sequences. WO2014/173959, incorporated by reference, describes a useful method for developing VNAR libraries and obtaining binding domains.

Additionally it has been shown that libraries with synthetic diversity targeted to CDR3 can be used to obtain binding domains based on VNAR structures (Nuttall, S. D., et al. *Mol Immunol,* 2001. 38(4): p. 313-26; Nuttall, S. D., et al. *Eur J Biochem,* 2003. 270(17): p. 3543-54; Shao, C. Y., et al. Mol Immunol, 2007. 44(4): p. 656-65 and Liu, J. L., et al. *BMC Biotechnol,* 2007. 7: p. 78; WO2005/118629.

VNARS of the invention may be further adapted to reduce potential immunogenicity when administered to man (humanization) as described herein.

The present invention also provides an isolated nucleic acid comprising a polynucleotide sequence that encodes a binding molecule according to any aspect or embodiment described herein. Furthermore, there is provided herein a method for preparing a binding molecule according to the invention, comprising cultivating- or maintaining a host cell comprising the polynucleotide under conditions such that said host cell produces the binding molecule, optionally further comprising isolating the binding molecule.

Pharmaceutical Compositions and Uses

According to the invention, there is provided a pharmaceutical composition comprising a multi-domain specific binding molecule of the invention. Such compositions include fusion proteins comprising said antigen specific antigen binding molecules.

The pharmaceutical composition may also comprise an antigen specific antigen binding molecule of the present invention fused to a therapeutic protein, or a fragment thereof. The therapeutic protein may be a hormone, a growth factor (e.g. TGFβ, epidermal growth factor (EGF), platelet derived growth factor (PDGF), nerve growth factor (NGF), colony stimulating factor (CSF), hepatocyte growth factor, insulin-like growth factor, placenta growth factor); a differentiation factor; a blood clotting factor (for example, Factor VIIa, Factor VIII, Factor IX, VonWillebrand Factor or Protein C) or another protein from the blood coagulation cascade (for example, antithrombin); a cytokine e.g. an interleukin, (e.g. IL1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32 or IL-33 or an interferon (e.g. IFN-α, IFN-β and IFN-γ), tumour necrosis factor (TNF), IFN-γ inducing factor (IGIF), a bone morphogenetic protein (BMP, e.g. BMP-1, BMP-2, BMP-3, BMP-4, BMP-4, BMP-5, BMP-6, BMP-7, BMP-8, BMP-9, BMP10, BMP-11, BMP-12, BMP-13); an interleukin receptor antagonist (e.g. IL-1ra, IL-1RII); a chemokine (e.g. MIPs (Macrophage Inflammatory Proteins) e.g. MIP1α and MIP1β; MCPs (Monocyte Chemotactic Proteins) e.g. MCP1, 2 or 3; RANTES (regulated upon activation normal T-cell expressed and secreted)); a trophic factor; a cytokine inhibitor; a cytokine receptor; an enzyme, for example a free-radical scavenging enzyme e.g. superoxide dismutase or catalase or a pro-drug converting enzyme (e.g. angiotensin converting enzyme, deaminases, dehydrogenases, reductases, kinases and phosphatases); a peptide mimetic; a protease inhibitor; a tissue inhibitor of metalloproteinases (TIMPs e.g. TIMP1, TIMP2, TIMP3 or TIMP4) or a serpin (inhibitors of serine proteases).

In other embodiments of the invention, the therapeutic protein in the fusion protein may be an antibody, or a engineered fragment thereof, including Fab, Fc, F(ab')$_2$ (including chemically linked F(ab')$_2$ chains), Fab', scFv (including multimer forms thereof, i.e. di-scFv, or tri-scFv), sdAb, or BiTE (bi-specific T-cell engager). Antibody fragments also include variable domains and fragments thereof, as well as other VNAR type fragments (IgNAR molecules).

The pharmaceutical composition may be composed of a number of antigen specific antigen binding molecules of the invention, for example dimers, trimers, or higher order multimers, i.e. 2, 3, 4, 5, 6, 7, or 8-mers, fused to the therapeutic protein.

The fusion of the antigen specific antigen binding molecules of the invention to the therapeutic protein may at any convenient site on the protein and may be N-, C- and/or N-/C-terminal fusion(s). In one embodiment of the invention, the fusion of the antigen specific antigen binding molecules of the invention is to both the N- and C-terminals of a therapeutic protein.

Pharmaceutical compositions of the invention may comprise any suitable and pharmaceutically acceptable carrier, diluent, adjuvant or buffer solution. The composition may comprise a further pharmaceutically active agent. Such carriers may include, but are not limited to, saline, buffered saline, dextrose, liposomes, water, glycerol, ethanol and combinations thereof.

Such compositions may comprise a further pharmaceutically active agent as indicated. The additional agents may be therapeutic compounds, e.g. anti-inflammatory drugs, cytotoxic agents, cytostatic agents or antibiotics. Such additional agents may be present in a form suitable for administration to patient in need thereof and such administration may be simultaneous, separate or sequential. The components may be prepared in the form of a kit which may comprise instructions as appropriate.

The pharmaceutical compositions may be administered in any effective, convenient manner effective for treating a patient's disease including, for instance, administration by oral, topical, intravenous, intramuscular, intranasal, or intradermal routes among others. In therapy or as a prophylactic, the active agent may be administered to an individual as an injectable composition, for example as a sterile aqueous dispersion, preferably isotonic.

For administration to mammals, and particularly humans, it is expected that the daily dosage of the active agent will be from 0.01 mg/kg body weight, typically around 1 mg/kg, 2 mg/kg or up to 4 mg/kg. The physician in any event will determine the actual dosage which will be most suitable for an individual which will be dependent on factors including the age, weight, sex and response of the individual. The above dosages are exemplary of the average case. There can, of course, be instances where higher or lower dosages are merited, and such are within the scope of this invention.

According to the invention, there is provided an antigen specific antigen binding molecule or multi-domain specific binding molecule of the invention for use in medicine. This aspect of the invention therefore extends to the use of such of an antigen specific antigen binding molecule or multi-domain specific binding molecule of the invention in the manufacture of a medicament for the treatment of a disease in a patient in need thereof. An antigen specific antigen binding molecule of the invention can also be used to prepare a fusion protein comprising such a specific binding molecule as defined above in relation to pharmaceutical compositions of the invention.

Such uses also embrace methods of treatment of diseases in patients in need of treatment comprising administration to the patient of a therapeutically effective dosage of a pharmaceutical composition as defined herein comprising an antigen specific antigen binding molecule or multi-domain specific binding molecule of the invention.

As used herein, the term "treatment" includes any regime that can benefit a human or a non-human animal. The treatment of "non-human animals" in veterinary medicine extends to the treatment of domestic animals, including horses and companion animals (e.g. cats and dogs) and farm/agricultural animals including members of the ovine, caprine, porcine, bovine and equine families. The treatment may be a therapeutic treatment in respect of any existing condition or disorder, or may be prophylactic (preventive treatment). The treatment may be of an inherited or an acquired disease. The treatment may be of an acute or chronic condition. The treatment may be of a condition/disorder associated with inflammation and/or cancer. The antigen specific antigen binding molecules or multi-domain specific binding molecules of the invention may be used in the treatment of a disorder, including, but not limited to osteoarthritis, scleroderma, renal disease, rheumatoid arthritis, inflammatory bowel disease, multiple sclerosis, atherosclerosis, or any inflammatory disease.

The antigen specific antigen binding molecules or multi-domain specific binding molecules of the present invention may also be used to investigate the nature of a disease condition in a patient. The antigen specific antigen binding molecules or multi-domain specific binding molecules may be used to prepare images of sites of disease in the body of a subject using imaging techniques such as X-ray, gamma-ray, or PET scanning, or similar. The invention may therefore extend to a method of imaging a site of disease in a subject, comprising administration of a suitably detectably labeled antigen specific antigen binding molecule or multi-domain specific binding molecules to a subject and scanning the subject's body subsequently. Alternatively, administration of said molecules to a subject may provide for a test result by analysing a sample from the subject following administration of the molecule. Such embodiments may include a method of diagnosis of a disease or medical condition in a subject comprising administration of an antigen specific antigen binding molecule or multi-domain specific binding molecule of the invention. The multi-domain specific binding molecules of the invention may be especially useful with regard to diagnostic sensitivity, in particular when multiple VNARs that target different epitopes on the same antigen are used.

In a further aspect the present invention provides a method for treating a condition mediated by TNFα, the method comprising the administration of a therapeutically effective amount of a composition of the invention that specifically binds to TNFα.

Measurement of Binding

Detection and measurement of binding of a VNAR to a target can be measured in a number of ways well known in the art including ELISA and surface plasmon resonance.

Functional Activity

VNARs of the invention may function in a number of ways including binding to and neutralizing the biological effects of a molecule such as a cytokine, binding to a receptor preventing ligand binding or causing a biological effect post-binding.

Methods of Measuring the Functional Activity of a Binding Domain are Known in the Art.

Preferred features for the second and subsequent aspects of the invention are as for the first aspect of the invention mutatis mutandis.

The present invention will now be described by way of reference to the following Examples and accompanying Drawings which are present for the purposes of illustration only and are not to be construed as being limiting on the invention.

Example 1—FastTrack Humanisation: Modifying DPK9 Homology Frameworks onto soloMER Domains to Restore Function in an Anti-TNFα soloMER Throughout this example a humanised VNAR sequence can also be referred to as a soloMER. The first step to humanisation involved incorporating sufficient but not detrimental human residues into the lead anti-TNF VNAR domains (D1 and C4) using a human antibody sequence DPK9 homology model (see FIG. 1).

For the creation of a humanised Quad X binder (see FIG. 2) D1-V2 and C4-V1 were maintained except where stated, framework 1 or framework 4 was restored to the naïve VNAR sequence, thereby creating the nomenclature soloMER Quad-X VNAR FW1 restored or soloMER Quad-X VNAR FW4 restored. Polyethylenimine-mediated transfection and transient expression in HEK293 host cells was performed using serum-free FreeStyle™ 293 media (Invitrogen). Transient protein expression was continued for 5-7 days before media supernatant was harvested. Protein-A affinity chromatography was adopted for the Fc fused soloMER purification. Expression levels of up to 150 mg/l (Fc-based soloMER constructs) was achieved in these mammalian systems.

soloMER Quad-X VNAR FW1 did not show expression in HEK293 cells, however soloMER Quad-X VNAR FW4 showed significant protein expression (see FIG. 3). Therefore, this format was taken forward for further characterisation and functional assessment in comparison with the native VNAR Quad-X (also referred to as WT Quad-X).

In this head-to-head target binding comparison, both the soloMER Quad-X (VNAR FW4) and native Quad-X showed comparable functionality recognising TNFα (FIG. 4A) and not recognising Human Serum Albumin (FIG. 4B). This is also demonstrated by their binding kinetics and affinity to human TNF-alpha (see Table 3).

The IBIS MX96 SPRi (Surface Plasmon Resonance imaging) instrument was utilised for the determination of binding kinetics of the soloMER and native VNAR Quad-X protein samples. Anti-TNF domains were amine coupled to the sensor (array chip) using the Continuous Flow Microspotter (CFM), before passing the antigen (human TNF-alpha) over the immobilised soloMER or native VNAR Quad-X.

TABLE 3

IBIS MX96 SPRi Binding kinetics sensograms and affinity data of soloMER Quad-X interaction with human TNF-alpha

|  | ka | kd | KD |
| --- | --- | --- | --- |
| WT D1-Fc-C4 Quad-X | 3.20E+04 | 8.95E−06 | 2.80E−10 |
| SoloMER D1-Fc-C4 (VNAR FW4) Quad-X | 6.09E+04 | 4.92E−05 | 8.09E−10 |

The SEC data in FIG. 5 confirms monomericity and similarity of the domains biochemical behaviour with no evidence of aggregation or instability.

In the above in vitro human TNF-alpha neutralisation assay (see FIG. 6), it was demonstrated that both the native WT Quad-X (D1-Fc-C4 VNAR) and the soloMER Quad-X (also known as the soloMER Quad-X VNAR FW4) showed an identical capacity to neutralise the cytotoxic effect of human TNF-alpha on mouse fibrosarcoma cell line (L929 cells). The achieved $ND_{50}$ values for the native and soloMER Quad-X VNAR FW4 are 0.002 nM and 0.0017 nM, respectively.

Example 2—Clone P3A1 Recognises the Human Protein Called ROR1. Humanisation of Clone P3A1 was Performed in a Similar Way to Anti-TNF VNAR Clones (See FIG. 1)

Several humanised variants (V1 to V6) of P3A1 were designed, (FIG. 7) synthesised as dimers (2×P3A1 variants joined with a short peptide linker and containing a HisMyc detection tag), sequences confirmed as correct and cloned into a suitable bacterial expression vector. Of these variants V1 and V4 were the only ones to produce any protein (Table 4). P3A1 V1 showed functional binding which was better (higher affinity) than the parental WT clone P3A1 (Table 4). V4 expression levels were poor and precipitated during purification. V1 also retained good specificity for its hROR1 target protein as it was unable to bind to the closely related hROR2 protein mimicking the specificity of the WT non-humanised P3A1 clone (Table 4).

TABLE 4

| Construct | Expression | Yield (mg/L) | Binding to hROR2 | Binding to hROR1 (affinity determined by BIAcore) |
|---|---|---|---|---|
| P3A1 WT dimer HisMyc | | 1.5 | None | 302 pM |
| P3A1 V1 dimer HisMyc | Good | 1 | None | 179 pM |
| P3A1 V4 dimer HisMyc | Poor | 0.1 | — | — |

Example 3-5 Variants of Humanised VNARs with Varying Levels of Humanisation

VNAR clones E4 and 78 recognise the human protein DLL4. As described for the anti-TNF programme and anti-ROR1 (clone P3A1) programs, anti-DLL4 VNAR domains E4 and 78 were humanised using DPK9 as human Ig homology template, resulting in 5 variants of humanised VNARs with varying degrees of DPK9 residues (levels of humanisation).

The alignment shown in FIG. 8 illustrates the human residues from the human germline Vk1 sequence, DPK9 applied in the humanisation and the extent of increasing percentage of human residue grafting from soloMER-V1 to V5.

The humanised VNAR E4 and 78 variants (soloMERs) were assessed for expression in a pilot small scale non-optimised system (E. coli).

Soluble VNAR protein was expressed in prokaryotic (E. coli). Expression in E. coli TG1 cells was induced with 1 mM isopropyl β-D-1-thiogalactopyranoside (IPTG), and soluble VNAR protein was extracted from the periplasm (E. coli TG1 cells). All VNAR constructs were expressed as cytoplasmic protein in IPTG-induced E. coli TG1 cells using pIMS100 expression vector. Extraction of cytoplasmic VNAR protein was achieved using the BugBuster™ protein extraction reagent plus Benzonase© (Novagen).

All VNAR constructs were purified via poly-histidine tag using immobilized metal affinity chromatography. Electrophoresis of purified protein samples was performed on NuPAGE 4-12% Bis-Tris gels using a MES buffer system (Invitrogen) in accordance with the manufacturer's instructions. Protein samples were reduced and denatured using NuPAGE LDS+β-mercaptoethanol, and boiled for 3-5 min at 100° C.

Assessing Binding Activity of soloMER Domains Using Direct Binding ELISA Technique Ninety-six well flat bottom Maxisorp Nunc Immuo plates (Thermo Scientific) were coated with 1 μg/mL hDLL4 overnight at 4° C. The plates were washed three times with 200 μl/well PBST [PBS with 0.1% (v/v) Tween 20] before blocking with 200 μl of 4% milk (w/v) PBS (MPBS) per well and incubated at 37° C. for 1 h. The blocked plates were washed three times with PBST prior to the addition of unquantified soloMER/VNAR protein solution which was then diluted 1:2 in PBS down the plate and incubated at room temperature for 1 h. Plates were washed three times with PBST and 100 μl of 1 in 1,000 dilution of anti-poly-histidine-HRP (histidine tagged proteins) was added to the plates and incubated for 1 h at room temperature. The plates were washed and developed by adding 100 μl tetramethyl-benzidine (TMB) substrate solution and neutralized using 50 μl 1 M $H_2SO_4$.

The best variants identified from these initial functional characterisations of the soloMER E4 and 78 variants were E4-V2 and 78-V2 and 78-V4 although each of the frameworks showed some level of functional binding and particularly for the 78 clone variants (FIG. 10).

E4-V2 and 78-V2 Humanised Libraries for Affinity Maturation

An anti-DLL4 soloMER libraries was designed based on the E4-V2 frameworks with the introduction of tailored diversity within CDR1, HV2 and HV4 regions as shown in FIG. 11. A database of VNAR sequences from Squalus acanthus was analysed to determine the levels of predicted diversity that could be accommodated within the desired regions.

Following the cloning of the library 96 sequences from each library (E4 and 78 parental sequences) were analysed and both libraries displayed greater than 90% correctness that is full sequences and different sequences from each other. The total library sizes (unique clones) were estimated to be approximately $1 \times 10^9$ clones.

Monoclonal Phage Binding ELISA to DLL4 from Humanised Libraries.

Phage outputs were screened for binding to human DLL4 by monoclonal phage ELISA. The unpanned libraries were screened along with rounds 1-3 following biopanning following the strategy outlined in FIG. 12. A number of binders were identified from the E4-V2 library (unpanned and panned) with improved binding when compared to the E4-V2 parental framework, binding affinity approaching that of the pre-humanised parental clone E4 WT and retained specificity for the target antigen human DLL4. (FIG. 13) with no binding to human serum albumin (HSA). The sequences of these clones are reported in FIG. 14.

Example 4—Generation of the D3V2 soloMER Library

Library Design

Clone D3 recognises the human protein ROR1. Several humanised variants of D3 were synthesised, sequences confirmed as correct (FIG. 15) and cloned into a suitable expression vector. Of these variants D3V2 was chosen for further optimisation based on the data in Table 5.

TABLE 5

| Name | Tm (° C.) | | BLI against hROR1 | | |
|---|---|---|---|---|---|
| | Boltzmann | Derivative | ka (1/Ms) | kdis (1/s) | KD (nM) |
| D3 WT | 63.6 | 64.4 | 1.21E+06 | 9.43−E05 | 15.5 |
| D3 V1 | 52.26 | 53.25 | 1.50E+06 | 1.58−E04 | 16.1 |
| D3 V2 | 55.32 | 56.50 | 1.85E+06 | 1.63−E04 | 18.9 |
| D3 V4 | 52.7 | 54.1 | 1.38E+06 | 5.45−E04 | 58.5 |
| D3 V5 | — | — | 1.93E+05 | 5.42−E05 | 36.2 |

V1 and V2 show little change in KD affinity compared to WT D3. V2 showed an improved Tm over V1 and so the D3 V2 derivative was chosen for the production of and selection from a D3V2 humanised library designed to improve binding affinity of humanised D3V2 variant (soloMER) via randomisation of CDR1, HV2 and HV4 regions without any changes within the V2 frameworks. The choice of amino acid changes and possibilities in the hypervariable regions (CDR1, HV2 and HV4) was made designed on the data analysis of VNAR sequences from Squalus acanthus. Sequence of D3V2 and library design are shown in FIG. 16.

The library was synthesised by controlled mutagenesis of CDR1, HV2 and HV4. Residues 26-33, 44-52 and 61-65 located within CDR1, HV2 and HV4 loops respectively were changed to selected amino acids as specified in FIG. 16 resulting in total library diversity of $8.2 \times 10^6$ combinations.

Libraries Construction

D3V2 SoloMER library DNA was amplified by PCR using specific primers to introduce NcoI and NotI restriction sites for cloning into pHEN phagemid vector. Library DNA ligated into the vector was transformed into electrocompetent TG1 *E. coli* (Lucigen). The library size was calculated to be $1.5 \times 10^7$ unique clones (by sequence and full length insert).

Screening of SoloMER Library for Antigen Specific VNAR Sequences

Recombinant human ROR1 protein was used for selections and screening of the D3V2 soloMER library. To isolate ROR1 specific soloMERs biotinylated antigen was pre-decorated on streptavidin-coated beads and 3 rounds of panning (see FIG. 17 for details of selection strategy) with low stringency were carried out. Antigen specific phage was detected by ELISA of phage monoclonals and the percentage of antigen specific phage enriched from PAN1 (11%) to PAN 3 (88%).

D3V2 soloMER library outputs of PAN3 were sub-cloned into pIMS147-c kappa vector for soluble soloMER expression. Library DNA was ligated into pIMS147-c kappa via NotI/NcoI restriction sites and transformed into electrocompetent TG1 *E. coli* (Lucigen). The library size was calculated to be $3.8 \times 10^8$.

Single clones were cultured and induced for periplasmic soluble protein expression and resulted in 83% positive binders to huROR1.

Positive binders to huROR1 in monoclonal phage ELISA and periplamic-prep ELISA (detected via the ck domain) were aligned and 9 unique sequences identified.

TABLE 6

| Sample ID | Yield (mg) for 1 L expression | pI | % hydrophobicity | KD (M) | ka (1/Ms) | kdis (1/s) |
|---|---|---|---|---|---|---|
| F11 | 4.43 | 7.28 | 32.02 | 1.11E−08 | 1.16E+05 | 1.29E−03 |
| E08 | 8.94 | 8.31 | 31.14 | 6.87E−09 | 2.08E+05 | 1.43E−03 |
| F01 | 17.1 | 8.3 | 31.14 | 2.13E−08 | 7.85E+04 | 1.67E−03 |
| G02 | 8.02 | 6.83 | 31.58 | 1.75E−08 | 1.06E+05 | 1.86E−03 |
| D3 WT | 2.13 | 7.25 | 31.16 | 6.08E−09 | 2.54E+06 | 1.54E−02 |
| D3 v.2 | 1 | 6.72 | 31.88 | 1.56E−08 | 1.52E+06 | 2.38E−02 |

Following further analysis, 4 hits were taken forward based on their expressibility and binding to the antigen. Clones F11, E08, F01 and G02 (Table 6) all showed improved levels of expression over both the humanised D3 V2 variant and the parental clone D3 WT. Furthermore, all clones showed at least equivalent affinity for the hROR1 antigen as the D3 V2 clone with no binding to the closely related hROR2 protein (results not shown). Clone E08 showed an increase in affinity over the D3 V2 clone and was equivalent in affinity to the parental D3 WT clone. The results show that the library selections were very successful in generating a humanised variant of D3 WT with equivalent affinity and specificity but improved bio-processing characteristics (clone E08). The humanised sequences of the four best binding clones are in FIG. 18.

Library Synthesis

CDR loops libraries and individual clones were synthetized by GeneArt Gene Synthesis according to the design outlined in Figures with provided design.

Library Subcloning into pHEN

PCR amplification of synthetised library was performed using Phusion High-Fidelity PCR Master Mix and the following primers: D3_FOR_Ncol AGCCGGCCATG-GCCGCTTC (SEQ ID NO: 41); D3_REV_NotI ATGTGCGGCCGCCCCTGAGGCCTG (SEQ ID NO: 42).

Amplicons were purified with Promega PCR purification Kit, digested with NcoI and NotI and ligated into pHEN vector opened with the same restriction enzyme. Ligation performed at ratio 1:1.

Library Selection

1. To rescue library phage for selections, cultures from library glycerol stocks were grown at 37° C. and 250 rpm, in 2xTY, 1% (w/v) glucose, 100 μg/ml ampicillin to an OD600 of 0.5.

2. Cells were super-infected with ~1×10⁹ M13K07 helper phage (NEB) and then incubated overnight in 2×TY, 100 μg/ml ampicillin, 50 μg/ml kanamycin at 25° C. and 250 rpm.
3. The phage was PEG-precipitated (20% PEG/2.5 M NaCl) twice from the bacterial culture and the resulting phage pellets were resuspended in 1 ml PBS.
4. Two hundred microliters of Dynabeads M-280 Streptavidin (Invitrogen #11205D), pre-blocked with 3% (w/v) MPBS, were coated biotinylated human ROR1 rotating at 20 rpm, at room temperature for 1 h.
5. Library phage was de-selected by incubation with Dynabeads for 1 h rotating at room temperature and then added to the antigen-coated beads.
6. Beads were washed 3 times with PBST and 3 times with PBS, eluted by rotating for 8 min in 400 μl 100 mM TEA and neutralised by the addition of 200 μl 1 M Tris-HCl pH 7.5.
7. E. coli TG1 cells (10 ml) were infected with 300 μl of eluted phage for 30 min at 37° C. and grown overnight at 37° C. on TYE agar plates containing 1% (w/v) glucose and 100 μg/ml ampicillin.
8. Three further rounds of selection were conducted and outputs were screened for antigen-specific binding by monoclonal phage and periplasmic extract ELISAs against a range of different antigens depending on the library design (including but not limited to human DLL4 (hDLL4), Human Serum Albumin (HSA), human ROR1 (hROR1) and human ROR2 (hROR2)). Phage binders were detected using HRP-conjugated anti-M13 antibody and periplasmic protein was detected using HRP-conjugated anti-poly histidine, c-myc or human C kappa-antibody.

Screening soloMER Libraries: Periplasmic Expression of Single Clones in 96 Well Format and Binding ELISA 1. Inoculate Greiner 96 deep-well plate containing 1 ml 2×TY/0.1% (w/v) glucose/100 μg/μl Amp. Grow for 5 h at 37° C., 180 rpm in incubation chamber until faintly turbid.
2. Induced with 110 μl/well 1 mM IPTG in 2×TY/Amp (final concentration of IPTG=100 M); same shaking speed at 28° C. overnight.
3. Spin cultures for 15 min at 4° C. and 3500 rpm. Decant supernatant and tap dry on paper towels.
4. Add 250 μl/well ice-cold TES buffer (50 mM Tris/HCl, pH8.0/1 mM EDTA, pH8.0/20% (w/v) Sucrose) to the pellets. Vortex.
5. Add 250 μl 1:5 diluted in water TES buffer (ice-cold). Keep on ice (or in the ridge) for 30 min. Spin as above. Keep supernatants on ice until ready to use.

ELISA
1. Coat 96 well plates with 1 μg/ml of hROR1-Fc, hROR2-Fc or HSA or hDLL4 and incubated overnight at 4° C.
2. Wash plates 3×PBST.
3. Block coated plates with 200 μl/well 4% M-PBS. Incubate for 1 h at room temperature.
4. Wash 3×PBST.
5. Incubate plates with 100 μl/well of peri-prep for 1 h at room temperature.
6. Add 100 μl of anti-His-HRP or human C kappa-HRP (1:1000 in PBST) and incubate 1 h at room temperature.
7. Wash 2×PBST and 2×PBS.
8. Add 100 μl/well of TMB substrate. Stop reaction with 50 μl/well 1M H₂SO₄.

Large Scale Expression and Purification of ROR1 VNAR Binders

1. Inoculate clones from glycerol stock into 20 ml of 2×TY/1% (w/v) glucose/100 μg/μl Amp. Grow overnight at 37° C. shaking at 250 rpm in incubation chamber.
2. Dilute the overnight culture 1:50 in TB+phosphate salt+1% (w/v) glucose+100 μg/ml Amp media (10 ml o/n culture into 500 ml media; 450 ml TB+50 ml phosphate salt) and incubate at 37° C. with vigorous shaking (250 rpm) all day or as long as possible.
3. Pellet the cells by centrifugation at 4,000×g for 20 min at 20° C.
4. Re-suspend the cells in the same volume of TB+phosphate salt+1% (w/v) glucose+100 μg/ml Amp media and incubate at 30° C. overnight with shaking (250 rpm).
5. Pellet the cells by centrifugation at 4,000×g for 20 min at 20° C. and re-suspend the cells in the same volume of TB+phosphate salt+100 gg/ml Amp media (NO GLUCOSE). Add IPTG to a final conc. of 1 mM IPTG. Incubate at 30° C. for 4-5 h with shaking (250 rpm).
6. Collect the cells by centrifugation at 4500×g for 30 min [the pellet could be frozen at this point at −20° C.]
7. Re-suspend the pellet in 10% culture volume ice-cold TES buffer (50 ml for 500 ml culture) and shake gently on ice for 15 min.
8. Add an equal volume ice-cold 5 mM MgSO₄ (for 2.5 mM final concentration of MgSO₄) and continue shaking gently on ice for a further 15 min.
9. Pellet the suspension by centrifugation at 8000×g for 30 min at 4° C. Supernatant contains released periplasmic proteins.
10. Add 10×PBS (pH 7.4) [final conc. of 1×PBS] to peri-prep extract priorto IMAC purification.

Immobilised Metal Affinity Chromatography (IMAC) Purification

1. Add 2-3 ml Nickel-resin (His Pur Ni-NTA Resin, Thermo Fisher #88222) to 100 ml osmotic shock solution (periplasmic extract) and incubated on roller for 1 hour at room temperature.
2. Allow periplasmic extract to pass through the column (Poly prep chromatography columns 10 ml, Bio-Rad #7321010)
3. Wash the resin with 50-100 ml PBS.
4. Eluted protein with 5×1 ml 500 mM imidazole (pH 8).
5. Dialyze eluates in 3×5 liters PBS with agitation in dialysis cassette (Slide A Lyzer Dialysis cassette 7.000 MWCO, Thermo Fisher #66707)
6. Analyse proteins by SDS-PAGE.

---

We claim:

1. A method for the production of a library of humanized antigen specific antigen binding molecules having a peptide domain structure represented by the following formula (I):

FW1-CDR1-FW2-HV2-FW3a-HV4-FW3b-CDR3-FW4 comprising
(1) amplifying DNA sequences encoding two or more contiguous peptide domains of FW1-CDR1-FW2-HV2-FW3a-HV4-FW3b-CDR3-FW4, wherein said two or more contiguous peptide domains when ligated encode an antigen specific antigen binding molecule of formula (I), in the presence of a plurality of heterologous oligomers complementary to CDR1 or CDR3 domains, to form a plurality of amplified DNA sequences encoding an antigen specific antigen binding molecule of formula (I) wherein FW1 comprises one or more humanized sequences according to –/D A/I/T S/Q/R V/M N/T/D Q S P S S L S A S V G D R V T I T C V L/V T/R D/G T/A/S (SEQ ID NO: 1);
(2) ligating together said amplified DNA sequences encoding two or more contiguous peptide domains to form DNA sequences encoding an antigen specific binding molecule having the peptide domain structure of formula (I);
(3) cloning the ligated DNA obtained in (2) into a display vector; and
(4) transforming a host with said display vector to produce a library of said antigen specific antigen binding molecules.

2. The method of claim 1, wherein:
(a) at least one of FW2, FW3a, FW3b and FW4 each comprise one or more sequences selected from the group consisting of:
FW2 comprises one or more sequences according to T S/Y W F/Y R/Q K/Q N/K P/S G T/S(SEQ ID NO: 2);
FW3a comprises one or more sequences according to G R Y/F V/S E/G S/T V/G/I N/S (SEQ ID NO: 3);
FW3b comprises one or more sequences according to F S/T L R/T I K/S/N D/S L T/Q V/P A/E D S/F A/G T Y Y/R/I C K/R/A A/S/L (SEQ ID NO: 4), and FW4 comprises one or more sequences according to D/Y/F G A/G/Q G T K/V V/L E/T I/V K/N (SEQ ID NO: 5);
and/or
(b) two of FW2, FW3a, FW3b and FW4 comprise a humanized sequence and wherein the remaining two of FW2, FW3a, FW3b and FW4 comprise a sequence for the corresponding at least one of FW2, FW3a, FW3b and FW4 from a member of a species in the Elasmobranchii subclass, or for each sequence from a member of a species in the Elasmobranchii subclass, an amino acid sequence with
  (i) at least 70% identity thereto, and/or
  (ii) one, two, or three amino acid substitutions relative thereto;
and/or
(c) three of FW2, FW3a, FW3b and FW4 comprise a humanized sequence and wherein the remaining one of FW2, FW3a, FW3b and FW4 comprises a sequence for the corresponding at least one of FW2, FW3a, FW3b and FW4 from a member of a species in the Elasmobranchii subclass, or for each sequence from a member of a species in the Elasmobranchii subclass, an amino acid sequence with
  (i) at least 70% identity thereto, and/or
  (ii) one, two, or three amino acid substitutions relative thereto;
and/or
(d) FW4 comprises a sequence for FW4 from a member of a species in the Elasmobranchii subclass;
and/or
(e) FW3a comprises a sequence for FW3a from a member of a species in the Elasmobranchii subclass or wherein FW3b comprises a sequence for FW3b from a member of a species in the Elasmobranchii subclass;
and/or
(f) at least three amino acid residues from the combined sequences of FW2, FW3a, FW3b and FW4 are humanized;
and/or
(g) the one or more humanized sequences for FW1 are selected from the group consisting of:

```
                                          (SEQ ID NO: 6)
A/T S/R V N/D Q S P S S L S A S V
G D R V T I T C V L/V T D/G T/A;
```

```
                                          (SEQ ID NO: 7)
D I Q M T Q S P S S L S A S V G D

R V T I T C V L I V T D/G T/A;
and
```

```
                                          (SEQ ID NO: 8)
ARVDQSPSSLSASVGDRVTITCVLRDS;
``` and/or
(h) the one or more sequences for FW2 are selected from the group consisting of:

```
                                          (SEQ ID NO: 9)
     T S/Y W F/Y R K N P G T/S;
```

```
                                          (SEQ ID NO: 10)
     T S/Y W Y/F Q Q K P G T/S;
and
```

```
                                          (SEQ ID NO: 11)
     TYWYRKKSGS;
``` and/or
(i) the one or more sequences for FW3a are selected from the group consisting of:

```
                                          (SEQ ID NO: 12)
           GRYVESVN;
```

```
                                          (SEQ ID NO: 13)
           GRFSGSGS;
```

```
                                          (SEQ ID NO: 14)
           GRYVETVN;
           and
```

```
                                          (SEQ ID NO: 15)
           GRYVETIN;
``` and/or
(j) the one or more sequences for FW3b are selected from the group consisting of:

```
                                          (SEQ ID NO: 16)
F S L R I K D L T V A D S A T Y Y/I C K/R A;
```

```
                                          (SEQ ID NO: 17)
F T L T I S S L Q P E D F A T Y Y/I C K/R A;
```

```
                                          (SEQ ID NO: 18)
FTLTISSLQPEDFATYYCAS;
and
```

```
                                          (SEQ ID NO: 19)
FSLRINDLTVEDSGTYRCKL;
``` and/or
(k) the one or more sequences for FW4 are selected from the group consisting of:

```
                                          (SEQ ID NO: 20)
     D/Y G A/G/Q G T K V/L E I K;
     and
```

```
                                          (SEQ ID NO: 21)
     YGGGTVVTVN;
``` and/or
(l) at least one of FW2, FW3a, FW3b and FW4 each comprise one or more sequences selected from the group consisting of:

FW2 comprises one or more sequences according to T S/Y W F/Y R/Q K/Q N/K P/S G T/S (SEQ ID NO: 22);

FW3a comprises one or more sequences according to G R Y/F V/S E/G S/T V/G/l N/S (SEQ ID NO: 23);

FW3b comprises one or more sequences according to F S/T L R/T I K/S/N D/S L T/Q V/P A/E D S/F A/G T Y Y/R/l C K/R/A A/S/L (SEQ ID NO: 24); and FW4 comprises one or more sequences according to D/Y G A G T K V E I K (SEQ ID NO: 25).

3. The method of claim 1, wherein:
CDR1 is a region of 6 amino acids,
HV2 is a region of 9 amino acids,
HV4 is a region of 5 amino acids, and/or
CDR3 is a region of 8 to 36 amino acids; and/or
at least one of CDR1, HV2, HV4 and CDR3 each comprise one or more sequences selected from the group consisting of:

CDR1 comprises one or more sequences according to Y/T/R/l/K/N/S C/Y P/S/A/G W/L H/S/Y N/R/G/S (SEQ ID NO: 26), wherein if CDR1 comprises a Cysteine residue CDR3 also comprises a Cysteine residue;

HV2 comprises one or more sequences according to S/T/P N/D Q/W E R I/M S I G/S (SEQ ID NO: 27);

HV4 comprises one or more sequences according to K G/R T/P/S K/M S (SEQ ID NO: 28); and CDR3 comprises one or more sequences according to the following formula (II):

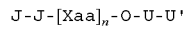

Wherein:
J is any naturally occurring amino acid apart from Cysteine,
Xaa is any naturally occurring amino acid,
n is 3 to 31,
O is an amino acid selected from the group consisting of Cysteine, Aspartic acid, Glutamic acid, Phenylalanine, Glycine, Lysine, Asparagine, Serine, Valine and Tyrosine,
U is an amino acid selected from the group consisting of Cysteine, Aspartic acid, Glycine, Histidine, Tryptophan and Tyrosine,
U' is an amino acid selected from the group consisting of Tyrosine, Leucine, Valine and Phenylalanine; and wherein CDR3 comprises either one Cysteine residue or no Cysteine residues and if CDR3 comprises a Cysteine residue CDR1 also comprises a Cysteine residue.

4. The method of claim 1, further comprising:
subjecting the sequences of one or more of CDR1, HV2, HV4 and CDR3 to controlled mutagenesis, and
selecting desired CDR1, HV2, HV4 and/or CDR3 sequences by affinity maturation against a target molecule.

5. A process for the production of a humanized antigen specific antigen binding molecule, comprising
(1) selecting desired clones from the library prepared according to a method of claim 1;
(2) isolating and purifying the humanized antigen specific antigen binding molecules from these clones;
(3) cloning the DNA sequences encoding the humanized antigen specific antigen binding molecules into an expression vector; and
(4) transforming a host to allow expression of the expression vector.

6. A method as claimed in claim 1, in which the two or more contiguous peptide domains are FW1, CDR1-FW2-HV2-FW3a-HV4-FW3, and CDR3-FW4.

7. A method for preparing a multi-domain antigen specific antigen binding molecule, comprising cultivating or maintaining a host cell comprising an isolated nucleic acid comprising a polynucleotide sequence that encodes a multi-domain antigen specific antigen binding molecule comprising two or more VNAR domains, wherein: each VNAR domain comprises an amino acid sequence having a peptide domain structure represented by the following formula (I): FW1-CDR1-FW2-HV2-FW3a-HV4-FW3b-CDR3-FW4 wherein FW1 of at least one VNAR binding domain comprises a humanized sequence according to –/D A/I/T S/Q/R V/M N/T/D QSPSSLSASVGDRVTITCV L/V T/R D/G T/A/S (SEQ ID NO: 1) and wherein FW4 of at least one VNAR domain comprises a sequence corresponding to FW4 from a member of a species in the Elasmobranchii subclass, or an amino acid sequence with either (i) at least 70% identity thereto, or (ii) one, two, or three amino acid substitutions relative thereto, under conditions such that said host cell produces the multi-domain antigen specific antigen binding molecule, optionally further comprising isolating the multi-domain antigen specific antigen binding molecule.

* * * * *